United States Patent
Barnes et al.

(10) Patent No.: US 8,119,666 B2
(45) Date of Patent: *Feb. 21, 2012

(54) 1,2,5-THIAZOLIDINE DERIVATIVES USEFUL FOR TREATING CONDITIONS MEDIATED BY PROTEIN TYROSINE PHOSPHATASES (PTPASE)

(75) Inventors: David Barnes, Waban, MA (US); Gregory Raymond Bebernitz, Stow, MA (US); Gary Mark Coppola, Budd Lake, NJ (US); Travis Stams, Stow, MA (US); Sidney Wolf Topiol, Fair Lawn, NJ (US); Thalaththani Ralalage Vedananda, Shrewsbury, MA (US); James Richard Wareing, Stow, MA (US)

(73) Assignee: Novartis AG, Basel (CH)

( * ) Notice: Subject to any disclaimer, the term of this patent is extended or adjusted under 35 U.S.C. 154(b) by 136 days.

This patent is subject to a terminal disclaimer.

(21) Appl. No.: 12/096,393

(22) PCT Filed: Dec. 6, 2006

(86) PCT No.: PCT/US2006/046543
§ 371 (c)(1),
(2), (4) Date: Jun. 6, 2008

(87) PCT Pub. No.: WO2007/067613
PCT Pub. Date: Jul. 14, 2007

(65) Prior Publication Data
US 2008/0293776 A1    Nov. 27, 2008

Related U.S. Application Data

(60) Provisional application No. 60/748,491, filed on Dec. 8, 2005.

(51) Int. Cl.
*A61K 31/4436* (2006.01)
*A61K 31/433* (2006.01)
*C07D 417/10* (2006.01)
*C07D 285/10* (2006.01)

(52) U.S. Cl. .................... 514/342; 514/362; 546/268.7; 548/135

(58) Field of Classification Search ................. 548/135; 514/362
See application file for complete search history.

(56) References Cited

U.S. PATENT DOCUMENTS

| | | |
|---|---|---|
| 7,291,635 B2 | 11/2007 | Coppola et al. |
| 2008/0262050 A1 | 10/2008 | Barnes et al. |
| 2008/0293782 A1 | 11/2008 | Barnes et al. |
| 2009/0181928 A1 | 7/2009 | Neubert et al. |
| 2010/0035860 A1 | 2/2010 | Jeyaseelan et al. |
| 2010/0035942 A1 | 2/2010 | Barnes et al. |
| 2010/0197744 A1 | 8/2010 | Barnes et al. |

FOREIGN PATENT DOCUMENTS

WO     03082841 A    10/2003

OTHER PUBLICATIONS

Co-pending U.S. Appl. No. 12/295,545.*
Elchebly, et al., "Increased Insulin Sensitivity and Obesity Resistance in Mice Lacking the Protein Tyrosine Phosphate-1B Gene," Science, vol. 283, pp. 1544-1548 (Mar. 5, 1999).

* cited by examiner

*Primary Examiner* — Rebecca Anderson
*Assistant Examiner* — Alicia L Otton
(74) *Attorney, Agent, or Firm* — John B. Alexander

(57) ABSTRACT

Compounds of the formula

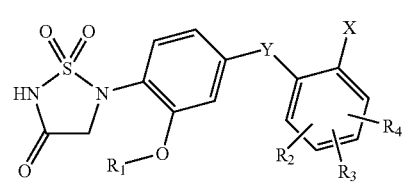

(I)

are inhibitors of protein tyrosine phosphatases (PTPases) and, thus, may be employed for the treatment of conditions mediated by PTPase activity. The compounds of the present invention may also be employed as inhibitors of other enzymes characterized with a phosphotyrosine binding region such as the SH2 domain. Accordingly, the compounds of formula (I) may be employed for prevention and/or treatment of insulin resistance associated with obesity, glucose intolerance, diabetes mellitus, hypertension and ischemic diseases of the large and small blood vessels, conditions that accompany type-2 diabetes, including hyperlipidemia, hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat and/or prevent cancer, osteoporosis, neurodegenerative and infectious diseases, and diseases involving inflammation and the immune system.

17 Claims, No Drawings

1,2,5-THIAZOLIDINE DERIVATIVES USEFUL FOR TREATING CONDITIONS MEDIATED BY PROTEIN TYROSINE PHOSPHATASES (PTPASE)

This application is the National Stage of Application No. PCT/EP2006/046543, filed on Dec. 6, 2006, which claims benefit under 35 U.S.C. §119(a-d) of U.S. Provisional Application No. 60/748,491, filed Dec. 8, 2005, the contents of which are incorporated herein by reference in their entirety.

The present invention relates to thiadiazolidinone derivatives, pharmaceutical compositions containing such compounds, methods of making such and methods of treating conditions mediated by protein tyrosine phosphatases by employing such compounds.

Accordingly, the present invention provides compounds of the formula

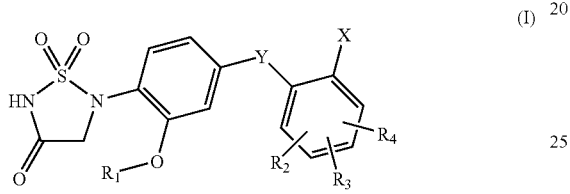

(I)

wherein
$R_1$ is hydrogen, —C(O)$R_5$, —C(O)NR$_6$R$_7$ or —C(O)OR$_8$ in which
  $R_5$ and $R_6$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
  $R_7$ and $R_8$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
$R_2$, $R_3$ and $R_4$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or
$R_2$ and $R_3$ combined are alkylene which together with the ring atoms to which they are attached form a 5- to 7-membered fused ring provided $R_2$ and $R_3$ are attached to carbon atoms adjacent to each other; or
$R_2$ and $R_3$ combined together with the carbon atom to which they are attached form a fused 5- to 6-membered aromatic or heteroaromatic ring provided $R_2$ and $R_3$ are attached to carbon atoms adjacent to each other;

X is hydrogen, fluoro, cyano, or free or esterified carboxy; or
X is —NR$_9$C(O)R$_{10}$, —NR$_9$C(O)OR$_{11}$, —NR$_9$S(O)$_2$R$_{12}$, —(CH$_2$)$_m$S(O)$_2$R$_{13}$, —OS(O)$_2$R$_{14}$ or —O$_n$C(O)NR$_{15}$R$_{16}$ in which
  $R_9$ is hydrogen, lower alkyl, acyl, alkoxycarbonyl or sulfonyl;
  $R_{10}$, $R_{11}$, $R_{12}$, $R_{13}$ and $R_{14}$ are, independently from each other, cycloalkyl, aryl, heterocyclyl, aralkyl, heteroaralkyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or
  $R_{10}$, $R_{12}$ and $R_{13}$ are, independently from each other, —NR$_{17}$R$_{18}$ in which
    $R_{17}$ and $R_{18}$ are, independently from each other, hydrogen, alkyl, cycloalkyl, aralkyl, aryl or heterocyclyl; or
    $R_{17}$ and $R_{18}$ combined are alkylene which together with the nitrogen atom to which they are attached form a 4- to 7-membered ring;
  $R_{15}$ and $R_{16}$ are, independently from each other, hydrogen, alkyl, cycloalkyl, aralkyl, aryl or heterocyclyl; or
  $R_{15}$ and $R_{16}$ combined are alkylene which together with the nitrogen atom to which they are attached form a 4- to 7-membered ring;
  m and n are, independently from each other, zero or an integer of 1; or
C—X is replaced by nitrogen;
Y is CH$_2$, O or S;
or a pharmaceutically acceptable salt thereof.

The compounds of the present invention are inhibitors of protein tyrosine phosphatases (PTPases), in particular, the compounds of formula (I) inhibit PTPase-1B (PTP-1B) and T-cell PTPase (TC PTP) and, thus, may be employed for the treatment of conditions mediated by PTPase activity. Accordingly, the compounds of formula (I) may be employed for treatment of insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

Listed below are definitions of various terms used to describe the compounds of the instant invention. These definitions apply to the terms as they are used throughout the specification unless they are otherwise limited in specific instances either individually or as part of a larger group. In general, whenever an alkyl group is referred to as a part of the structure, an optionally substituted alkyl is also intended.

Accordingly, the term "optionally substituted alkyl" refers to unsubstituted or substituted straight or branched chain hydrocarbon groups having 1 to 20 carbon atoms, preferably 1 to 8 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halogen, hydroxy, cycloalkyl, cycloalkoxy, acyl, acyloxy, alkoxy, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaraloxy, heterocyclyl and heterocyclyloxy including indolyl, imidazolyl, furyl, thienyl, thiazolyl, pyrrolidyl, pyridyl, pyrimidyl, piperidyl, morpholinyl and the like.

The term "lower alkyl" refers to any of the above alkyl groups as described above having 1 to 7, preferably 1 to 4 carbon atoms.

The term "halogen" or "halo" refers to fluorine, chlorine, bromine and iodine.

The term "alkenyl" refers to any of the above alkyl groups having at least 2 carbon atoms and containing a carbon to carbon double bond at the point of attachment. Groups having 2 to 8 carbon atoms are preferred.

The term "alkynyl" refers to any of the above alkyl groups having at least two carbon atoms and containing a carbon to carbon triple bond at the point of attachment. Groups having 2 to 8 carbon atoms are preferred.

The term "alkylene" refers to a straight-chain bridge of 3-6 carbon atoms connected by single bonds, e.g., —(CH$_2$)x—, wherein x is 3-6, which may be interrupted with one or more heteroatoms selected from O, S, S(O), S(O)$_2$ or NR", wherein R" may be hydrogen, alkyl, cycloalkyl, aryl, heterocyclyl, aralkyl, heteroaralkyl, acyl, carbamoyl, sulfonyl, alkoxycarbonyl, aryloxycarbonyl or aralkoxycarbonyl and the like; and the alkylene may further be substituted with one or more substituents selected from hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl, heterocyclyloxy and the like.

The term "cycloalkyl" refers to optionally substituted monocyclic, bicyclic or tricyclic hydrocarbon groups of 3 to 12 carbon atoms, each of which may be substituted by one or more substituents such as alkyl, halo, oxo, hydroxy, alkoxy, alkanoyl, acylamino, carbamoyl, alkylamino, dialkylamino, thiol, alkylthio, nitro, cyano, carboxy, carboxyalkyl, alkoxycarbonyl, sulfonyl, sulfonamido, sulfamoyl, heterocyclyl and the like.

Exemplary monocyclic hydrocarbon groups include but are not limited to cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.
The term "alkanoyl" refers to alkyl-C(O)—.
The term "alkanoyloxy" refers to alkyl-C(O)—O—.
The terms "alkylamino" and "dialkylamino" refer to alkyl-NH— and (alkyl)$_2$N—, respectively.

The term "alkanoylamino" refers to alkyl-C(O)—NH—.
The term "alkylthio" refers to alkyl-S—.
The term "alkylaminothiocarbonyl" refers to alkyl-NHC(S)—.
The term "trialkylsilyl" refers to (alkyl)$_3$Si—.
The term "trialkylsilyloxy" refers to (alkyl)$_3$SiO—.
The term "alkylthiono" refers to alkyl-S(O)—.
The term "alkylsulfonyl" refers to alkyl-S(O)$_2$—.
The term "alkoxycarbonyl" refers to alkyl-O—C(O)—.
The term "alkoxycarbonyloxy" refers to alkyl-O—C(O)O—.
The term "carboxycarbonyl" refers to HO—C(O)C(O)—.
The term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.
The term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.
The term "sulfonamido" refers to alkyl-S(O)$_2$—NH—, aryl-S(O)$_2$—NH—, aralkyl-S(O)$_2$—NH—, heteroaryl-S(O)$_2$—NH—, heteroaralkyl-S(O)$_2$—NH—, alkyl-S(O)$_2$—N(alkyl)-, aryl-S(O)$_2$—N(alkyl)-, aralkyl-S(O)$_2$—N(alkyl)-, heteroaryl-S(O)$_2$—N(alkyl)-, heteroaralkyl-S(O)$_2$—N(alkyl)- and the like.
The term "sulfonyl" refers to alkylsulfonyl, arylsulfonyl, heteroarylsulfonyl, aralkylsulfonyl, heteroaralkylsulfonyl and the like.
The term "sulfonate" or "sulfonyloxy" refers to alkyl-S(O)$_2$—O—, aryl-S(O)$_2$—O—, aralkyl-S(O)$_2$—O—, heteroaryl-S(O)$_2$—O—, heteroaralkyl-S(O)$_2$—O— and the like.
The term "optionally substituted amino" refers to a primary or secondary amino group which may optionally be substituted by a substituent such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carboxycarbonyl, carbamoyl, alkylaminothiocarbonyl, arylaminothiocarbonyl and the like.
The term "aryl" refers to monocyclic or bicyclic aromatic hydrocarbon groups having 6 to 12 carbon atoms in the ring portion, such as phenyl, naphthyl, tetrahydronaphthyl, biphenyl and diphenyl groups, each of which may optionally be substituted by one to five substituents such as alkyl, trifluoromethyl, halo, hydroxy, alkoxy, acyl, alkanoyloxy, optionally substituted amino, thiol, alkylthio, nitro, cyano, carboxy, carboxyalkyl, alkoxycarbonyl, carbamoyl, alkylthiono, sulfonyl, sulfonamido, sulfonate, heterocyclyl and the like.
The term "monocyclic aryl" refers to optionally substituted phenyl as described under aryl.
The term "aralkyl" refers to an aryl group bonded directly through an alkyl group, such as benzyl.
The term "aralkanoyl" refers to aralkyl-C(O)—.
The term "aralkylthio" refers to aralkyl-S—.
The term "aralkoxy" refers to an aryl group bonded directly through an alkoxy group.
The term "arylsulfonyl" refers to aryl-S(O)$_2$—.
The term "arylthio" refers to aryl-S—.
The term "aroyl" refers to aryl-C(O)—.
The term "aroylamino" refers to aryl-C(O)—NH—.
The term "aryloxycarbonyl" refers to aryl-O—C(O)—.
The term "heterocyclyl" or "heterocyclo" refers to an optionally substituted, aromatic, or a partially or fully saturated nonaromatic cyclic group, for example, which is a 4- to 7-membered monocyclic, 7- to 12-membered bicyclic, or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, benzodiazepinyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups that are substituted with 1, 2 or 3 substituents selected from the group consisting of the following:
(a) optionally substituted alkyl;
(b) hydroxy (or protected hydroxy);
(c) halo;
(d) oxo (i.e. =O);
(e) optionally substituted amino, alkylamino or dialkylamino;
(f) alkoxy;
(g) cycloalkyl;
(h) carboxy;
(i) heterocyclooxy;
(j) alkoxycarbonyl, such as unsubstituted lower alkoxycarbonyl;
(k) mercapto;
(i) nitro;
(m) cyano;
(n) sulfamoyl or sulfonamido;
(o) alkylcarbonyloxy;
(p) arylcarbonyloxy;
(q) arylthio;
(r) aryloxy;
(s) alkylthio;
(t) formyl;
(u) carbamoyl;
(v) aralkyl; and
(w) aryl substituted with alkyl, cycloalkyl, alkoxy, hydroxy, amino, acylamino, alkylamino, dialkylamino or halo.

The term "heterocyclooxy" denotes a heterocyclic group bonded through an oxygen bridge.

The term "heteroaryl" refers to an aromatic heterocycle, for example monocyclic or bicyclic aryl, such as pyrrolyl, pyrazolyl, imidazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl, and the like, optionally substituted by e.g. lower alkyl, lower alkoxy or halo.

The term "heteroarylsulfonyl" refers to heteroaryl-$S(O)_2$—.

The term "heteroaroyl" refers to heteroaryl-C(O)—.

The term "heteroaroylamino" refers to heteroaryl-C(O)NH—

The term "heteroaralkyl" refers to a heteroaryl group bonded through an alkyl group.

The term "heteroaralkanoyl" refers to heteroaralkyl-C(O)—.

The term "heteroaralkanoylamino" refers to heteroaralkyl-C(O)NH—.

The term "acyl" refers to alkanoyl, cycloalkanoyl, aroyl, heteroaroyl, aralkanoyl, heteroaralkanoyl and the like.

The term "acyloxy" refers to alkanoyloxy, cycloalkanoyloxy, aroyloxy, heteroaroyloxy, aralkanoyloxy, heteroaralkanoyloxy and the like.

The term "acylamino" refers to alkanoylamino, cycloalkanoylamino, aroylamino, heteroaroylamino, aralkanoylamino, heteroaralkanoylamino and the like.

The term "esterified carboxy" refers to optionally substituted alkoxycarbonyl, cycloalkoxycarbonyl, aryloxycarbonyl, aralkoxycarbonyl, heterocyclooxycarbonyl and the like.

Pharmaceutically acceptable salts of any compound of the present invention refer to salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris(hydroxymethyl)-methyl-ammonium salts, and salts with amino acids.

Similarly acid addition salts, such as those formed with mineral acids, organic carboxylic acids and organic sulfonic acids e.g. hydrochloric acid, maleic acid and methanesulfonic acid, are possible provided a basic group, such as pyridyl, constitutes part of the structure.

As described herein above, the present invention provides 1,1-dioxo-1,2,5-thiadiazolidin-3-one derivatives of formula (I), pharmaceutical compositions containing the same, methods for preparing such compounds and methods of treating and/or preventing conditions associated with PTPase activity, in particular, PTP-1B and TC PTP activity, by administration of a therapeutically effective amount of a compound of the present invention, or a pharmaceutical composition thereof.

Preferred are the compounds of formula (I) wherein
Y is $CH_2$;
or a pharmaceutically acceptable salt thereof.

Further preferred are the compounds of formula (I) having the formula

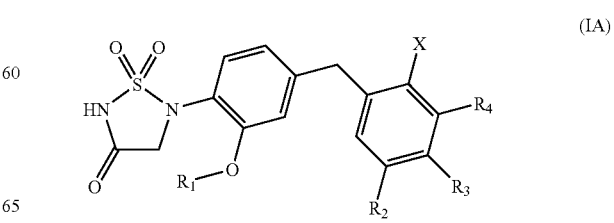

(IA)

wherein
- $R_1$ is hydrogen, —C(O)$R_5$, —C(O)N$R_6R_7$ or —C(O)O$R_8$ in which
  - $R_5$ and $R_6$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
  - $R_7$ and $R_8$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
- $R_2$, $R_3$ and $R_4$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or
- $R_2$ and $R_3$ combined are alkylene which together with the ring atoms to which they are attached form a 5- to 7-membered fused ring; or
- $R_2$ and $R_3$ combined together with the carbon atom to which they are attached form a fused 5- to 6-membered aromatic or heteroaromatic ring;
- X is cyano; or
- X is —N$R_9$C(O)$R_{10}$, —N$R_9$C(O)O$R_{11}$, —N$R_9$S(O)$_2R_{12}$, —(CH$_2$)$_m$S(O)$_2R_{13}$ or —OS(O)$_2R_{14}$ in which
  - $R_9$ is hydrogen or lower alkyl;
  - $R_{10}$, $R_{11}$, $R_{12}$, $R_{13}$ and $R_{14}$ are, independently from each other, cycloalkyl, aryl, heterocyclyl, aralkyl, heteroaralkyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or
  - $R_{10}$, $R_{12}$ and $R_{13}$ are, independently from each other, —N$R_{17}R_{18}$ in which
    - $R_{17}$ and $R_{18}$ are, independently from each other, hydrogen, alkyl, cycloalkyl, aralkyl, aryl or heterocyclyl; or
    - $R_{17}$ and $R_{18}$ combined are alkylene which together with the nitrogen atom to which they are attached form a 4- to 7-membered ring;
  - m is zero; or
- C—X is replaced by nitrogen;

or a pharmaceutically acceptable salt thereof.

Preferred are the compounds of formula (IA) wherein
X is cyano; or
X is —N$R_9$S(O)$_2R_{12}$ or —OS(O)$_2R_{14}$ in which
  $R_9$ is hydrogen or lower alkyl;
  $R_{12}$ and $R_{14}$ are, independently from each other, cycloalkyl, aryl, heterocyclyl, aralkyl, heteroaralkyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy;

or a pharmaceutically acceptable salt thereof.

Especially preferred are the compounds of formula (IA), designated as the A group, wherein
  $R_9$ is hydrogen;
or a pharmaceutically acceptable salt thereof.

Preferred are the compounds in the A group wherein
  $R_{12}$ and $R_{14}$ are, independently from each other, monocyclic aryl or C$_{(1-4)}$alkyl;
or a pharmaceutically acceptable salt thereof.

Further preferred are the compounds in the A group wherein
  $R_1$ is hydrogen or —C(O)$R_5$ in which $R_5$ is monocyclic aryl;
or a pharmaceutically acceptable salt thereof.

Especially preferred are also the compounds of formula (IA), designated as the B group, wherein
  $R_2$, $R_3$ and $R_4$ are, independently from each other, hydrogen, halogen, hydroxy, monocyclic aryl, C$_{(1-4)}$alkoxy or C$_{(1-4)}$alkyl optionally substituted with at least one halogen;
or a pharmaceutically acceptable salt thereof.

Preferred are the compounds in the B group wherein
  $R_9$ is hydrogen;
or a pharmaceutically acceptable salt thereof.

Further preferred are the compounds in the B group wherein
  $R_{12}$ and $R_{14}$ are, independently from each other, monocyclic aryl or C$_{(1-4)}$alkyl;
or a pharmaceutically acceptable salt thereof.

More preferred are the compounds in the B group wherein
  $R_1$ is hydrogen or —C(O)$R_5$ in which $R_5$ is monocyclic aryl;
or a pharmaceutically acceptable salt thereof.

Particular embodiments of the invention are:
5-(4-Benzyl-2-hydroxyphenyl)-1,1-dioxo-1,2,5-thiadiazolidin-3-one;
5-[2-Hydroxy-4-(3-hydroxybenzyl)-phenyl]-1,1-dioxo-1,2,5-thiadiazolidin-3-one;
5-[2-Hydroxy-4-(3-methoxybenzyl)-phenyl]-1,1-dioxo-1,2,5-thiadiazolidin-3-one;
5-[4-(2-Fluoro-3-trifluoromethylbenzyl)-2-hydroxyphenyl]-1,1-dioxo-1,2,5-thiadiazolidin-3-one;
2-[3-Hydroxy-4-(1,1,4-trioxo-1,2,5-thiadiazolidin-2-yl)-benzyl]-benzonitrile;
5-[4-(2-Fluorobenzyl)-2-hydroxyphenyl]-1,1-dioxo-1,2,5-thiadiazolidin-3-one;
5-(2-Hydroxy-4-naphthalen-2-ylmethylphenyl)-1,1-dioxo-1,2,5-thiadiazolidin-3-one;
5-[2-Hydroxy-4-(3-trifluoromethylbenzylphenyl]-1,1-dioxo-1,2,5-thiadiazolidin-3-one;
5-[2-Hydroxy-4-(2-methylbenzyl)phenyl]-1,1-dioxo-1,2,5-thiadiazolidin-3-one;
5-[4-(4-Fluorobenzyl)-2-hydroxyphenyl]-1,1-dioxo-1,2,5-thiadiazolidin-3-one;
3-[3-Hydroxy-4-(1,1,4-trioxo-1,2,5-thiadiazolidin-2-yl)-benzyl]-benzoic acid methyl ester;

5-(4-Biphenyl-3-ylmethyl-2-hydroxyphenyl)-1,1-dioxo-1,2,5-thiadiazolidin-3-one;
5-[4-(3-Fluoro-4-methylbenzyl)-2-hydroxyphenyl]-1,1-dioxo-1,2,5-thiadiazolidin-3-one;
5-[2-Hydroxy-4-(4-methylbenzyl)phenyl]-1,1-dioxo-1,2,5-thiadiazolidin-3-one;
5-[2-Hydroxy-4-(4-hydroxybenzyl)phenyl]-1,1-dioxo-1,2,5-thiadiazolidin-3-one;
5-[4-(3-Fluorobenzyl)-2-hydroxyphenyl]-1,1-dioxo-1,2,5-thiadiazolidin-3-one;
5-[4-(4-tert-Butylbenzyl)-2-hydroxyphenyl]-1,1-dioxo-1,2,5-thiadiazolidin-3-one;
5-[4-{2-Benzenesulfonylmethylbenzyl)-2-hydroxyphenyl]-1,1-dioxo-1,2,5-thiadiazolidin-3-one;
5-[2-Hydroxy-4-(3-methylbenzyl)phenyl]-1,1-dioxo-1,2,5-thiadiazolidin-3-one;
{2-[3-Hydroxy-4-(1,1,4-trioxo-1,2,5-thiadiazolidin-2-yl)-benzyl]-phenyl}-carbamic acid tert-butyl ester;
N-{2-[3-Hydroxy-4-(1,1,4-trioxo-1,2,5-thiadiazolidin-2-yl)-benzyl]-phenyl}-C-phenyl-methanesulfonamide;
N-{2-[3-Hydroxy-4-(1,1,4-trioxo-1,2,5-thiadiazolidin-2-yl)-benzyl]-phenyl}-benzenesulfonamide;
Ethanesulfonic acid {2-[3-hydroxy-4-(1,1,4-trioxo-1,2,5-thiadiazolidin-2-yl)-benzyl]-phenyl}-amide;
Propane-1-sulfonic acid {2-[3-hydroxy-4-(1,1,4-trioxo-1,2,5-thiadiazolidin-2-yl)-benzyl]-phenyl}-amide;
Butane-1-sulfonic acid {2-[3-hydroxy-4-(1,1,4-trioxo-1,2,5-thiadiazolidin-2-yl)-benzyl]-phenyl}-amide;
C-Cyclohexyl-N-{2-[3-hydroxy-4-(1,1,4-trioxo-1,2,5-thiadiazolidin-2-yl)-benzyl]-phenyl}-methanesulfonamide;
N-{2-[3-Hydroxy-4-(1,1,4-trioxo-1,2,5-thiadiazolidin-2-yl)-benzyl]-phenyl}-methanesulfonamide;
N-{2-[3-Hydroxy-4-(1,1,4-trioxo-1,2,5-thiadiazolidin-2-yl)-benzyl]-phenyl}-4-isopropylbenzenesulfonamide;
N-{2-[3-Hydroxy-4-(1,1,4-trioxo-1,2,5-thiadiazolidin-2-yl)-benzyl]-phenyl}-aminosulfonamide;
N-{3-[3-Hydroxy-4-(1,1,4-trioxo-1,2,5-thiadiazolidin-2-yl)-benzyl]-naphthalen-2-yl}-methanesulfonamide;
N-{2-[3-Hydroxy-4-(1,1,4-trioxo-1,2,5-thiadazolidin-2-yl)-benzyl]-phenyl}-acetamide;
4-tert-Butyl-N-{2-[3-hydroxy-4-(1,1,4-trioxo-1,2,5-thiadiazolidin-2-yl)-benzyl]-phenyl}-benzamide;
N-{2-[3-Hydroxy-4-(1,1,4-trioxo-1,2,5-thiadiazolidin-2-yl)-benzyl]-phenyl}-benzamide;
5-[4-(4-Ethylpyridin-2-ylmethyl)-2-hydroxyphenyl]-1,1-dioxo-1,2,5-thiadiazolidin-3-one;
5-[4-(6-Methoxypyridin-2-ylmethyl)-2-hydroxyphenyl]-1,1-dioxo-1,2,5-thiadiazolidin-3-one;
5-(2-Hydroxy-4-pyridin-2-ylmethylphenyl)-1,1-dioxo-1,2,5-thiadiazolidin-3-one;
5-[2-Hydroxy-4-(2-methanesulfonylbenzyl)-phenyl]-1,1-dioxo-1,2,5-thiadiazolidin-3-one;
N-{2-[3-Hydroxy-4-(1,1,4-trioxo-1,2,5-thiadiazolidin-2-yl)-benzyl]-phenyl}-N-methylmethanesulfonamide;
5-[2-Hydroxy-4-(2-methanesulfonylmethylbenzyl)-phenyl]-1,1-dioxo-1,2,5-thiadiazolidin-3-one;
5-{4-(3-Methansulfonylphenyl)methyl-2-hydroxyphenyl}-1,1-dioxo-1,2,5-thiadiazolidin-3-one;
C-{2-[3-Hydroxy-4-(1,1,4-trioxo-1,2,5-thiadiazolidin-2-yl)-benzyl]-phenyl}-N,N-dimethylmethanesulfonamide;
Methanesulfonic acid 2-[3-hydroxy-4-(1,1,4-trioxo-1,2,5-thiadiazolidin-2-yl)-benzyl]-phenyl ester;
Methanesulfonic acid 3-[3-hydroxy-4-(1,1,4-trioxo-1,2,5-thiadiazolidin-2-yl)-benzyl]-naphthalen-2-yl ester;
Methanesulfonic acid 2-[3-hydroxy-4-(1,1,4-trioxo-1,2,5-thiadiazolidin-2-yl)-benzyl]-naphthalen-1-yl ester;
Methanesulfonic acid 2-[3-hydroxy-4-(1,1',4-trioxo-1,2,5-thiadiazolidin-2-yl)-benzyl]-4-methylphenyl ester;
Methanesulfonic acid 1-[3-hydroxy-4-(1,1,4-trioxo-1,2,5-thiadiazolidin-2-yl)-benzyl]-naphthalen-2-yl ester;
Methanesulfonic acid 2-[3-hydroxy-4-(1,1,4-trioxo-1,2,5-thiadiazolidin-2-yl)-benzyl]-4-methoxyphenyl ester;
Methanesulfonic acid 2-[3-hydroxy-4-(1,1,4-trioxo-1,2,5-thiadiazolidin-2-yl)-benzyl]-6-methylphenyl ester;
Ethanesulfonic acid 2-[3-hydroxy-4-(1,1,4-trioxo-1,2,5-thiadiazolidin-2-yl)-benzyl]-4-methylphenyl ester;
Propane-1-sulfonic acid 2-[3-hydroxy-4-(1,1,4-trioxo-1,2,5-thiadiazolidin-2-yl)-benzyl]-4-methylphenyl ester;
Methanesulfonic acid 4-chloro-2-[3-hydroxy-4-(1,1,4-trioxo-1,2,5-thiadiazolidin-2-yl)-benzyl]-phenyl ester;
Methanesulfonic acid 2-[3-hydroxy-4-(1,1,4-trioxo-1,2,5-thiadiazolidin-2-yl)-benzyl]-5-methylphenyl ester;
Methanesulfonic acid 4-chloro-2-[3-hydroxy-4-(1,1,4-trioxo-1,2,5-thiadiazolidin-2-yl)-benzyl]-6-methylphenyl ester;
Ethanesulfonic acid 2-[3-hydroxy-4-(1,1,4-trioxo-1,2,5-thiadiazolidin-2-yl)-benzyl]-phenyl ester;
Propane-1-sulfonic acid 2-[3-hydroxy-4-(1,1,4-trioxo-1,2,5-thiadiazolidin-2-yl)-benzyl]-phenyl ester;
5-[4-(2-Fluoro-4-methylbenzyl)-2-hydroxyphenyl]-1,1-dioxo-1,2,5-thiadiazolidin-3-one;
3-[3-Hydroxy-4-(1,1,4-trioxo-1,2,5-thiadiazolidin-2-yl)-benzyl]-N-methylbenzamide potassium salt;
3-[3-Hydroxy-4-(1,1,4-trioxo-1,2,5-thiadiazolidin-2-yl)-benzyl]-benzoic acid dipotassium salt;
2-[3-Hydroxy-4-(1,1,4-trioxo-1,2,5-thiadiazolidin-2-yl)-benzyl]-benzoic acid;
5-[4-(2,5-Difluorobenzyl)-2-hydroxyphenyl]-1,1-dioxo-1,2,5-thiadiazolidin-3-one;
5-[4-(3-Ethylbenzyl)-2-hydroxyphenyl]-1,1-dioxo-1,2,5-thiadiazolidin-3-one;
5-(2-Hydroxy-4-phenoxyphenyl)-1,1-dioxo-1,2,5-thiadiazolidin-3-one potassium salt;
2-Hydroxy-6-[3-hydroxy-4-(1,1,4-trioxo-1,2,5-thiadiazolidin-2-yl)-benzyl]-benzonitrile;
2-[3-Hydroxy-4-(1,1,4-trioxo-1,2,5-thiadiazolidin-2-yl)-benzyl]-4-trifluoromethylbenzonitrile;
2-[3-Hydroxy-4-(1,1,4-trioxo-1,2,5-thiadiazolidin-2-yl)-benzyl]-4-methylbenzonitrile;
2-[3-Hydroxy-4-(1,1,4-trioxo-1,2,5-thiadiazolidin-2-yl)-benzyl]-6-methyl-benzonitrile;
2-[3-Hydroxy-4-(1,1,4-trioxo-1,2,5-thiadiazolidin-2-yl)-benzyl]-4-trifluoromethylbenzonitrile;
5-(2-Hydroxy-4-phenylsulfanylphenyl)-1,1-dioxo-1,2,5-thiadiazolidin-3-one;
2-[3-Hydroxy-4-(1,1,4-trioxo-1,2,5-thiadiazolidin-2-yl)-phenylsulfanyl]-4-trifluoromethylbenzonitrile;
2-[3-Hydroxy-4-(1,1,4-trioxo-1,2,5-thiadiazolidin-2-yl)-phenylsulfanyl]-6-trifluoromethylbenzonitrile;
Methanesulfonic acid 2-[3-diethylcarbamoyloxy-4-(1,1,4-trioxo-1,2,5-thiadiazolidin-2-yl)-benzyl]-phenyl ester;
Methanesulfonic acid 2-[3-isopropoxycarbonyloxy-4-(1,1,4-trioxo-1,2,5-thiadiazolidin-2-yl)-benzyl]-phenyl ester;
N-{4-Chloro-2-[3-hydroxy-4-(1,1,4-trioxo-1,2,5-thiadiazolidin-2-yl)-benzyl]-phenyl}-methanesulfonamide;
N-{2-[3-Hydroxy-4-(1,1,4-trioxo-1,2,5-thiadiazolidin-2-yl)-benzyl]-4-methylphenyl}-methanesulfonamide;
N-{4-Fluoro-2-[3-hydroxy-4-(1,1,4-trioxo-1,2,5-thiadiazolidin-2-yl)-benzyl]-phenyl}-methanesulfonamide;
N-{4-Fluoro-2-[3-hydroxy-4-(1,1,4-trioxo-1,2,5-thiadiazolidin-2-yl)-benzyl]-phenyl}-benzenesulfonamide;
Ethanesulfonic acid {4-fluoro-2-[3-hydroxy-4-(1,1,4-trioxo-1,2,5-thiadiazolidin-2-yl)-benzyl]-phenyl}-amide;

Propane-2-sulfonic acid {4-fluoro-2-[3-hydroxy-4-(1,1,4-trioxo-1,2,5-thiadiazolidin-2-yl)-benzyl]-phenyl}-amide;
Propane-1-sulfonic acid {2-[3-hydroxy-4-(1,1,4-trioxo-1,2,5-thiadiazolidin-2-yl)-benzyl]-4-methylphenyl}-amide;
N-{4-Fluoro-2-[3-hydroxy-4-(1,1,4-trioxo-1,2,5-thiadiazolidin-2-yl)-benzyl]-phenyl}-C-phenyl-methanesulfonamide;
Ethanesulfonic acid {4-chloro-2-[3-hydroxy-4-(1,1,4-trioxo-1,2,5-thiadiazolidin-2-yl)-benzyl]-phenyl}-amide;
Propane-2-sulfonic acid {4-chloro-2-[3-hydroxy-4-(1,1,4-trioxo-1,2,5-thiadiazolidin-2-yl)-benzyl]-phenyl}-amide;
Propane-1-sulfonic acid {4-chloro-2-[3-hydroxy-4-(1,1,4-trioxo-1,2,5-thiadiazolidin-2-yl)-benzyl]-phenyl}-amide;
Ethanesulfonic acid {4-chloro-2-[3-hydroxy-4-(1,1,4-trioxo-1,2,5-thiadiazolidin-2-yl)-benzyl]-6-methylphenyl}-amide;
N-{2-[3-Hydroxy-4-(1,1,4-trioxo-1,2,5-thiadiazolidin-2-yl)-benzyl]-6-methylphenyl}-methanesulfonamide;
N-{2-[3-Hydroxy-4-(1,1,4-trioxo-1,2,5-thiadiazolidin-2-yl)-benzyl]-4,6-dimethylphenyl}-methanesulfonamide;
Ethanesulfonic acid {2-[3-hydroxy-4-(1,1,4-trioxo-1,2,5-thiadiazolidin-2-yl)-benzyl]-6-methylphenyl}-amide;
Propane-1-sulfonic acid {2-[3-hydroxy-4-(1,1,4-trioxo-1,2,5-thiadiazolidin-2-yl)-benzyl]-6-methylphenyl}-amide;
Ethanesulfonic acid {2-[3-hydroxy-4-(1,1,4-trioxo-1,2,5-thiadiazolidin-2-yl)-benzyl]-4,6-dimethylphenyl}-amide;
N-{4-Chloro-2-[3-hydroxy-4-(1,1,4-trioxo-1,2,5-thiadiazolidin-2-yl)-benzyl]-6-methylphenyl}-methanesulfonamide;
N-{4-Chloro-2-[3-hydroxy-4-(1,1,4-trioxo-1,2,5-thiadiazolidin-2-yl)-benzyl]-6-methylphenyl}-methanesulfonamide;
N-{2-[3-Hydroxy-4-(1,1,4-trioxo-1,2,5-thiadiazolidin-2-yl)-benzyl]-5-methylphenyl}-methanesulfonamide;
N-{2-[3-Hydroxy-4-(1,1,4-trioxo-1,2,5-thiadiazolidin-2-yl)-benzyl]-6-methoxyphenyl}-methanesulfonamide;
N-{5-Chloro-2-[3-hydroxy-4-(1,1,4-trioxo-1,2,5-thiadiazolidin-2-yl)-benzyl]-phenyl}-methanesulfonamide;
Ethanesulfonic acid {2-[3-hydroxy-4-(1,1,4-trioxo-1,2,5-thiadiazolidin-2-yl)-benzyl]-4-methylphenyl}-amide;
Methanesulfonic acid 4-ethyl-2-[3-hydroxy-4-(1,1,4-trioxo-1,2,5-thiadiazolidin-2-yl)-benzyl]-phenyl ester;
Methanesulfonic acid 4-tert-butyl-2-[3-hydroxy-4-(1,1,4-trioxo-1,2,5-thiadiazolidin-2-yl)-benzyl]-phenyl ester;
Diethylcarbamic acid 2-[3-hydroxy-4-(1,1,4-trioxo-1,2,5-thiadiazolidin-2-yl)-benzyl]-4-methylphenyl ester;
Ethanesulfonic acid {4-ethyl-2-[3-hydroxy-4-(1,1,4-trioxo-1,2,5-thiadiazolidin-2-yl)-benzyl]-phenyl}-amide;
Propane-1-sulfonic acid {4-ethyl-2-[3-hydroxy-4-(1,1,4-trioxo-1,2,5-thiadiazolidin-2-yl)-benzyl]-phenyl}-amide;
N-{4-Ethyl-2-[3-hydroxy-4-(1,1,4-trioxo-1,2,5-thiadiazolidin-2-yl)-benzyl]-phenyl}-methanesulfonamide;
N-{4-Benzyl-2-[3-hydroxy-4-(1,1,4-trioxo-1,2,5-thiadiazolidin-2-yl)-benzylphenyl}methanesulfonamide;
N-{3-[3-Hydroxy-4-(1,1,4-trioxo-1,2,5-thiadiazolidin-2-yl)-benzyl]-biphenyl-4-yl}-methanesulfonamide;
N-{2-[3-Hydroxy-4-(1,1,4-trioxo-1,2,5-thiadiazolidin-2-yl)-benzyl]-4-methoxyphenyl}-methanesulfonamide;
Ethanesulfonic acid {2-[3-hydroxy-4-(1,1,4-trioxo-1,2,5-thiadiazolidin-2-yl)-benzyl]-4-methoxyphenyl}-amide;
Propane-1-sulfonic acid {2-[3-hydroxy-4-(1,1,4-trioxo-1,2,5-thiadiazolidin-2-yl)-benzyl]-4-methoxyphenyl}-amide;
Methanesulfonic acid 5-[3-hydroxy-4-(1,1,4-trioxo-1,2,5-thiadiazolidin-2-yl)-benzyl]-7-methylindan-4-yl ester;
Methanesulfonic acid 6-[3-hydroxy-4-(1,1,4-trioxo-1,2,5-thiadiazolidin-2-yl)-benzyl]-indan-5-yl ester;
N-{2-[4-(1,1-dioxido-4-oxo-1,2,5-thiadiazolidin-2-yl)-3-hydroxybenzyl]-1,4-dimethylphenyl}sulfamide;
N-{2-[4-(1,1-dioxido-4-oxo-1,2,5-thiadiazolidin-2-yl)-3-hydroxybenzyl]-1-methyl-4-chlorophenyl}sulfamide;
N-{2-[4-(1,1-dioxido-4-oxo-1,2,5-thiadiazolidin-2-yl)-3-hydroxybenzyl]-4-ethylphenyl}sulfamide;
Methanesulfonic acid 2-[3-hydroxy-4-(1,1,4-trioxo-1,2,5-thiadiazolidin-2-yl)-benzyl]-6-isopropylphenyl ester;
Methanesulfonic acid 2-[3-hydroxy-4-(1,1,4-trioxo-1,2,5-thiadiazolidin-2-yl)-benzyl]-5-methylphenyl ester;
Methanesulfonic acid 2-chloro-6-[3-hydroxy-4-(1,1,4-trioxo-1,2,5-thiadiazolidin-2-yl)-benzyl]-phenyl ester;
Methanesulfonic acid 5-chloro-2-[3-hydroxy-4-(1,1,4-trioxo-1,2,5-thiadiazolidin-2-yl)-benzyl]-phenyl ester;
Methanesulfonic acid 2-[3-hydroxy-4-(1,1,4-trioxo-1,2,5-thiadiazolidin-2-yl)-benzyl]-5-methoxyphenyl ester;
Methanesulfonic acid 2-[3-hydroxy-4-(1,1,4-trioxo-1,2,5-thiadiazolidin-2-yl)-benzyl]-6-methoxyphenyl ester;
N-{2-Chloro-6-[3-hydroxy-4-(1,1,4-trioxo-1,2,5-thiadiazolidin-2-yl)-benzyl]-phenyl}-methanesulfonamide;
Methanesulfonic acid 2-[3-hydroxy-4-(1,1,4-trioxo-1,2,5-thiadiazolidin-2-yl)-benzyl]-4,6-dimethylphenyl ester;
Benzoic acid 5-benzyl-2-(1,1,4-trioxo-1,2,5-thiadiazolidin-2-yl)-phenyl ester;
Benzoic acid 5-(2-methanesulfonyloxybenzyl)-2-(1,1,4-trioxo-1,2,5-thiadiazolidin-2-yl)-phenyl ester;
Benzoic acid 5-(2-methanesulfonyloxy-5-methylbenzyl)-2-(1,1,4-trioxo-1,2,5-thiadiazolidin-2-yl)-phenyl ester;
Benzoic acid 5-(2-methanesulfonylamino-5-methylbenzyl)-2-(1,1,4-trioxo-1,2,5-thiadiazolidin-2-yl)-phenyl ester;
Benzoic acid 5-(2-methanesulfonylaminobenzyl)-2-(1,1,4-trioxo-1,2,5-thiadiazolidin-2-yl)-phenyl ester;
Benzoic acid 5-[2-(benzoylmethanesulfonylamino)-5-methylbenzyl]-2-(1,1,4-trioxo-1,2,5-thiadiazolidin-2-yl)-phenyl ester;
Benzoic acid 5-[2-(benzoylmethanesulfonylamino)-benzyl]-2-(1,1,4-trioxo-1,2,5-thiadiazolidin-2-yl)-phenyl ester;
2-Amino-3-methylbutyric acid 5-(2-methanesulfonyloxybenzyl)-2-(1,1,4-trioxo-1,2,5-thiadiazolidin-2-yl)-phenyl ester;
Benzoic acid 5-(5-chloro-2-methanesulfonylamino-3-methylbenzyl)-2-(1,1,4-trioxo-1,2,5-thiadiazolidin-2-yl)-phenyl ester;
Benzoic acid 5-(2-methanesulfonylamino-3,5-dimethylbenzyl)-2-(1,1,4-trioxo-1,2,5-thiadiazolidin-2-yl)-phenyl ester;
2-Amino-3-methylbutyric acid 5-(2-methanesulfonyloxy-5-methylbenzyl-2-(1,1,4-trioxo-1,2,5-thiadiazolidin-2-yl)-phenyl ester;
Benzoic acid 5-(2-methanesulfonyloxy-3,5-dimethylbenzyl)-2-(1,1,4-trioxo-1,2,5-thiadiazolidin-2-yl)-phenyl ester;
Methanesulfonic acid 2-[3-methoxycarbonyloxy-4-(1,1,4-trioxo-1,2,5-thiadiazolidin-2-yl)-benzyl]-4-methylphenyl ester;
2-Amino-3-methylbutyric acid 5-(2-methanesulfonylaminobenzyl)-2-(1,1,4-trioxo-1,2,5-thiadiazolidin-2-yl)-phenyl ester;
2-(1,1-dioxido-4-oxo-1,2,5-thiadiazolidin-2-yl)-5-{2-[(methoxycarbonyl)(methylsulfonyl)-amino]-3,5-dimethylbenzyl}phenyl methyl carbonate;
Carbonic acid 5-(2-methanesulfonylamino-3,5-dimethylbenzyl)-2-(1,1,4-trioxo-1,2,5-thiadiazolidin-2-yl)-phenyl ester methyl ester;
Benzoic acid 5-(2-methanesulfonylamino-4-methylbenzyl)-2-(1,1,4-trioxo-1,2,5-thiadiazolidin-2-yl)-phenyl ester;

Benzoic acid 5-(2-methanesulfonyloxy-4-methylbenzyl)-2-(1,1,4-trioxo-1,2,5-thiadiazolidin-2-yl)-phenyl ester;
Benzoic acid 5-[2-(benzoylmethanesulfonylamino)-4-methylbenzyl]-2-(1,1,4-trioxo-1,2,5-thiadiazolidin-2-yl)-phenyl ester;
Benzoic acid 5-(2-methanesulfonyloxy-3-methylbenzyl)-2-(1,1,4-trioxo-1,2,5-thiadiazolidin-2-yl)-phenyl ester;
Benzoic acid 5-(5-chloro-2-methanesulfonyloxy-3-methylbenzyl)-2-(1,1,4-trioxo-1,2,5-thiadiazolidin-2-yl)-phenyl ester;
Benzoic acid 5-[2-(benzoylmethanesulfonylamino)-3-methylbenzyl]-2-(1,1,4-trioxo-1,2,5-thiadiazolidin-2-yl)-phenyl ester;
Benzoic acid 5-(2-methanesulfonylamino-3-methylbenzyl)-2-(1,1,4-trioxo-1,2,5-thiadiazolidin-2-yl)-phenyl ester;
2-Methylbenzoic acid 5-(2-methanesulfonyloxy-5-methylbenzyl)-2-(1,1,4-trioxo-1,2,5-thiadiazolidin-2-yl)-phenyl ester; and
5-(4-Benzyl-2-hydroxy-6-methylphenyl)-1,1-dioxo-1,2,5-thiadiazolidin-3-one;
or a pharmaceutically acceptable salt thereof.

The compounds of the invention depending on the nature of the substituents, may possess one or more asymmetric centers. The resulting diastereoisomers, enantiomers and geometric isomers are encompassed by the instant invention.

Compounds of formula (I) may be prepared starting, e.g., by cyclizing compounds of the formula

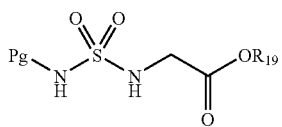
(II)

wherein Pg is an appropriate N-protecting group such as 4-methoxybenzyl, 2,4-dimethoxybenzyl or 2-trimethylsilylethyl, and $R_{19}$ is hydrogen to afford compounds of the formula

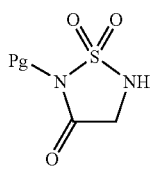
(III)

wherein Pg has a meaning as defined herein above, by treatment with a coupling agent such as diisopropyl carbodiimide (DIC) or 1-ethyl-3-(3-dimethylaminopropyl)carbodiimide hydrochloride (EDCI) in the presence a base such as triethylamine (TEA) or N-methyl-morpholine (NMM) in an organic solvent such as tetrahydrofuran (THF), N,N-dimethyl-formamide (DMF) or dichloromethane (DCM). The reaction may be carried out in the presence of an additive such as of hydroxybenzotriazole (HOBt).

Compounds of formula (II) wherein $R_{19}$ is hydrogen may be obtained from compounds of formula (II) wherein $R_{19}$ is an alkyl group according to methods well known in the art, e.g. compounds of formula (II) in which $R_{19}$ is methyl or ethyl can be treated with an aqueous base such as sodium or potassium hydroxide in an organic solvent such as THF, 1,4-dioxane, methanol (MeOH) or ethanol (EtOH) to afford compounds of formula (II) wherein $R_{19}$ is hydrogen, or compounds of formula (II) in which $R_{19}$ is t-butyl may be treated with an acid such as hydrochloric acid (HCl) or trifluoroacetic acid (TFA) in an organic solvent such as DCM or ethyl acetate (EtOAc) to afford compounds of formula (II) wherein $R_{19}$ is hydrogen.

Compounds of formula (II) wherein $R_{19}$ is an alkyl group such as methyl, ethyl or t-butyl, and the like, may be obtained analogously to a literature procedure described by Ducry et al. in Helvetica Chimica Acta, 1999, 82, 2432.

Resulting compounds of formula (III) wherein Pg has a meaning as defined herein can then be coupled with a variety of boronic acid derivatives of the formula

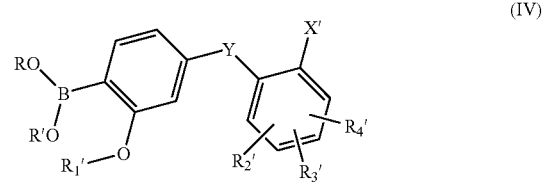
(IV)

wherein Y has a meaning as defined herein above, and $R_1'$, $R_2'$, $R_3'$, $R_4'$ and X' have meanings as defined herein for $R_1$, $R_2$, $R_3$, $R_4$ and X, or $R_1'$, $R_2'$, $R_3'$, $R_4'$ and X' are groups convertible to $R_1$, $R_2$, $R_3$, $R_4$ and X, respectively, and R and R' are hydrogen or lower alkyl, or R and R' combined are alkylene which together with the boron and the oxygen atoms form a 5- or 6-membered ring, in the presence of a copper catalyst such as copper (II) acetate and a base such as cesium (II) carbonate ($Cs_2CO_3$) or TEA in an organic solvent such as THF, 1,4-dioxane or DCM to form compounds of the formula

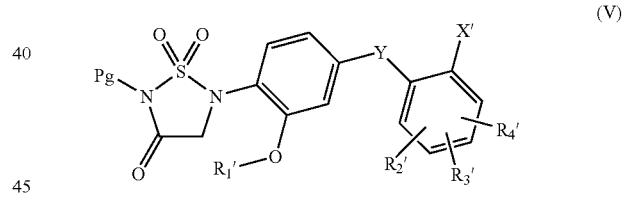
(V)

wherein Y and Pg have meanings as defined herein above, and $R_1'$, $R_2'$, $R_3'$, $R_4'$ and X' have meanings as defined herein for $R_1$, $R_2$, $R_3$, $R_4$ and X, or $R_1'$, $R_2'$, $R_3'$, $R_4'$ and X' are groups convertible to $R_1$, $R_2$, $R_3$, $R_4$ and X, respectively. Alternatively, compounds of formula (III) may be coupled with a boroxine derivative corresponding to a boronic acid derivative of formula (IV) as described, e.g., by Chan et al. in Tet. Lett. 2003, 44, 3863.

Compounds of formula (IV) are known, or if they are novel, they may be prepared using methods well known in the art, or as illustrated herein in the Examples, or modifications thereof.

Alternatively, compounds of formula (V) wherein Y and Pg have meanings as defined herein above, and $R_1'$, $R_2'$, $R_3'$, $R_4'$ and X' have meanings as defined herein for $R_1$, $R_2$, $R_3$, $R_4$ and X, or $R_1'$, $R_2'$, $R_3'$, $R_4'$ and X' are groups convertible to $R_1$, $R_2$, $R_3$, $R_4$ and X, respectively, may be obtained by reacting a compound of formula (III) wherein Pg has a meaning as defined herein with compounds of the formula

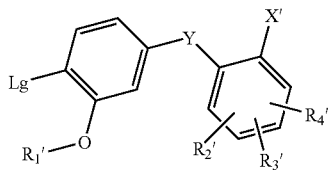

(VI)

wherein Y has a meaning as defined herein above, Lg represents a leaving group such as halide or trifluoromethanesulfonate, preferably fluoride or chloride, and $R_1'$, $R_2'$, $R_3'$, $R_4'$ and X' have meanings as defined herein for $R_1$, $R_2$, $R_3$, $R_4$ and X, or $R_1'$, $R_2'$, $R_3'$, $R_4'$ and X' are groups convertible to $R_1$, $R_2$, $R_3$, $R_4$ and X, respectively, using conditions well know in the art or using methods described herein or modifications thereof, e.g., a compound of formula (III) may be first treated with a base such as $Cs_2CO_3$, or sodium, lithium or potassium bis(trimethylsilyl) amide in an inert organic solvent such as THF or 1,4-dioxane followed by reaction with a compound of formula (VI) at a temperature ranging from room temperature (RT) to 110° C.

Compounds of formula (VI) are known, or if they are novel, they may be prepared using methods well known in the art, or as illustrated herein in the Examples, or modifications thereof.

Compounds of formula (V) wherein Y and Pg have meanings as defined herein above, and, $R_1'$, $R_2'$, $R_3'$, $R_4'$ and X' have meanings as defined herein for $R_1$, $R_2$, $R_3$, $R_4$ and X, or $R_1'$, $R_2'$, $R_3'$, $R_4'$ and X' are groups convertible to $R_1$, $R_2$, $R_3$, $R_4$ and X, respectively, can be converted to compounds of the formula

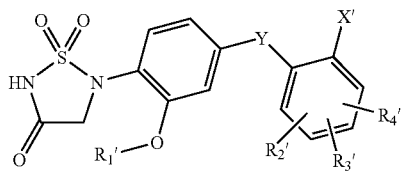

(I')

by removal of the N-protecting group according to methods well known in the art, e.g. in particular when Pg is 4-methoxybenzyl or 2,4-dimethoxybenzyl group using hydrogen in the presence of a catalyst such as palladium on carbon in a polar organic solvent such as MeOH or EtOAc, or by treatment with an acid such as TFA in an organic solvent such as DCM, preferably in the presence of an additive such as t-butyldimethylsilane or triethylsilane, or in particular when Pg is trimethylsilylethyl group using a fluoride reagent such as tetra-n-butylammoniumfluoride in an organic solvent such as THF or 1,4-dioxane.

In addition, compounds of formula (I') wherein Y has a meaning as defined herein above, and $R_1'$, $R_2'$, $R_3'$, $R_4'$ and X' have meanings as defined herein for $R_1$, $R_2$, $R_3$, $R_4$ and X, or $R_1'$, $R_2'$, $R_3'$, $R_4'$ and X' are groups convertible to $R_1$, $R_2$, $R_3$, $R_4$ and X, respectively, may be prepared by condensing compounds of the formula

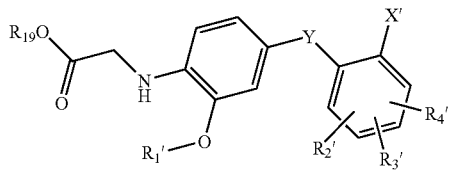

(VII)

wherein $R_{19}$ has a meaning as defined herein above, with sulfamoyl chloride analogs of the formula $ClS(O)_2NHR_{20}$ (VIII)

wherein $R_{20}$ is hydrogen or alkoxycarbonyl such as t-butoxycarbonyl or 2-trimethylsilyl-ethoxycarbonyl in the presence of a base such as TEA or NMM in an organic solvent such as acetonitrile (MeCN), DCM or THF to form compounds of the formula

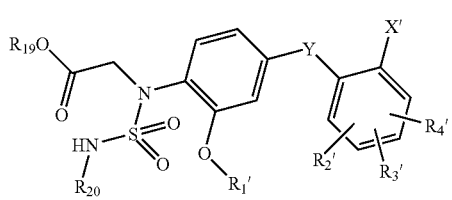

(IX)

wherein Y, $R_{19}$ and $R_{20}$ have meanings as defined herein above, and $R_1'$, $R_2'$, $R_3'$, $R_4'$ and X' have meanings as defined herein for $R_1$, $R_2$, $R_3$, $R_4$ and X, or $R_1'$, $R_2'$, $R_3'$, $R_4'$ and X' are groups convertible to $R_1$, $R_2$, $R_3$, $R_4$ and X, respectively.

Compounds of formula (VIII) wherein $R_{20}$ is alkoxycarbonyl may be obtained by reacting chlorosulfonyl isocyanate with the appropriate alcohol in an organic solvent such as MeCN, DCM or THF.

Compounds of formula (VII) may be prepared using methods well known in the art or according to methods described herein or modifications thereof, e.g., under conditions of reductive amination, or according to the method described by Tohru Fukuyama et al. in *Tet. Lett.*, 1997, 38 (33), 5831; or by reacting amines of the formula.

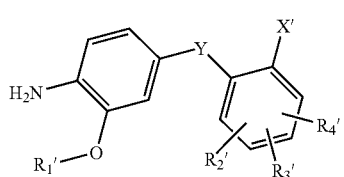

(X)

wherein Y has a meaning as defined herein above, and $R_1'$, $R_2'$, $R_3'$, $R_4'$ and X' have meanings as defined herein for $R_1$, $R_2$, $R_3$, $R_4$ and X, or $R_1'$, $R_2'$, $R_3'$, $R_4'$ and X' are groups convertible to $R_1$, $R_2$, $R_3$, $R_4$ and X, respectively, with an acetate of the formula $Lg'-CH_2-C(O)-O-R_{19}$ (XI)

wherein Lg' and $R_{19}$ have meanings as defined herein, in the presence of a base such as TEA or NMM in an inert solvent such as THF or 1,4-dioxane.

Amines of formula (X) are known, or if they are novel, they may be obtained according to methods well known in the art, or as described herein in the illustrative Examples, or using modifications thereof.

Compounds of formula (IX) wherein Y and $R_{19}$ have meanings as defined herein, and $R_1'$, $R_2'$, $R_3'$, $R_4'$ and $X'$ have meanings as defined herein for $R_1$, $R_2$, $R_3$, $R_4$ and X, or $R_1'$, $R_2'$, $R_3'$, $R_4'$ and $X'$ are groups convertible to $R_1$, $R_2$, $R_3$, $R_4$ and X, respectively, and $R_{20}$ is alkoxycarbonyl may be converted to compounds of formula (IX) wherein $R_{20}$ is hydrogen according to methods known in the art or using methods described herein or modifications thereof, e.g., compounds of formula (IX) wherein $R_{20}$ is t-butoxycarbonyl may be treated with an acid such as TFA, neat or in an extrinsic organic solvent such as DCM, or compounds of formula (IX) wherein $R_{20}$ is 2-trimethylsilylethoxycarbonyl may be treated with a fluoride reagent such as tetra-n-butylammoniumfluoride in an organic solvent such as THF or 1,4-dioxane to afford compounds of formula (IX) wherein $R_{20}$ is hydrogen.

Compounds of formula (IX) wherein Y and $R_{19}$ have meanings as defined herein, and $R_1'$, $R_2'$, $R_3'$, $R_4'$ and $X'$ have meanings as defined herein for $R_1$, $R_2$, $R_3$, $R_4$ and X, or $R_1'$, $R_2'$, $R_3'$, $R_4'$ and $X'$ are groups convertible to $R_1$, $R_2$, $R_3$, $R_4$ and X, respectively, and $R_{20}$ is hydrogen can be cyclized to form compounds of formula (I') using methods and conditions well known in the art or as illustrated with Examples herein or modifications thereof.

Alternatively, compounds of formula (IX) wherein Y and $R_{19}$ have meanings as defined herein, and $R_1'$, $R_2'$, $R_3'$, $R_4'$ and $X'$ have meanings as defined herein for $R_1$, $R_2$, $R_3$, $R_4$ and X, or $R_1'$, $R_2'$, $R_3'$, $R_4'$ and $X'$ are groups convertible to $R_1$, $R_2$, $R_3$, $R_4$ and X, respectively; and $R_{20}$ is hydrogen, may be obtained by first condensing amines of formula (X) with sulfamide in an aqueous solution and in the presence of a base such as sodium bicarbonate ($NaHCO_3$) at an elevated temperature, preferably at the boiling point of the solution, to afford compounds of the formula

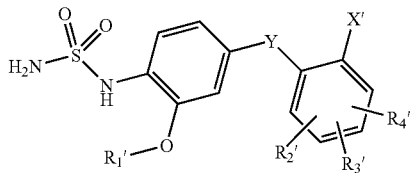

(XII)

wherein Y has a meaning as defined herein above, and $R_1'$, $R_2'$, $R_3'$, $R_4'$ and $X'$ have meanings as defined herein for $R_1$, $R_2$, $R_3$, $R_4$ and X, or $R_1'$, $R_2'$, $R_3'$, $R_4'$ and $X'$ are groups convertible to $R_1$, $R_2$, $R_3$, $R_4$ and X, respectively. Compound of formula (XII) may then be converted to compound of formula (IX) in which $R_{20}$ is hydrogen by the reaction with acetates of formula (XI) in the presence of a base such as sodium hydride in an inert solvent such as THF or DMF.

In starting compounds and intermediates which are converted to the compounds of the invention in a manner described herein, functional groups present, such as amino, thiol, carboxyl, and hydroxy groups, are optionally protected by conventional protecting groups that are common in preparative organic chemistry. Protected amino, thiol, carboxyl, and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well known protecting groups that meet these conditions and their introduction and removal are described, for example, in McOmie, "*Protective Groups in Organic Chemistry*", Plenum Press, London, N.Y. (1973); and Greene and Wuts, "*Protective Groups in Organic Synthesis*", John Wiley and Sons, Inc, New York (1999).

The above mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, optical isomers (enantiomers, antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. The carboxylic acid intermediates can thus be resolved into their optical antipodes e.g. by fractional crystallization of D- or L-(alpha-methylbenzylamine, cinchonidine, cinchonine, quinine, quinidine, ephedrine, dehydroabietylamine, brucine or strychnine)-salts. Racemic products can also be resolved by chiral chromatography, e.g. high pressure liquid chromatography using a chiral adsorbent.

Finally, compounds of the invention are either obtained in the free form, as a salt thereof if salt forming groups are present or as prodrug derivatives thereof.

In particular, the NH-group of the 1,1-dioxo-1,2,5-thiadiazolidin-3-one moiety, may be converted into salts with pharmaceutically acceptable bases. Salts may be formed using conventional methods, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_{1-4}$)alkanecarboxylic acids which, for example, are unsubstituted or substituted by halogen, for example acetic acid, such as saturated or unsaturated dicarboxylic acids, for example oxalic, succinic, maleic or fumaric acid, such as hydroxy-carboxylic acids, for example glycolic, lactic, malic, tartaric or citric acid, such as amino acids, for example aspartic or glutamic acid, or with organic sulfonic acids, such as ($C_{1-4}$)alkyl-sulfonic acids (for example methanesulfonic acid) or arylsulfonic acids which are unsubstituted or substituted (for example by halogen). Preferred are salts formed with hydrochloric acid, methanesulfonic acid and maleic acid.

Prodrug derivatives of any compound of the present invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

In view of the close relationship between the free compounds, the prodrug derivatives and the compounds in the form of their salts, whenever a compound is referred to in this context, a prodrug-derivative and a corresponding salt is also intended, provided such is possible or appropriate under the circumstances.

The compounds, including their salts, can also be obtained in the form of their hydrates, or include other solvents used for their crystallization.

As described herein above, the compounds of the present invention are inhibitors of PTPases and, thus, may be employed for the treatment of conditions mediated by the PTPases. Accordingly, the compounds of formula (I) may be employed for treatment of insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

The present invention further provides pharmaceutical compositions comprising a therapeutically effective amount of a pharmacologically active compound of the instant invention, alone or in combination with one or more pharmaceutically acceptable carriers.

The pharmaceutical compositions according to the invention are those suitable for enteral, such as oral or rectal; transdermal and parenteral administration to mammals, including man, for the treatment of conditions mediated by PTPase activity, in particular, PTP-1B and TC PTP activity. Such conditions include insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and or polyvinylpyrrolidone; if desired
d) disintegrants, e.g., starches, agar, alginic acid or its sodium salt, or effervescent mixtures; and/or
e) absorbants, colorants, flavors and sweeteners. Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Accordingly, the present invention provides pharmaceutical compositions as described above for the treatment of conditions mediated by PTPases, preferably, insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include:

a) anti-diabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; thiazolidone derivatives such as glitazones, e.g., pioglitazone and rosiglitazone; glucokinase activators; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; modulators of PPARs (peroxisome proliferator -activated receptors), e.g., non-glitazone type PPARγ agonists such as N-(2-benzoylphenyl) -L-tyrosine analogues, e.g. GI-262570, and JTT501; DPPIV (dipeptidyl peptidase IV) inhibitors such as LAF237, MK-0431, saxagliptin and GSK23A; SCD-1 (stearoyl-CoA desaturase-1) inhibitors; DGAT1 and DGAT2 (diacylglycerol acyltransferase 1 and 2) inhibitors; ACC2 (acetyl CoA carboxylase 2) inhibitors; and breakers of AGE (advanced glycation end products);

b) anti-dyslipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; HDL increasing compounds such as cholesterol ester transfer protein (CETP) inhibitors, e.g., JTT705; Apo-A1 analogs and mimetics; squalene synthase inhibitors; FXR (farnesoid X receptor) and LXR (liver X receptor) ligands; cholestyramine; fibrates; nicotinic acid; and aspirin;

c) anti-obesity agents such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine, ecopipam, ephedrine, and pseudoephedrine; cholesterol absorption modulators such as ZETIA® and KT6-971; and cannabinoid receptor antagonists such as rimonabant; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists such as eplerenone; and aldosterone synthase inhibitors such as anastrazole and fadrazole.

Other specific anti-diabetic compounds are described by Patel Mona in *Expert Opin Investig Drugs,* 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents or anti-hypertensive agents, most preferably from antidiabetics or anti-obesity agents as described above.

The present invention further relates to pharmaceutical compositions as described above for use as a medicament.

The present invention further relates to use of pharmaceutical compositions or combinations as described above for the preparation of a medicament for the treatment of conditions mediated by PTPase activity, in particular, PTP-1B and TC PTP activity. Such conditions include insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

Thus, the present invention also relates to a compound of formula (I) for use as a medicament, to the use of a compound of formula (I) for the preparation of a pharmaceutical composition for treatment of conditions mediated by PTPase activity, in particular, PTP-1B and TC PTP activity, and to a pharmaceutical composition for use in conditions mediated by PTPase activity, in particular, PTP-1B and TC PTP activity, comprising a compound of formula (I), or a pharmaceutically acceptable salt thereof, in association with a pharmaceutically acceptable diluent or carrier therefore.

The present invention further provides a method for the treatment of conditions mediated by PTPase activity, in particular, PTP-1B and TC PTP activity, which method comprises administering a therapeutically effective amount of a compound of the present invention.

A unit dosage for a mammal of about 50 to 70 kg may contain between about 1 mg and 1000 mg, advantageously between about 5 mg to 500 mg of the active ingredient. The therapeutically effective dosage of a compound of formula I is dependent on the species of warm-blooded animal (mammal), the body weight, age and individual condition, on the form of administration, and on the compound involved.

In accordance with the foregoing the present invention also provides a therapeutic combination, e.g., a kit, kit of parts, e.g., for use in any method as defined herein, comprising a compound of formula (I), or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents or anti-hypertensive agents. The kit may comprise instructions for its administration.

Similarly, the present invention provides a kit of parts comprising: (i) a pharmaceutical composition of the invention; and (ii) a pharmaceutical composition comprising a compound selected from an anti-diabetic, a hypolipidemic agent, an anti-obesity agent, an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula (I), or a pharmaceutically acceptable salt thereof, and a second drug substance, said second drug substance being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to modulation of PTPase activity, in particular, PTP-1B and TC PTP activity.

Preferably, the condition associated with PTPase activity, in particular, PTP-1B and TC PTP activity, is selected from insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

Finally, the present invention provides a method or use which comprises administering a compound of formula (I) in combination with a therapeutically effective amount of an anti-diabetic agent, a hypolipidemic agent, an anti-obesity agent or an anti-hypertensive agent.

Ultimately, the present invention provides a method or use which comprises administering a compound of formula (I) in the form of a pharmaceutical composition as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests, using advantageously mammals, e.g., mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-3}$ molar and $10^{-11}$ molar concentrations or between about $10^{-3}$ molar and $10^{-10}$ molar concentrations. A therapeutically effective amount in vivo may range depending on the route of administration, between about 0.1 and 500 mg/kg or between about 1 and 500 mg/kg, preferably between about 5 and 100 mg/kg.

The activity of a compound according to the invention may be assessed by the following methods or by following methods well described in the art (e.g. Peters G. et al. *J. Biol. Chem,* 2000, 275, 18201-09).

For example, the PTP-1B inhibitory activity in vitro may be determined as follows:

Assessment of human PTP-1B (hPTP-1B) activity in the presence of various agents is determined by measuring the amount of inorganic phosphate released from a phosphopeptide substrate using a 96-well microtiter plate format. The assay (100 μL) is performed in an assay buffer comprised of 50 mM TRIS (pH 7.5), 50 mM NaCl, 3 mM DTT at ambient temperature. The assay is typically performed in the presence of 0.4% dimethyl sulfoxide (DMSO). However, concentrations as high as 10% are used with certain poorly soluble compounds. A typical reaction is initiated by the addition of 0.4 pmoles of hPTP-1B (amino acids 1-411) to wells containing assay buffer, 3 nmoles of the synthetic phosphopeptide substrate (GNGDp YMPMSPKS), and the test compound. After 10 min, 180 μL malachite green reagent (0.88 mM malachite green, 8.2 mM ammonium molybdate, aqueous 1 N HCl, and 0.01% Triton X-100) is added to terminate the reaction. Inorganic phosphate, a product of the enzyme reaction, is quantitiated after 15 min as the green color resulting from complexing with the Malichite reagent and is determined as an $A_{620}$ using a Molecular Devices (Sunnyvale, Calif.) SpectraMAX Plus spectrophotometer. Test compounds are solubilized in 100% DMSO (Sigma, D-8779) and diluted in DMSO. Activity is defined as the net change in absorbance resulting from the activity of the uninhibited $hPTP-1B_{[1-411]}$ minus that of a tube with acid-inactivated $hPTP-1B_{[1-411]}$.

The $hPTP-1B_{[1-411]}$ is cloned by PCR from a human hippocampal cDNA library (Clonetech) and inserted into a pET 19-b vector (Novagen) at the Nco1 restriction site. *E. coli* strain BL21 (DE3) is transformed with this clone and stored as a stock culture in 20% glycerol at −80° C. For enzyme production, a stock culture is inoculated into Lb/Amp and grown at 37° C. Expression of PTP-1B is initiated by induction with 1 mM IPTG after the culture had reached an $OD_{600}$=0.6. After 4 h, the bacterial pellet is collected by centrifugation. Cells are resuspended in 70 mL lysis buffer (50 mM Tris, 100 mM NaCl, 5 mM DTT, 0.1% Triton X-100, pH7.6), incubated on ice for 30 min then sonicated (4×10 sec bursts at full power). The lysate is centrifuged at 100,000×g for 60 min and the supernatant is buffer exchanged and purified on a cation exchange POROS 20SP column followed by an anion exchange Source 30Q (Pharmacia) column, using linear NaCl gradient elutions. Enzyme is pooled, adjusted to 1 mg/mL and frozen at −80° C.

Alternatively, the assessment of human PTP-1B activity in the presence of various agents may be determined by measuring the hydrolysis products of known competing substrates. For example, cleavage of substrate para-nitrophenylphosphate (pNPP) results in the release of the yellow-colored para-nitrophenol (pNP) which can be monitored in real time using a spectrophotometer. Likewise, the hydrolysis of the fluorogenic substrate 6,8-difluoro-4-methylumbelliferyl phosphate ammonium salt (DiFMUP) results in the release of the fluorescent DiFMU which can be readily followed in a continuous mode with a fluorescence reader (Anal. Biochem. 273, 41, 1999; Anal. Biochem. 338, 32, 2005):

pNPP Assay

Compounds were incubated with 1 nM recombinant human PTP-1B$_{[1-298]}$ or PTP-1B$_{[1-322]}$ in buffer (50 mM Hepes, pH 7.0, 50 mM KCl, 1 mM EDTA, 3 mM DTT, 0.05% NP-40 for 5 min at room temperature. The reaction is initiated by the addition of pNPP (2 mM final concentration) and run for 120 min at room temperature. Reactions are quenched with 5 N NaOH. Absorbance at 405 nm is measured using any standard 384 well plate reader.

DiFMUP Assay

Compounds are incubated with 1 nM recombinant human PTP-1B$_{[1-298]}$ or PTP-1B$_{[1-322]}$ in buffer (50 mM Hepes, pH 7.0, 50 mM KCl, 1 mM EDTA, 3 mM DTT, 0.05% NP-40 (or 0.001% BSA) for 5 min at room temperature. The reaction is initiated by the addition of DiFMUP (6 µM final concentration) and run kinetically on fluorescence plate reader at 355 nm excitation and 460 nm emission wavelengths. Reaction rates over 15 min are used to calculate inhibition.

PTP-1B$_{[1-298]}$ is expressed in *E. coli* BL21 (DE3) containing plasmids constructed using pET19b vectors (Novagen). The bacteria is grown in minimal media using an "On Demand" Fed-batch strategy. Typically, a 5.5 liter fermentation is initiated in Fed-batch mode and grown overnight unattended at 37° C. Optical densities varied between 20-24 OD$_{600}$ and the cultures are induced at 30° C. with IPTG to a final concentration of 0.5 mM. The bacterial cells are harvested 8 hours later and yield 200-350 gm (wet weight). The cells are frozen as pellets and stored at –80° C. until use. All steps are performed at 4° C. unless noted. Cells (~15 g) are thawed briefly at 37° C. and resuspended in 50 mL of lysis buffer containing 50 mM Tris-HCl, 150 mM NaCl, 5 mM DTT, pH 8.0 containing one tablet of Complete (EDTA-free) protease cocktail (Boehringer Mannheim), 100 µM PMSF and 100 µg/mL DNase I. The cells are lysed by sonication (4×10 second burst, full power) using a Virsonic 60 (Virtus). The pellet is collected at 35,000×g, resuspended in 25 mL of lysis buffer using a Polytron and collected as before. The two supernatants are combined and centrifuged for 30 min at 100,000×g. The soluble lysate could be stored at this stage at –80° C. or used for further purification. Diafiltration using a 10 kD MWCO membrane is used to buffer exchange the protein and reduce the NaCl concentration prior to cation exchange chromatography. Diafiltration buffer contained 50 mM MES, 75 mM NaCl, 5 mM DTT, pH 6.5. Soluble supernatant is then loaded onto a POROS 20 SP (1×10 cm) column equilibrated with cation exchange buffer (50 mM MES and 75 mM NaCl, pH 6.5) at a rate of 20 mL/min. An analytical column (4.6×100 mm) is run in a similar fashion except the flow rate was reduced to 10 mL/min. Protein is eluted from the column using a linear salt gradient (75-500 mm NaCl in 25 CV). Fractions containing PTP-1B$_{[1-298]}$ are identified and pooled according to SDS-PAGE analyses. Final purification is performed using Sephacryl S-100 HR (Pharmacia). The column (2.6×35 cm) is equilibrated with 50 mM HEPES, 100 mM NaCl, 3 mM DTT, pH 7.5 and run at a flow rate of 2 mL/min. The final protein is pooled and concentrated to ~5 mg/mL using an Ultrafree-15 concentrator (Millipore) with a MWCO 10,000. The concentrated protein is stored at –80° C. until use.

Competitive binding to the active site of the enzyme can be determined as follows:

Ligand binding is detected by acquiring $^1$H-$^{15}$N HSQC spectra on 250 µL of 0.15 mM PTP-1B$_{[1-298]}$ in the presence and absence of added compound (1-2 mM). The binding is determined by the observation of $^{15}$N- or $^1$H-amide chemical shift changes in two dimensional HSQC spectra upon the addition of a compound to $^{15}$N-label protein. Because of the $^{15}$N spectral editing, no signal from the ligand is observed, only protein signals. Thus, binding can be detected at high compound concentrations. Compounds which caused a pattern of chemical shift changes similar to the changes seen with known active site binders are considered positive.

All proteins are expressed in *E. coli* BL21 (DE3) containing plasmids constructed using pET19b vectors (Novagen). Uniformly $^{15}$N-labeled PTP-1B$_{1-298}$ is produced by growth of bacteria on minimal media containing $^{15}$N-labeled ammonium chloride. All purification steps are performed at 4° C. Cells (~15 g) are thawed briefly at 37° C. and resuspended in 50 mL of lysis buffer containing 50 mM Tris-HCl, 150 mM NaCl, 5 mM DTT, pH 8.0 containing one tablet of Complete (EDTA-free) protease cocktail (Boehringer Mannheim), 100 µM PMSF and 100 µg/mL DNase I. The cells are lysed by sonication. The pellet is collected at 35,000×g, resuspended in 25 mL of lysis buffer using a Polytron and collected as before. The two supernatants are combined and centrifuged for 30 min at 100,000×g. Diafiltration using a 10 kD MWCO membrane is used to buffer exchange the protein and reduce the NaCl concentration prior to cation exchange chromatography. Diafiltration buffer contained 50 mM MES, 75 mM NaCl, 5 mM DTT, pH 6.5. Soluble supernatant is then loaded onto a POROS 20 SP (1×10 cm) column equilibrated with cation exchange buffer (50 mM MES and 75 mM NaCl, pH 6.5) at a rate of 20 mL/min. Protein is eluted from the column using a linear salt gradient (75-500 mM NaCl in 25 CV). Fractions containing PTP-1B's are identified and pooled according to SDS-PAGE analyses. PTP-1B$_{1-298}$ is further purified by anion exchange chromatography using a POROS 20 HQ column (1×10 cm). The pool from cation exchange chromatography is concentrated and buffer exchanged in 50 mM Tris-HCl, pH 7.5 containing 75 mM NaCl and 5 mM DTT. Protein is loaded onto column at 20 mL/min and eluted using a linear NaCl gradient (75-500 mM in 25 CV). Final purification is performed using Sephacryl S-100 HR (Pharmacia) (50 mM HEPES, 100 mM NaCl, 3 mM DTT, pH 7.5). The NMR samples are composed of uniformly $^{15}$N-labeled PTP-1B$_{1-298}$ (0.15 mM) and inhibitor (1-2 mM) in a 10% D$_2$O/90% H$_2$O Bis-Tris -d$_{19}$ buffer (50 mM, pH=6.5) solution containing NaCl (50 mM), DL-1,4-Dithiothreitol-d$_{10}$ (5 mM) and Sodium azide (0.02%).

The $^1$H-$^{15}$N HSQC NMR spectra are recorded at 20° C., on Bruker DRX500 or DMX600 NMR spectrometers. In all. NMR experiments, pulsed field gradients are applied to afford the suppression of solvent signal. Quadrature detection in the indirectly detected dimensions is accomplished by using the States-TPPI method. The data are processed using Bruker software and analyzed using NMRCompass software (MSI) on Silicon Graphics computers.

The glucose and insulin lowering activity in vivo may be evaluated as follows:

Adult male C57BL ob/ob mice (Jackson Lab, Bar Harbor, Me.) at the age of 11 weeks are housed six per cage in a reversed light cycle room (light on from 6:00 p.m. to 6:00 a.m.) and given access to Purina rodent chow and water ad libitum. On day 1 tail blood samples are taken at 8:00 am and plasma glucose levels are determined. The animals are randomly assigned to the control and compound groups. The means of plasma glucose values of the groups are matched. Animals are then orally dosed with vehicle (0.5% carboxymethyl -cellulose with 0.2% Tween-80) or compounds (at 30 mg/kg) in vehicle. The mice are dosed daily for a total of 3 days. On day 4 basal blood samples are taken. The plasma samples are analyzed for glucose concentrations using a YSI2700 Dual Channel Biochemistry Analyzer (Yellow Springs Instrument Co., Yellow Springs, Ohio) and insulin concentrations using an ELISA assay.

The following Examples are intended to illustrate the invention and are not to be construed as being limitations thereon. Temperatures are given in degrees Centigrade (° C.). If not mentioned otherwise, all evaporations are performed under reduced pressure, preferably between about 15 and 100 mmHg (=20-133 mbar). The structure of final products, intermediates and starting materials is confirmed by standard analytical methods, e.g. microanalysis, melting point (mp) and spectroscopic characteristics (e.g. MS, IR, NMR). In general, abbreviations used are those conventional in the art.

HPLC Methods

Method A: 4.6 mm×5 cm C-8 reverse phase column, 3 µM particle size running a gradient of 10-90% MeCN/water (5 mM ammonium bicarbonate) over a period of 2 min at a flow rate of 4 mL/min at 50° C. (3 µL injection). DAD-UV detection, 220-600 nm.

EXAMPLE 1

5-(4-Benzyl-2-hydroxyphenyl)-1,1-dioxo-1,2,5-thiadiazolidin-3-one

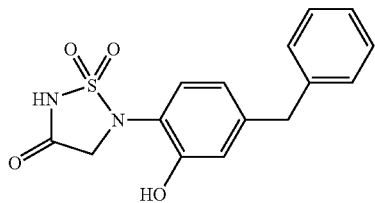

A. 2-Benzyloxy-4-iodo-1-nitrobenzene

To a solution of 5-iodo-2-nitrophenol (2.65 g, 10 mmol) [*J Org Chem*, Vol. 63, pp. 4199-4208 (1998)] in DMF (10 mL) is added benzyl bromide (1.71 g, 10 mmol) and $K_2CO_3$ (2.07 g, 15 mmol) and the mixture is heated at 65° C. for 30 min. Then water is added (400 mL) and it is extracted by EtOAc (2×200 mL). The water layer is then acidified and extracted with EtOAc (100 mL). The combined EtOAc layer is then washed with 1N HCl and brine, dried with $NaSO_4$ and concentrated to give the title compound as a yellow solid.

B. 2-Benzyloxy-4-iodophenylamine

To a mixture of 2-benzyloxy-4-iodo-1-nitrobenzene (2.35 g, 6.62 mmol) and Fe (1.85 g, 33.1 mmol) is added AcOH (24 mL) and EtOH (12 mL) and it is refluxed at 100° C. for 1.5 h. The mixture is then cooled and filtered through Celite. EtOAc (300 mL) is added and it is then washed with saturated $NaHCO_3$ (2×), brine (1×) and dried with $NaSO_4$. It is then concentrated and the residue is purified by column chromatography to give the title compound.

C. (2-Benzyloxy-4-iodophenylamino)-acetic acid tert-butyl ester

To a solution of 2-benzyloxy-4-iodophenylamine (2.35 g, 7.23 mmol) in DMF (15 mL) is added bromoacetic acid tert-butyl ester (1.76 g, 9.04 mmol) and $K_2CO_3$ (5.0 g, 36.2 mmol) and the mixture is heated at 50° C. for 4 h. 2N HCl solution (200 mL) is added with cooling and it is then extracted with EtOAc. The organic layer is then washed with brine, dried and concentrated. The residue is then purified by column chromatography to give the title compound as a white solid.

D. N-(t-Butoxycarbonylsulfamoyl)-N-(2-benzyloxy-4-iodophenyl)glycine tert-butyl ester To an ice cooled solution of chlorosulfonyl isocyanate (0.788 mL, 8.94 mmol) in DCM (40 mL) is added dropwise t-butanol (0.855 mL, 8.94 mmol). Then at 0° C., (2-benzyloxy-4-iodophenylamino)-acetic acid tert-butyl ester (2.62 g, 5.96 mmol) and triethylamine (2.08 mL, 14.9 mmol) in DCM-(40 mL) is added dropwise. After stirring for 30 min., DCM (300 mL) is added and the organic layer is washed with 2N HCl solution. It is then dried with $NaSO_4$, and concentrated. The residue is purified by column chromatography to give the title compound as an off-white foam.

E. t-Butyl N-[2-(benzyloxy)-4-iodophenyl]-N-({(tert-butoxycarbonyl)[2-(trimethylsilyl)ethyl]amino}sulfonyl)glycinate To a solution of N-(t-butoxycarbonylsulfamoyl)-N-(2-benzyloxy-4-iodophenyl)glycine tert-butyl ester (3.49 g, 5.6 mmol) in toluene (224 mL) is added triphenylphosphine (2.22 g, 8.47 mmol) and 2-trimethylsilanylethanol (992 mg, 8.38 mmol). DIAD (1.6 mL, 8.13 mmol) is then added dropwise over 10 min. After it is stirred for 50 min., toluene is remove under reduced pressure. After 18 h, 20% EtOAc/hexane is added (50 mL in 4 increments) to form a precipitate. The solid is filtered out and the filtrate is then concentrated. The residue is then purified by column chromatography to give the title compound as a white foam.

F. N-[2-(benzyloxy)-4-iodophenyl]-N-({[2-(trimethylsilyl)ethyl]amino}sulfonyl)glycine To a solution of above compound (3.11 g, 4.33 mmol) in DCM (20 mL) is added TFA (10 mL). The mixture is stirred at ambient temperature for 2 h and volatiles are evaporated to dryness. The residue is dissolved in toluene and re-evaporated. The residue is recrystallized from ether/hexane to give the title compound as a white solid, MS (M–H)⁻=561.

G. 5-(2-Benzyloxy-4-iodophenyl)-1,1-dioxo-2-(2-trimethylsilanylethyl)-1,2,5-thiadiazolidin-3-one To a solution of above compound (2.05 g, 3.64 mmol) in THF (20 mL) is added EDCI (1.05 g, 4.0 mmol) followed by HOBT (0.54 g, 4.0 mmol) and TEA (1.01 mL, 7.28 mmol). The mixture is then stirred at ambient temperature for 3 h, and the solvent is then evaporated. The residue is then partitioned between EtOAc and 1N HCl solution. The organic layer is washed with saturated $NaHCO_3$, dried with $MgSO_4$ and concentrated. The residue is purified by column chromatography to give the title compound as a clear oil.

H. Iodomethylbenzene

To a solution of sodium iodide (9.6 g, 64.0 mmol) in acetone (100 mL) is added benzyl bromide (10.4 g, 60 mmol). The mixture is stirred at reflux for 1 h. The mixture is cooled and concentrated. The residue is dissolved in MTBE, washed I. 5-(4-Benzyl-2-benzyloxyphenyl)-1,1-dioxo-2-(2-trimethylsilanylethyl)-1,2,5-thiadiazolidin-3-one Zinc dust (7.2 g) is placed in a 250 mL round bottom flask, placed under vacuum and heated with a heat gun for 5-8 min. The hot solid is allowed to cool slowly to ambient temperature. DMF (50 mL) is added, followed by 1,2-dibromoethane (0.8 mL). The mixture is placed under an atmosphere of $N_2$ and heated again until effervescence occurs and the reaction maintains itself. The mixture is cooled to ambient temperature and TMSCl (0.8 mL) is added and stirred for 30 min. Iodomethylbenzene (6.2 g, 28 mmol) is added and the mixture stirred for 30 min. at ambient temperature. The reaction is monitored by TLC until the starting material is converted to the ZnI, at which point $Pd_2 dba_3$ (0.8 g, 0.874 mmol) and P(o-tolyl)$_3$ (1.0 g, 3.28 mmol) are added. A solution of 5-(2-benzyloxy-4-iodophenyl)-1,1-dioxo-2-(2-trimethylsilanyl-ethyl)-1,2,5-thiadiazolidin-3-one (10.0 g, 18.3 mmol) in DMF is added slowly dropwise. The mixture is stirred at ambient temperature overnight. The reaction is diluted with EtOAc, filtered through Celite and washed with EtOAc. The organic mixture is washed with 100 mL of 1N HCl, 150 mL of saturated sodium chloride and dried over $MgSO_4$. The solution is then filtered through a plug of silica gel and concentrated to afford an orange oil. The oil is triturated with 4:1 hexane/ether. The crude material is chromatographed eluting with 4:1 hexane/EtOAc. The pure fractions are concentrated to an orange oil and hexane is added. The solution is filtered and washed with hexane to afford 5-(4-benzyl-2-benzyloxyphenyl)-1,1-dioxo-2-(2-trimethylsilanylethyl)-1,2,5-thiadiazolidin-3-one.

J. 5-(4-Benzyl-2-benzyloxyphenyl)-1,1-dioxo-1,2,5-thiadiazolidin-3-one

A mixture of 5-(4-benzyl-2-benzyloxyphenyl)-1,1-dioxo-2-(2-trimethylsilanylethyl)-1,2,5-thiadiazolidin-3-one (1.1 g, 2.16 mmol) and TBAF (1.0 M solution in THF, 4.0 mL, 4 mmol) is heated at 50° C. for 18 h. After THF is removed under reduced vacuum, $KHCO_3$ solution (0.50 M, 10 mL) is added, followed by water (10-15 mL). The residue is allowed to coat the glassware and the water is decanted. The residue is washed with water (2×), and ether (1×). The residue is treated with 1N HCl solution and is extracted with EtOAc. The organic layer is then washed with water, dried with $MgSO_4$ and concentrated to give the title compound as an orange oil.

K. 5-(4-Benzyl-2-hydroxyphenyl)-1,1-dioxo-1,2,5-thiadiazolidin-3-one potassium salt A mixture of 5-(4-benzyl-2-benzyloxyphenyl)-1,1-dioxo-1,2,5-thiadiazolidin-3-one (55 mg, 0.135 mmol), $KHCO_3$ (0.75 M, 0.18 mL), EtOH (0.5 mL), water (2 mL) and 10% Pd/C (50 mg) is stirred at ambient temperature under a $H_2$ balloon for 2 h. It is then filtered through Celite. The mixture is then washed with ether and lyophilized to give the title compound as a light beige solid, MS (M–H)$^-$=317.

EXAMPLE 2

The following compounds are prepared using appropriate starting materials and general methods described in Example 1, Steps H-K. Step H is omitted when the appropriated iodo starting material is available. Example 2-8 uses 2-methylbenzylzinc chloride in place of Zn dust, TMSCl and 1,2-dibromoethane.

| Example | Chemical Name | MS (m/z) |
| --- | --- | --- |
| 2-1 | 5-[2-Hydroxy-4-(3-hydroxybenzyl)-phenyl]-1,1-dioxo-1,2,5-thiadiazolidin-3-one | (M – H)$^-$ = 333 |
| 2-2 | 5-[2-Hydroxy-4-(3-methoxybenzyl)-phenyl]-1,1-dioxo-1,2,5-thiadiazolidin-3-one | (M – H)$^-$ = 347 |
| 2-3 | 5-[4-(2-Fluoro-3-trifluoromethylbenzyl)-2-hydroxyphenyl]-1,1-dioxo-1,2,5-thiadiazolidin-3-one | (M – H)$^-$ = 403 |
| 2-4 | 2-[3-Hydroxy-4-(1,1,4-trioxo-1,2,5-thiadiazolidin-2-yl)-benzyl]-benzonitrile | (M – H)$^-$ = 342 |
| 2-5 | 5-[4-(2-Fluorobenzyl)-2-hydroxyphenyl]-1,1-dioxo-1,2,5-thiadiazolidin-3-one | (M – H)$^-$ = 335 |
| 2-6 | 5-(2-Hydroxy-4-naphthalen-2-ylmethylphenyl)-1,1-dioxo-1,2,5-thiadiazolidin-3-one | (M – H)$^-$ = 367 |
| 2-7 | 5-[2-Hydroxy-4-(3-trifluoromethylbenzylphenyl]-1,1-dioxo-1,2,5-thiadiazolidin-3-one | (M – H)$^-$ = 385 |
| 2-8 | 5-[2-Hydroxy-4-(2-methylbenzyl)phenyl]-1,1-dioxo-1,2,5-thiadiazolidin-3-one | (M – H)$^-$ = 331 |
| 2-9 | 5-[4-(4-Fluorobenzyl)-2-hydroxyphenyl]-1,1-dioxo-1,2,5-thiadiazolidin-3-one | (M – H)$^-$ = 335 |
| 2-10 | 3-[3-Hydroxy-4-(1,1,4-trioxo-1,2,5-thiadiazolidin-2-yl)-benzyl]-benzoic acid methyl ester | (M – H)$^-$ = 375 |
| 2-11 | 5-(4-Biphenyl-3-ylmethyl-2-hydroxyphenyl)-1,1-dioxo-1,2,5-thiadiazolidin-3-one | (M – H)$^-$ = 393 |
| 2-12 | 5-[4-(3-Fluoro-4-methylbenzyl)-2-hydroxyphenyl]-1,1-dioxo-1,2,5-thiadiazolidin-3-one | (M – H)$^-$ = 349 |
| 2-13 | 5-[2-Hydroxy-4-(4-methylbenzyl)phenyl]-1,1-dioxo-1,2,5-thiadiazolidin-3-one | (M – H)$^-$ = 331 |
| 2-14 | 5-[2-Hydroxy-4-(4-hydroxybenzyl)phenyl]-1,1-dioxo-1,2,5-thiadiazolidin-3-one | (M – H)$^-$ = 333 |
| 2-15 | 5-[4-(3-Fluorobenzyl)-2-hydroxyphenyl]-1,1-dioxo-1,2,5-thiadiazolidin-3-one | (M – H)$^-$ = 335 |
| 2-16 | 5-[4-(4-tert-Butylbenzyl)-2-hydroxyphenyl]-1,1-dioxo-1,2,5-thiadiazolidin-3-one | (M – H)$^-$ = 373 |

| Example | Chemical Name | MS (m/z) |
|---|---|---|
| 2-17 | 5-[4-{2-Benzenesulfonylmethylbenzyl)-2-hydroxyphenyl]-1,1-dioxo-1,2,5-thiadiazolidin-3-one | $(M-H)^- = 471$ |
| 2-18 | 5-[2-Hydroxy-4-(3-methylbenzyl)phenyl]-1,1-dioxo-1,2,5-thiadiazolidin-3-one | $(M-H)^- = 331$ |

EXAMPLE 3

{2-[3-Hydroxy-4-(1,1,4-trioxo-1,2,5-thiadiazolidin-2-yl)-benzyl]-phenyl}-carbamic acid tert-butyl ester

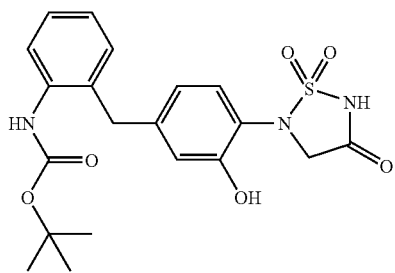

A. (2-Hydroxymethylphenyl)-carbamic acid tert-butyl ester

To a solution of (2-aminophenyl)-methanol (2.0 g, 16.2 mmol) in 20 mL THF is added di-tert-butyldicarbonate (4.26 g, 19.52 mmol). The mixture is stirred at 48° C. for 18 h. The mixture is diluted with EtOAc and washed with 0.2N ice cold HCl (1×), saturated NaCl (1×) and water (1×). The organic layer is dried over $MgSO_4$, filtered and concentrated. The crude material is purified by flash chromatography to acquire (2-hydroxymethylphenyl)-carbamic acid tert butyl ester.

B. (2-Iodomethylphenyl)-carbamic acid tert-butyl ester

To a solution of imidazole (2.6 g, 37 mmol) and $PPh_3$ (9.6 g, 37 mmol) in DCM (180 mL) is slowly added $I_2$ (9.4 g, 37 mmol) over a period of 10 min. The mixture is stirred at ambient temperature for 30 min. Then a solution of (2-hydroxymethylphenyl)-carbamic acid tert-butyl ester (7.5 g, 33.6 mmol) in DCM (40 mL) is added dropwise. The mixture is stirred at ambient temperature for 1 h, then is concentrated to about 70 mL and the resulting precipitate is filtered and washed with DCM. The filtrate is concentrated and purified to give the title compound as a solid.

C. (2-{3-Benzyloxy-4-[1,1,4-trioxo-5-(2-trimethylsilanylethyl)-1,2,5-thiadiazolidin-2-yl]-benzyl}-phenyl)-carbamic acid tert-butyl ester The title compound is prepared from (2-iodomethylphenyl)-carbamic acid tert-butyl ester analogously to Example 1, Step I.

D. {2-[3-Hydroxy-4-(1,1,4-trioxo-1,2,5-thiadiazolidin-2-yl)-benzyl]-phenyl}-carbamic acid tert-butyl ester The title compound is prepared from (2-{3-benzyloxy}-4-[1,1,4-trioxo-5-(2-trimethylsilanylethyl)-1,2,5-thiadiazolidin-2-yl]-benzyl}-phenyl)-carbamic acid tert-butyl ester analogously to Example 1, Steps J and K: MS $(M-H)^-=432$.

EXAMPLE 4

N-{2-[3-Hydroxy-4-(1,1,4-trioxo-1,2,5-thiadiazolidin-2-yl)-benzyl]-phenyl}-C-phenyl-methanesulfonamide

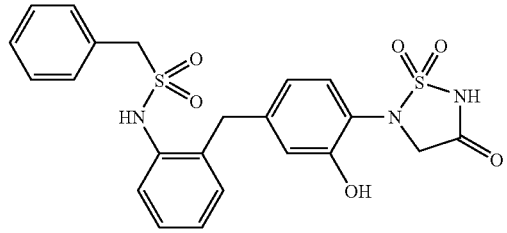

A. 5-[4-(2-Aminobenzyl)-2-benzyloxyphenyl]-1,1-dioxo-2-(2-trimethylsilanylethyl)-1,2,5-thiadiazolidin-3-one To a crude solution of (2-{3-benzyloxy}-4-[1,1,4-trioxo-5-(2-trimethylsilanylethyl)-1,2,5-thiadiazolidin-2-yl]-benzyl}-phenyl)-carbamic acid tert-butyl ester (4.0 g, 6.41 mmol) in DCM (15 mL) is added trifluoroacetic acid (7 mL, 93.9 mmol). The solution is stirred at ambient temperature for 1 h. The solvent is removed under reduced pressure, DCM is added and then evaporated (5×) to afford 5-[4-(2-aminobenzyl)-2-benzyloxyphenyl]-1,1-dioxo-2-(2-trimethylsilanylethyl)-1,2,5-thiadiazolidin-3-one.

B. N-(2-{3-Benzyloxy-4-[1,1,4-trioxo-5-(2-trimethylsilanylethyl)-1,2,5-thiadiazolidin-2-yl]-benzyl}-phenyl)-C-phenyl-methanesulfonamide To a solution of 5-[4-(2-aminobenzyl)-2-benzyloxyphenyl]-1,1-dioxo-2-(2-trimethylsilanylethyl)-1,2,5-thiadiazolidin-3-one (150 mg, 0.29 mmol) in pyridine (3 mL) is added α-tolylsulfonyl chloride (66 mg, 0.35 mmol) and the solution is stirred at ambient temperature for 1.5 h. The mixture is neutralized using 1N HCl solution, then diluted with EtOAc. The organic phase is washed with brine and water and is dried with $MgSO_4$, and concentrated. The residue is purified by flash column chromatography to give the title compound.

C. N-{2-[3-Hydroxy-4-(1,1,4-trioxo-1,2,5-thiadiazolidin-2-yl)-benzyl]-phenyl}-C-phenyl-methanesulfonamide The title compound is prepared analogously to Example 1, Steps J and K: MS $(M-H)^-=486$.

EXAMPLE 5

The following compounds are prepared using the general procedures outlined in Example 4.

| Example | Chemical Name | MS (m/z) |
|---|---|---|
| 5-1 | N-{2-[3-Hydroxy-4-(1,1,4-trioxo-1,2,5-thiadiazolidin-2-yl)-benzyl]-phenyl}-benzenesulfonamide | $(M-H)^- = 472$ |
| 5-2 | Ethanesulfonic acid {2-[3-hydroxy-4-(1,1,4-trioxo-1,2,5-thiadiazolidin-2-yl)-benzyl]-phenyl}-amide | $(M-H)^- = 424$ |
| 5-3 | Propane-1-sulfonic acid {2-[3-hydroxy-4-(1,1,4-trioxo-1,2,5-thiadiazolidin-2-yl)-benzyl]-phenyl}-amide | $(M-H)^- = 438$ |
| 5-4 | Butane-1-sulfonic acid {2-[3-hydroxy-4-(1,1,4-trioxo-1,2,5-thiadiazolidin-2-yl)-benzyl]-phenyl}-amide | $(M-H)^- = 452$ |
| 5-5 | C-Cyclohexyl-N-{2-[3-hydroxy-4-(1,1,4-trioxo-1,2,5-thiadiazolidin-2-yl)-benzyl]-phenyl}-methanesulfonamide | $(M-H)^- = 492$ |
| 5-6 | N-{2-[3-Hydroxy-4-(1,1,4-trioxo-1,2,5-thiadiazolidin-2-yl)-benzyl]-phenyl}-methanesulfonamide | $(M-H)^- = 410$ |
| 5-7 | N-{2-[3-Hydroxy-4-(1,1,4-trioxo-1,2,5-thiadiazolidin-2-yl)-benzyl]-phenyl}-4-isopropylbenzenesulfonamide | $(M-H)^- = 514$ |

EXAMPLE 6

N-{2-[3-Hydroxy-4-(1,1,4-trioxo-1,2,5-thiadiazolidin-2-yl)-benzyl]-phenyl}-aminosulfonamide

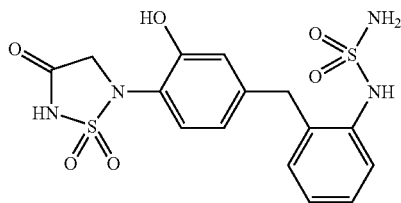

A. N-(2-{3-Benzyloxy-4-[1,1,4-trioxo-5-(2-trimethylsilanylethyl)-1,2,5-thiadiazolidin-2-yl]-benzyl}-phenyl)-sulfonamide tert-butyl ester N-(2-{3-Benzyloxy-4-[1,1,4-trioxo-5-(2-trimethylsilanylethyl)-1,2,5-thiadiazolidin-2-yl]-benzyl}-phenyl)-sulfonamide tert-butyl ester is prepared analogously to Example 1, Step D, starting with 5-[4-(2-aminobenzyl)-2-benzyloxyphenyl]-1,1-dioxo-2-(2-trimethylsilanylethyl)-1,2,5-thiadiazolidin-3-one (Example 4, Step A).

B. N-(2-{3-Benzyloxy-4-[1,1,4-trioxo-5-(2-trimethylsilanylethyl)-1,2,5-thiadiazolidin-2-yl]-benzyl}-phenyl)-aminosulfonamide N-(2-{3-Benzyloxy-4-[1,1,4-trioxo-5-(2-trimethylsilanylethyl)-1,2,5-thiadiazolidin-2-yl]-benzyl}-phenyl)-aminosulfonamide is prepared according to the general procedure outlined in Example 1, Step F.

C. N-{2-[3-Hydroxy-4-(1,1,4-trioxo-1,2,5-thiadiazolidin-2-yl)-benzyl]-phenyl}-aminosulfonamide N-{2-[3-Hydroxy-4-(1,1,4-trioxo-1,2,5-thiadiazolidin-2-yl)-benzyl]-phenyl}-aminosulfonamide is prepared analogously to Example 1, Steps J and K: MS $(M-H)^-=411$.

EXAMPLE 7

N-{3-[3-Hydroxy-4-(1,1,4-trioxo-1,2,5-thiadiazolidin-2-yl)-benzyl]-naphthalen-2-yl}-methanesulfonamide

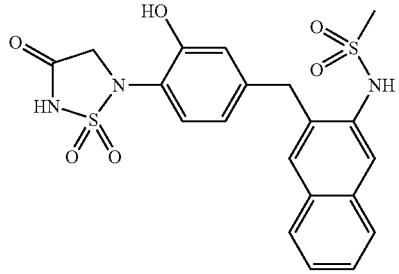

A. (3-Aminonaphthalen-2-yl)-methanol

To a solution of 3-amino-2-naphthoic acid (2 g, 10.7 mmol) in THF (11 mL) at 0° C. is added a 1 M solution of borane-tetrahydrofuran complex (27 mL) dropwise over 15 min. The mixture is allowed to warm to ambient temperature and stirred for 6 h. The excess borane-tetrahydrofuran complex is quenched by adding methanol at 0° C., and the solvent evaporated to obtain a yellow solid. The solid is washed with water, EtOAc and then dried under high vacuum to give (3-aminonaphthalen-2-yl)-methanol.

B. 5-[4-(3-Aminonaphthalen-2-ylmethyl)-2-benzy-
loxyphenyl]-1,1-dioxo-2-(2-trimethylsilanylethyl)-1,
2,5-thiadiazolidin-3-one The title compound is prepared analogously to Example 3, Steps A-C and Example 4, Step A from (3-aminonaphthalen-2-yl)-methanol.

C. N-{3-[3-Hydroxy-4-(1,1,4-trioxo-1,2,5-thiadiazo-
lidin-2-yl)-benzyl]-naphthalen-2-yl}-methane-
sulfonamide N-{3-[3-Hydroxy-4-(1,1,4-trioxo-1,2,5-thiadiazolidin-2-yl)-benzyl]-naphthalen-2-yl}-methanesulfonamide is prepared analogously to Example 4, Steps B and C, starting with 5-[4-(3-aminonaphthalen-2-ylmethyl)-2-benzyloxyphenyl]-1,1-dioxo-2-(2-trimethylsilanylethyl)-1,2,5-thiadiazolidin-3-one and methanesulfonyl chloride: MS (M−H)⁻=460.

EXAMPLE 8

N-{2-[3-Hydroxy-4-(1,1,4-trioxo-1,2,5-thiadiazoli-
din-2-yl)-benzyl]-phenyl}-acetamide

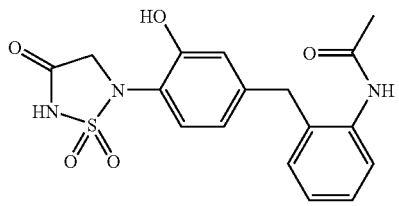

A. N-(2-{3-Benzyloxy-4-[1,1,4-trioxo-5-(2-trimeth-
ylsilanylethyl)-1,2,5-thiadiazolidin-2-yl]-benzyl}-
phenyl)-acetamide To a solution of 5-[4-(2-aminobenzyl)-2-benzyloxyphenyl]-1,1-dioxo-2-(2-trimethylsilanylethyl)-1,2,5-thiadiazolidin-3-one (Example 4, Step A) (250 mg, 0.478 mmol) in pyridine (1.5 mL) is added acetylchloride (41 mg, 0.525 mmol). The mixture is stirred at ambient temperature for 30 min., then diluted with EtOAc and washed with 0.5N HCl, saturated NaHCO₃ and brine. It is then dried over Na₂SO₄/MgSO₄, filtered and concentrated to afford N-(2-{3-benzyloxy-4-[1,1,4-trioxo-5-(2-trimethylsilanylethyl)-1,2,5-thiadiazolidin-2-yl]-benzyl}-phenyl)-acetamide as a gum: MS (M+H)⁺=566.1.

B. N-{2-[3-Hydroxy-4-(1,1,4-trioxo-1,2,5-thiadiazo-
lidin-2-yl)-benzyl]-phenyl}-acetamide N-{2-[3-Hydroxy-4-(1,1,4-trioxo-1,2,5-thiadiazolidin-2-yl)-benzyl]-phenyl}-acetamide is prepared according to the general procedures outlined in Example 1, Steps J and K: ¹H NMR (DMSO-d₆) δ 9.34, (br s, 1H), 7.36 (m, 1H), 7.23 (d, J=7.83 Hz, 1H), 7.16 (m, 1H), 7.11 (m, 2H), 6.67 (d, J=1.77 Hz, 1H), 6.63 (dd, J=8.0, 1.77 Hz, 1H).

EXAMPLE 9

The following compounds are prepared following the general procedures as outlined in Example 8.

| Example | Chemical Name | MS (m/z) |
| --- | --- | --- |
| 9-1 | 4-tert-Butyl-N-{2-[3-hydroxy-4-(1,1,4-trioxo-1,2,5-thiadiazolidin-2-yl)-benzyl]-phenyl}-benzamide | (M − H)⁻ = 492 |
| 9-2 | N-{2-[3-Hydroxy-4-(1,1,4-trioxo-1,2,5-thiadiazolidin-2-yl)-benzyl]-phenyl}-benzamide | (M − H)⁻ = 436 |

EXAMPLE 10

5-[4-(4-Ethylpyridin-2-ylmethyl)-2-hydroxyphenyl]-
1,1-dioxo-1,2,5-thiadiazolidin-3-one

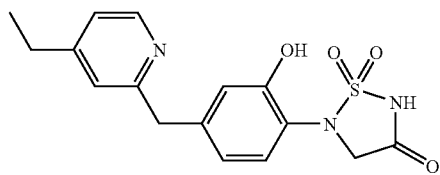

A. 5-(2-Benzyloxy-4-vinylphenyl)-1,1-dioxo-2-(2-
trimethylsilanylethyl)-1,2,5-thiadiazolidin-3-one To a solution of 5-(2-benzyloxy-4-iodophenyl)-1,1-dioxo-2-(2-trimethylsilanylethyl)-1,2,5-thiadiazolidin-3-one (2.24 g, 4.1 mmol) in acetonitrile (41 mL), in a pressure vessel, is added tributyl(vinyl)tin (1.43 mL, 4.9 mmol), Pd₂(dba)₃ (73 mg, 0.16 mmol), and tri-o-tolylphosphine. The vessel is sealed and the mixture is stirred at 80° C. for 18 h. The reaction is allowed to cool to ambient temperature, then stirred vigorously with saturated KF (10 mL) for 15 min. The mixture is filtered through Celite, washing several times with acetonitrile. The solvent is removed under reduced pressure and the crude residue is purified via silica gel chromatography using a gradient of 0-40% EtOAc/hexanes to afford 5-(2-benzyloxy-4-vinylphenyl)-1,1-dioxo-2-(2-trimethylsilanylethyl)-1,2,5-thiadiazolidin-3-one as a colorless oil: MS (M+NH₄)⁺=462.

B. 3-Benzyloxy-4-[1,1,4-trioxo-5-(2-trimethylsila-
nylethyl)-1,2,5-thiadiazolidin-2-yl]-benzaldehyde To a solution of 5-(2-benzyloxy-4-vinylphenyl)-1,1-dioxo-2-(2-trimethylsilanylethyl)-1,2,5-thiadiazolidin-3-one (1.9 g, 4.3 mmol) in 1:1:1 THF/t-BuOH/H₂O (60 mL) is added 1-methylmorpholine-N-oxide (551 mg, 4.74 mmol) and OsO₄ (2 mL of a 2.5 wt % solution in t-BuOH, 0.17 mmol). The reaction is stirred for 4 h at ambient temperature, then diluted with water (15 mL) and treated with NaIO₄ (4.5 g, 21.5 mmol) and NaHCO₃ (3.6 g, 43 mmol). The mixture is stirred vigorously for 1 h, then filtered through Celite. The solution is extracted with EtOAc. The organic phase is washed with saturated NaCl. The solution is dried over MgSO₄ and the solvent removed under reduced pressure, then purified via silica gel chromatography using a gradient of 0-40% EtOAc/hexanes to afford 3-benzyloxy-4-[1,1,4-trioxo-5-(2-trimethylsilanylethyl)-1,2,5-thiadiazolidin-2-yl]-benzaldehyde as a white solid: MS (M+NH₄)⁺=464.

C. 5-(2-Benzyloxy-4-hydroxymethylphenyl)-1,1-dioxo-2-(2-trimethylsilanylethyl)-1,2,5-thiadiazolidin-3-one To a solution of 3-benzyloxy-4-[1,1,4-trioxo-5-(2-trimethylsilanylethyl)-1,2,5-thiadiazolidin-2-yl]-benzaldehyde (1.6 g, 3.6 mmol) in benzene (20 mL), in a pressure vessel, is added triethylsilane (688 μL, 4.3 mmol) and (PPh$_3$)$_2$Re(O)$_2$I (63 mg, 0.072 mmol). The vessel is sealed and the reaction is stirred at 60° C. for 18 h. The mixture is allowed to cool to ambient temperature and the solvent is removed under reduced pressure. The crude triethylsilyl ether is immediately dissolved in MeOH (20 mL), treated with TFA (approximately 150 μL) and stirred for 1 h. The solvent is removed under reduced pressure and the crude alcohol is purified via silica gel chromatography using a gradient of 0-50% EtOAc/hexanes to afford of 5-(2-benzyloxy-4-hydroxymethylphenyl)-1,1-dioxo-2-(2-trimethylsilanylethyl)-1,2,5-thiadiazolidin-3-one as a light gray solid: MS (M+H)$^+$=466.

D. 5-(2-Benzyloxy-4-iodomethylphenyl)-1,1-dioxo-2-(2-trimethylsilanylethyl)-1,2,5-thiadiazolidin-3-one To slurry of resin-bound PPh$_3$ (850 mg, 2.5 mmol) in DCM (10 mL) at 0° C., in a pressure vessel, is added imidazole (200 mg, 2.8 mmol) and iodine (650 mg, 2.5 mmol). The mixture is vigorously stirred at 0° C. for 30 min. To the mixture is added a solution of 5-(2-benzyloxy-4-hydroxymethylphenyl)-1,1-dioxo-2-(2-trimethylsilanylethyl)-1,2,5-thiadiazolidin-3-one (550 mg, 1.2 mmol) in DCM (10 mL) dropwise. The vessel is sealed and heated to 45° C., with stirring, for 2 h. The reaction is allowed to cool to ambient temperature and the mixture is filtered through a plug of cotton to remove the resin. The organic solution is washed with saturated Na$_2$SO$_3$ and saturated NaCl, then dried over MgSO$_4$. The solvent is removed under reduced pressure to afford 5-(2-benzyloxy-4-iodomethylphenyl)-1,1-dioxo-2-(2-trimethylsilanylethyl)-1,2,5-thiadiazolidin-3-one as a white solid, which is used in the next step without further purification: MS (M+H)$^+$=576.

E. 5-[2-Benzyloxy-4-(4-ethylpyridin-2-ylmethyl)-phenyl]-1,1-dioxo-2-(2-trimethylsilanyl-ethyl)-1,2,5-thiadiazolidin-3-one In pressure vessels, zinc powder (2.145 g, 33 mmol) is dried by heating under vacuum, then cooled, placed under N$_2$, and slurried in N,N-dimethylacetamide (4 mL). To the slurry is added 1,2-dibromoethane (220 μL, 2.55 mmol) and the mixture is heated until boiling. The mixture is allowed to cool, and TMSCl (325 mL, 2.55 mmol) is added, followed by stirring for 30 min. to produce a green solution. To the slurry of activated zinc is added 5-(2-benzyloxy-4-iodomethylphenyl)-1,1-dioxo-2-(2-trimethylsilanylethyl)-1,2,5-thiadiazolidin-3-one (3.0 g, 5.37 mmol) in N,N-dimethylacetamide (5 mL) over 30 min. The organozinc solution is filtered and degassed with N$_2$, then to it is added Pd$_2$(dba)$_3$ (250 mg, 0.275 mmol) and 2-(di-t-butylphosphino)biphenyl (330 mg, 1.1 mmol), followed by degassed 2-bromo-4-ethylpyridine (1.20 g, 6.44 mmol) in N,N-dimethylacetamide. The vessels are sealed and the reaction heated in the microwave in 4 batches, 120° C. for 20 min. The reaction is allowed to cool to ambient temperature, then filtered through Celite. The resulting solutions are combined and diluted with EtOAc (150 mL) and washed with water and brine, then dried over MgSO$_4$. The solvent is removed under reduced pressure and the crude residue is purified via silica gel chromatography using a gradient of 0-75% EtOAc/hexanes to afford the title compound as a colorless oil: MS (M+H)$^+$=616.

F. 5-[2-Benzyloxy-4-(4-ethylpyridin-2-ylmethyl)-phenyl]-1,1-dioxo-1,2,5-thiadiazolidin-3-one To a solution of 5-[2-benzyloxy-4-(4-ethylpyridin-2-ylmethyl)-phenyl]-1,1-dioxo-2-(2-trimethylsilanyl-ethyl)-1,2,5-thiadiazolidin-3-one (47 mg, 0.088 mmol) in DMF (1 mL) is added CsF (80 mg, 0.53 mmol). The reaction is stirred at 60° C. for 2 h. The reaction is allowed to cool to ambient temperature and the solvent is evaporated under a stream of N$_2$. The crude residue is taken up in acetonitrile and filtered, washing with acetonitrile several times. The solvent is removed under reduced pressure and the crude cesium salt of 5-[2-benzyloxy-4-(6-benzyloxypyridin-2-ylmethyl)-phenyl]-1,1-dioxo-1,2,5-thiadiazolidin-3-one is used in the next step without further purification: MS (M+H)$^+$=516.

G. 5-[4-(4-Ethylpyridin-2-ylmethyl)-2-hydroxyphenyl]-1,1-dioxo-1,2,5-thiadiazolidin-3-one The title compound is prepared annalogously to Example 1, Step K: $^1$H NMR (MeOD) δ 8.27 (d, J=4.55, 1H), 7.32 (d, J=8.08 Hz, 1H), 7.12 (s, 1H), 7.09 (d, J=4.8 Hz, 1H), 6.74 (s, 1H), 6.70 (d, J=7.83 Hz, 1H), 4.26 (s, 2H), 3.99 (s, 2H), 2.61 (q, J=7.41 Hz, 2H), 1.19 (t, J=7.83 Hz, 3H); MS (M–H)$^-$=346.

EXAMPLE 11

5-[4-(6-Methoxypyridin-2-ylmethyl)-2-hydroxyphenyl]-1,1-dioxo-1,2,5-thiadiazolidin-3-one

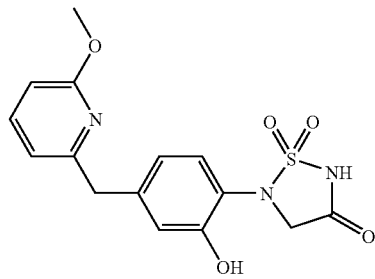

A. 5-[2-Benzyloxy-4-(6-methoxypyridin-2-ylmethyl)-phenyl]-1,1-dioxo-2-(2-trimethylsilanylethyl)-1,2,5-thiadiazolidin-3-one The title compound is prepared analogously to Example 10, Step A-E using 2-bromo-6-methoxypyridine in place of 2-benzyloxy-6-bromopyridine in Step E.

B. 5-[2-benzyloxy-4-(6-methoxypyridin-2-ylmethyl)-phenyl]-1,1-dioxo-1,2,5-thiadiazolidin-3-one The title compound is prepared analogously to Example 10, Step F.

C. 5-[4-(6-Methoxypyridin-2-ylmethyl)-2-hydroxyphenyl]-1,1-dioxo-1,2,5-thiadiazolidin-3-one To a solution of 5-[2-benzyloxy-4-(6-methoxypyridin-2-ylmethyl)-phenyl]-1,1-dioxo-1,2,5-thiadiazolidin-3-one (30 mg, 0.07 mmol) in DCM (10 mL) is added dropwise 1 M BBr$_3$ (110 µL, 0.11 mmol) in DCM. The reaction is quenched with water (1 mL) and excess 1 M KOH is added, followed by washing with Et$_2$O. The aqueous layer is concentrated under reduced pressure and the crude residue purified by HPLC using a gradient of 10-100% acetonitrile/water to afford the TFA salt of 5-[4-(6-methoxypyridin-2-ylmethyl)-2-hydroxyphenyl]-1,1-dioxo-1,2,5-thiadiazolidin-3-one: MS (M–H)$^-$=348.

EXAMPLE 12

5-(2-Hydroxy-4-pyridin-2-ylmethylphenyl)-1,1-dioxo-1,2,5-thiadiazolidin-3-one

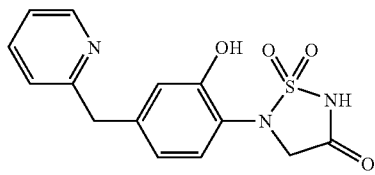

5-(2-Hydroxy-4-pyridin-2-ylmethylphenyl)-1,1-dioxo-1,2,5-thiadiazolidin-3-one is prepared according to the general procedure outlined in Example 10 using 2-bromopyridine in Step E: MS (M–H)$^-$=318; $^1$H NMR (MeOD) δ 8.39 (d, J=5.56 Hz, 1H), 7.70 (td, J=8, 4 Hz, 1H), 7.20 (m, 3H), 6.67 (d, J=2.0 Hz, 1H), 6.55 (dd, J=2.0, 8.0 Hz, 1H), 4.30 (s, 2H), 4.0 (s, 2H).

EXAMPLE 13

5-[2-Hydroxy-4-(2-methanesulfonylbenzyl)-phenyl]-1,1-dioxo-1,2,5-thiadiazolidin-3-one

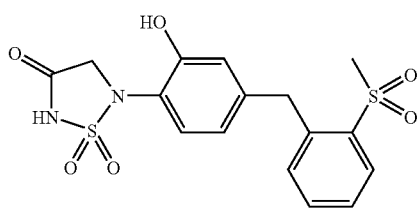

A. 2-Methylsulfanylbenzoic acid methyl ester

To a solution of methyl thiosalicylate (4.0 g, 23.8 mmol) in DMF (25 mL) is added K$_2$CO$_3$ (4.0 g, 28.94 mmol) followed by methyl iodide (2.3 mL, 36.9 mmol). The resulting mixture is stirred at ambient temperature for 1 h. The mixture is diluted with EtOAc and washed with 1N HCl (3×) and water (1×). The organic phase is dried over MgSO$_4$, filtered and concentrated to afford 2-methylsulfanylbenzoic acid methyl ester.

B. 2-Methanesulfonylbenzoic acid methyl ester

To a solution of 2-methylsulfanylbenzoic acid methyl ester (546 mg, 3 mmol) in dioxane (15 mL) is added MCPBA (25% in water, 4.12 g, 6 mmol) and the mixture is stirred at ambient temperature for 4 h. NaHCO$_3$ solution (15 mmol in 50 mL water) is added and the suspension is extracted with EtOAc (2×). The organic layer is washed with brine, dried with MgSO$_4$ and concentrated. The residue is purified by column chromatography to give the title compound.

C. (2-Methanesulfonylphenyl)-methanol

To a solution of 2-methanesulfonylbenzoic acid methyl ester (1.5 g, 7 mmol) in THF (20 mL) is added LiBH$_4$ (616 mg, 30 mmol) and the mixture is stirred at ambient temperature for 14 h. Additional LiBH$_4$ (310 mg, 15 mmol) is added and the mixture is heated at 65° C. for 45 min. Then under ice cooling, 1N HCl solution is added to quench the excess of LiBH$_4$ before EtOAc is added. The organic layer is washed with brine (2×) and water (1×), dried with MgSO$_4$, and concentrated to give the title compound.

D. 1-Iodomethyl-2-methanesulfonylbenzene

The title compound is prepared analogously to Example 3, Step B.

E. 5-[2-Hydroxy-4-(2-methanesulfonylbenzyl)-phenyl]-1,1-dioxo-1,2,5-thiadiazolidin-3-one 5-[2-Hydroxy-4-(2-methanesulfonylbenzyl)-phenyl]-1,1-dioxo-1,2,5-thiadiazolidin-3-one is prepared according to the general procedures outlined in Example 1, Steps I-K: (M–H)$^-$=395.

EXAMPLE 14

N-{2-[3-Hydroxy-4-(1,1,4-trioxo-1,2,5-thiadiazolidin-2-yl)-benzyl]-phenyl}-N-methylmethanesulfonamide

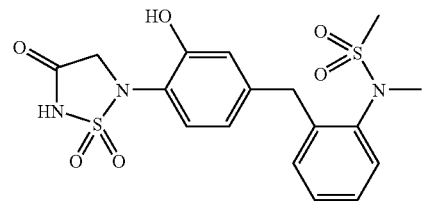

A. 2-Methanesulfonylaminobenzoic acid methyl ester

2-Methanesulfonylaminobenzoic acid methyl ester is prepared according to the general procedure outlined in Example 4, Step B, using 2-aminobenzoic acid methyl ester and methanesulfonyl chloride.

B. 2-(Methanesulfonylmethylamino)-benzoic acid methyl ester 2-(Methanesulfonylmethylamino)-benzoic acid methyl ester is prepared according to the general procedure outlined in Example 13, Step A.

C. N-(2-Hydroxymethylphenyl)-N-methyl-methanesulfonamide

N-(2-Hydroxymethylphenyl)-N-methylmethanesulfonamide is prepared according to the general procedure outlined in Example 13, Step C.

D. N-(2-Iodomethylphenyl)-N-methyl-methanesulfonamide

The title compound is prepared analogously to Example 3, Step B.

E. N-(2-[3-Hydroxy-4-(1,1,4-trioxo-1,2,5-thiadiazolidin-2-yl)-benzyl]-phenyl)-N-methyl-methanesulfonamide The title compound is prepared according to the general procedures outlined in Example 1, Steps I-K: MS (M–H)⁻= 424.

EXAMPLE 15

5-[2-Hydroxy-4-(2-methanesulfonylmethylbenzyl)-phenyl]-1,1-dioxo-1,2,5-thiadiazolidin-3-one

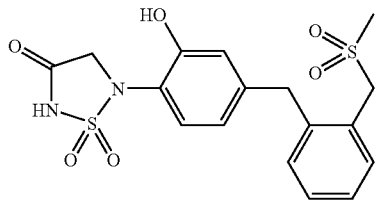

A. 1-Chloromethyl-2-methanesulfonylmethylbenzene

To a solution of α,α'-dichloro-o-xylene (3.5 g, 18 mmol) in DMF (20 mL) is added sodium methanesulfinate (0.612 g, 6.0 mmol) and the mixture is stirred at 65° C. for 4 h. Ice/water and EtOAc are added, the phases are separated and the organic phase is washed with water and brine, dried over $Na_2SO_4/MgSO_4$, filtered and concentrated. The resulting residue is chromatographed on silica gel, eluting with a gradient of hexane/EtOAc to afford 1-chloromethyl-2-methanesulfonylmethylbenzene as a white solid: MS $(M+NH_4)^+$= 236.

B. 5-[2-Hydroxy-4-(2-methanesulfonylmethylbenzyl)-phenyl]-1,1-dioxo-1,2,5-thiadiazolidin-3-one 5-[2-Hydroxy-4-(2-methanesulfonylmethylbenzyl)-phenyl]-1,1-dioxo-1,2,5-thiadiazolidin-3-one is prepared according to the general procedures outlined in Example 1, Steps H-K: MS (M–H)⁻=409.

EXAMPLE 16

5-{4-(3-Methansulfonylphenyl)methyl-2-hydroxyphenyl}-1,1-dioxo-1,2,5-thiadiazolidin-3-one

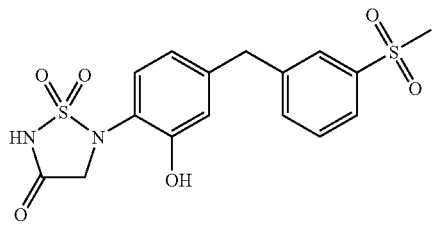

A. 3-Methanesulfonyl benzyl alcohol

To a solution of 3-(methylsulfonyl)benzoic acid (1.2 g, 6.0 mmol) in THF (30 mL) at 0° C., is added equimolar amounts of borane (6.0 mL of a 1.0 M solution in THF) and boron trifluoride diethyl etherate (0.8 mL, 6.0 mmol). The reaction is allowed to warm to ambient temperature overnight, and then quenched by pouring into a mixture of ice and solid $NaHCO_3$. Following extraction with EtOAc, the organic layer is washed with brine and dried over $Na_2SO_4$. Removal of solvent affords the product as a colorless oil: MS $(M+NH_4)^+$= 204.

B. 5-{4-(3-Methansulfonylphenyl)methyl-2-hydroxyphenyl}-1,1-dioxo-1,2,5-thiadiazolidin-3-one 5-{4-(3-Methansulfonylphenyl)methyl-2-hydroxyphenyl}-1,1-dioxo-1,2,5-thiadiazolidin-3-one is prepared according to the general procedures outlined in Example 13, Steps D and E, starting with 3-methanesulfonyl benzyl alcohol and using CsF for the removal of the TMS-ethyl group (Example 10, Step F): MS (M–H)⁻=395.

EXAMPLE 17

C-{2-[3-Hydroxy-4-(1,1,4-trioxo-1,2,5-thiadiazolidin-2-yl)-benzyl]-phenyl}-N,N-dimethylmethanesulfonamide

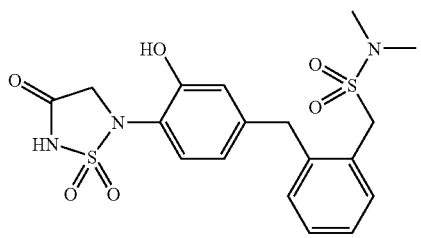

A. 2-N,N-Dimethylsulfonamidomethylbenzoic acid methyl ester

2-N,N-Dimethylsulfonamidomethylbenzoic acid methyl ester is prepared according to the general procedure outlined in Example 13, Step A, starting with 2-sulfonamidomethylbenzoic acid methyl ester.

B. C-(2-Hydroxymethylphenyl)-N,N-dimethylmethanesulfonamide

C-(2-Hydroxymethylphenyl)-N,N-dimethylmethanesulfonamide is prepared according to the general procedure outlined in Example 13, Step C, starting with 2-dimethylsulfamoylmethylbenzoic acid methyl ester.

C. C-{2-[3-Hydroxy-4-(1,1,4-trioxo-1,2,5-thiadiazolidin-2-yl)-benzyl]-phenyl}-N,N-dimethylmethanesulfonamide C-{2-[3-Hydroxy-4-(1,1,4-trioxo-1,2,5-thiadiazolidin-2-yl)-benzyl]-phenyl}-N,N-dimethylmethanesulfonamide is prepared according to the general procedures outlined in Example 3, Steps B and C, and Example 1, Steps J and K: MS (M–H)⁻=438.

EXAMPLE 18

Methanesulfonic acid 2-[3-hydroxy-4-(1,1,4-trioxo-1,2,5-thiadiazoldin-2-yl)-benzyl]-phenyl ester

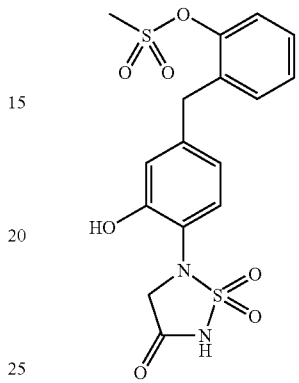

A. 2-Methanesulfonyloxybenzoic acid methyl ester

2-Methanesulfonyloxybenzoic acid methyl ester is prepared according to the general procedure outlined in Example 4, Step B, using 2-hydroxybenzoic acid methyl ester and methanesulfonyl chloride.

B. Methanesulfonic acid 2-hydroxymethylphenylester

Methanesulfonic acid 2-hydroxymethylphenylester is prepared according to the general procedure outlined in Example 13, Step C.

C. Methanesulfonic acid 2-[3-hydroxy-4-(1,1,4-trioxo-1,2,5-thiadiazoldin-2-yl)-benzyl]-phenyl ester Methanesulfonic acid 2-[3-hydroxy-4-(1,1,4-trioxo-1,2,5-thiadiazoldin-2-yl)-benzyl]-phenyl ester is prepared according to the general procedures outlined in Example 3, Steps B and C and Example 1, Steps J and K, starting with methanesulfonic acid 2-hydroxymethylphenylester: MS (M–H)⁻= 411.

EXAMPLE 19

The following compounds are prepared using appropriate starting materials and general methods described in Example 18, with the exception that CsF is used in place of TBAF for the removal of TMS-ethyl group (general procedure is described in Example 10, Step F).

| Example | Chemical Name | MS (m/z) |
| --- | --- | --- |
| 19-1 | Methanesulfonic acid 3-[3-hydroxy-4-(1,1,4-trioxo-1,2,5-thiadiazolidin-2-yl)-benzyl]-naphthalen-2-yl ester | (M – H)⁻ = 461 |
| 19-2 | Methanesulfonic acid 2-[3-hydroxy-4-(1,1,4-trioxo-1,2,5-thiadiazolidin-2-yl)-benzyl]-naphthalen-1-yl ester | (M – H)⁻ = 461 |

-continued

| Example | Chemical Name | MS (m/z) |
|---|---|---|
| 19-3 | Methanesulfonic acid 2-[3-hydroxy-4-(1,1,4-trioxo-1,2,5-thiadiazolidin-2-yl)-benzyl]-4-methylphenyl ester | $(M-H)^- = 425$ |
| 19-4 | Methanesulfonic acid 1-[3-hydroxy-4-(1,1,4-trioxo-1,2,5-thiadiazolidin-2-yl)-benzyl]-naphthalen-2-yl ester | $(M-H)^- = 461$ |
| 19-5 | Methanesulfonic acid 2-[3-hydroxy-4-(1,1,4-trioxo-1,2,5-thiadiazolidin-2-yl)-benzyl]-4-methoxyphenyl ester | $(M-H)^- = 441$ |
| 19-6 | Methanesulfonic acid 2-[3-hydroxy-4-(1,1,4-trioxo-1,2,5-thiadiazolidin-2-yl)-benzyl]-6-methylphenyl ester | $(M-H)^- = 425$ |
| 19-7 | Ethanesulfonic acid 2-[3-hydroxy-4-(1,1,4-trioxo-1,2,5-thiadiazolidin-2-yl)-benzyl]-4-methylphenyl ester | $(M-H)^- = 439$ |
| 19-8 | Propane-1-sulfonic acid 2-[3-hydroxy-4-(1,1,4-trioxo-1,2,5-thiadiazolidin-2-yl)-benzyl]-4-methylphenyl ester | $(M-H)^- = 453$ |
| 19-9 | Methanesulfonic acid 4-chloro-2-[3-hydroxy-4-(1,1,4-trioxo-1,2,5-thiadiazolidin-2-yl)-benzyl]-phenyl ester | $(M-H)^- = 445$ |
| 19-10 | Methanesulfonic acid 2-[3-hydroxy-4-(1,1,4-trioxo-1,2,5-thiadiazolidin-2-yl)-benzyl]-5-methylphenyl ester | $(M-H)^- = 425$ |
| 19-11 | Methanesulfonic acid 4-chloro-2-[3-hydroxy-4-(1,1,4-trioxo-1,2,5-thiadiazolidin-2-yl)-benzyl]-6-methylphenyl ester | $(M-H)^- = 459$ |
| 19-12 | Ethanesulfonic acid 2-[3-hydroxy-4-(1,1,4-trioxo-1,2,5-thiadiazolidin-2-yl)-benzyl]-phenyl ester | $(M-H)^- = 425$ |
| 19-13 | Propane-1-sulfonic acid 2-[3-hydroxy-4-(1,1,4-trioxo-1,2,5-thiadiazolidin-2-yl)-benzyl]-phenyl ester | $(M-H)^- = 439$ |

EXAMPLE 20

5-[4-(2-Fluoro-4-methylbenzyl)-2-hydroxyphenyl]-1,1-dioxo-1,2,5-thiadiazolidin-3-one

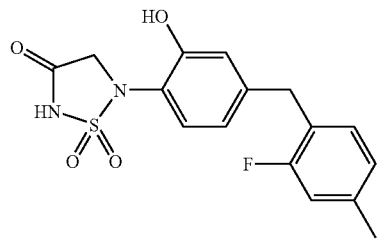

A. 5-[2-Benzyloxy-4-(2-fluoro-4-methylbenzyl)-phenyl]-1,1-dioxo-2-(2-trimethylsilanylethyl)-1,2,5-thiadiazolidin-3-one 5-[2-Benzyloxy-4-(2-fluoro-4-methylbenzyl)-phenyl]-1,1-dioxo-2-(2-trimethylsilanylethyl)-1,2,5-thiadiazolidin-3-one is prepared analogously to Example 1, Step I, using 2-fluoro-1-iodomethyl-4-methylbenzene.

B. 5-[2-Benzyloxy-4-(2-fluoro-4-methylbenzyl)-phenyl]-1,1-dioxo-1,2,5-thiadiazolidin-3-one 5-[2-Benzyloxy-4-(2-fluoro-4-methylbenzyl)-phenyl]-1,1-dioxo-1,2,5-thiadiazolidin-3-one is prepared analogously to Example 10, Step F.

C. 5-[4-(2-Fluoro-4-methylbenzyl)-2-hydroxyphenyl]-1,1-dioxo-1,2,5-thiadiazolidin-3-one 5-[4-(2-Fluoro-4-methylbenzyl)-2-hydroxyphenyl]-1,1-dioxo-1,2,5-thiadiazolidin-3-one is prepared analogously to Example 1, Step K: MS $(M-H)^- = 351$.

EXAMPLE 21

3-[3-Hydroxy-4-(1,1,4-trioxo-1,2,5-thiadiazolidin-2-yl)-benzyl]-N-methylbenzamide potassium salt

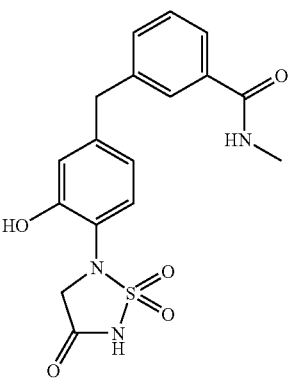

A. 3-[3-Benzyloxy-4-(1,1,4-trioxo-1,2,5-thiadiazolidin-2-yl)-benzyl]-benzoic acid To a solution of 3-[3-benzyloxy-4-(1,1,4-trioxo-1,2,5-thiadiazolidin-2-yl)-benzyl]-benzoic acid methyl ester (intermediate from Example LBY596) (0.3 g, 0.643 mmol) in THF is added a solution of LiOH (0.081 g, 1.929 mmol) in $H_2O$. The reaction is stirred at ambient temperature overnight. The mixture is poured into 1 M HCl and extracted with EtOAc. The organic layer is dried over $MgSO_4$, filtered and concentrated to afford a brown oil. The oil is place under high vacuum to afford solid 3-[3-benzyloxy-4-(1,1,4-trioxo-1,2,5-thiadiazolidin-2-yl)-benzyl]-benzoic acid: MS $(M-H)^-$=451.2.

B. 3-[3-Benzlyoxy-4-(1,1,4-trioxo-1,2,5-thiadiazolidin-2-yl)-benzyl]-N-methylbenzamide To a solution of 3-[3-benzyloxy-4-(1,1,4-trioxo-1,2,5-thiadiazolidin-2-yl)-benzyl]-benzoic acid (0.05 g, 0.1104 mmol) in THF is added DIPEA (0.021 g, 0.029 mL, 0.166 mmol). The mixture is added to a suspension of PS-carbodiimide (0.151 g, 0.166 mmol) and shaken at ambient temperature for 30 min. Methylamine (2 M in THF, 0.055 mL) is added and the solution becomes cloudy. DMF (1 mL) is added and the reaction turns clear again. The mixture is stirred at ambient temperature overnight, then is filtered and the filtrate is washed with 1 M HCl and extracted with EtOAc. The organic layer is dried over $MgSO_4$, filtered and concentrated to afford 34 mg of a yellow sticky solid. The solid is purified by prep. HPLC to afford 7 mg of 3-[3-benzyloxy-4-(1,1,4-trioxo-1,2,5-thiadiazolidin-2-yl)-benzyl]-N-methylbenzamide as a white fluffy solid: MS $(M+H)^+$=466.2.

C. 3-[3-Hydroxy-4-(1,1,4-trioxo-1,2,5-thiadiazolidin-2-yl)-benzyl]-N-methylbenzamide 3-[3-Hydroxy-4-(1,1,4-trioxo-1,2,5-thiadiazolidin-2-yl)-benzyl]-N-methylbenzamide potassium salt is prepared analogously to Example 1, Step K: MS $(M-H)^-$=374.

EXAMPLE 22

3-[3-Hydroxy-4-(1,1,4-trioxo-1,2,5-thiadiazolidin-2-yl)-benzyl]-benzoic acid dipotassium salt

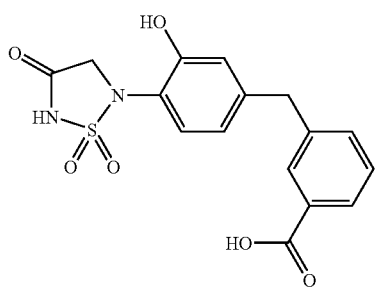

3-[3-Hydroxy-4-(1,1,4-trioxo-1,2,5-thiadiazolidin-2-yl)-benzyl]-benzoic acid dipotassium salt is prepared analogously to Example 21, eliminating Step B: MS $(M-H)^-$=361.

EXAMPLE 23

2-[3-Hydroxy-4-(1,1,4-trioxo-1,2,5-thiadiazolidin-2-yl)-benzyl]-benzoic acid

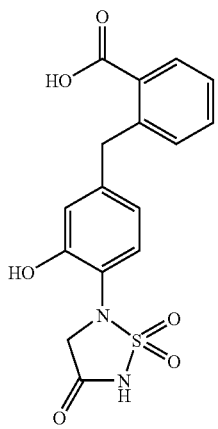

2-[3-Hydroxy-4-(1,1,4-trioxo-1,2,5-thiadiazolidin-2-yl)-benzyl]-benzoic acid is prepared analogously to Example 22, starting with 2-bromomethylbenzoic acid methyl ester: MS $(M-H)^-$=361.

EXAMPLE 24

5-[4-(2,5-Difluorobenzyl)-2-hydroxyphenyl]-1,1-dioxo-1,2,5-thiadiazolidin-3-one

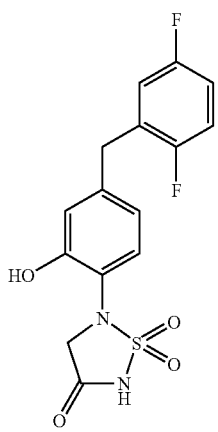

A. 5-[2-Benzyloxy-4-(2,5-difluorobenzyl)-phenyl]-1,1-dioxo-2-(2-trimethylsilanylethyl)-1,2,5-thiadiazolidin-3-one 5-[2-Benzyloxy-4-(2,5-difluorobenzyl)-phenyl]-1,1-dioxo-2-(2-trimethylsilanylethyl)-1,2,5-thiadiazolidin-3-one is prepared analogously to Example 1, Step I, with the exception that 2,5-difluorobenzylzinc bromide is used as the starting material and eliminating Zn dust, 1,2-dibromoethane and TMSCl.

B. 5-[2-Benzyloxy-4-(2,5-difluorobenzyl)-phenyl]-1,1-dioxo-1,2,5-thiadiazolidin-3-one 5-[2-Benzyloxy-4-(2,5-difluorobenzyl)-phenyl]-1,1-dioxo-1,2,5-thiadiazolidin-3-one is prepared according to the general procedure outlined in Example 10, Step F.

C. 5-[4-(2,5-Difluorobenzyl)-2-hydroxyphenyl]-1,1-dioxo-1,2,5-thiadiazolidin-3-one 5-[4-(2,5-Difluorobenzyl)-2-hydroxyphenyl]-1,1-dioxo-1,2,5-thiadiazolidin-3-one is prepared analogously to Example 1, Step K, using Pd(OH)$_2$: MS (M−H)$^−$=353.

EXAMPLE 25

5-[4-(3-Ethylbenzyl)-2-hydroxyphenyl]-1,1-dioxo-1,2,5-thiadiazolidin-3-one

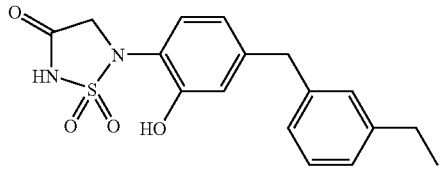

The title compound is prepared using appropriate starting materials and the general procedure described in Example 24, using Pd/C in place of Pd(OH)$_2$.

EXAMPLE 26

5-(2-Hydroxy-4-phenoxyphenyl)-1,1-dioxo-1,2,5-thiadiazolidin-3-one potassium salt

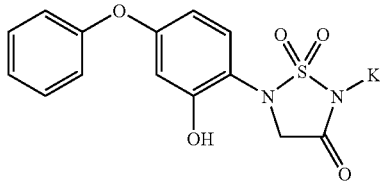

A. 2-Benzyloxy-4-fluoro-1-nitrobenzene

To a suspension of K$_2$CO$_3$ (2.07 g, 15 mmol) in DMF (8 mL) is added 5-fluoro-2-nitrophenol (1.57 g, 10 mmol), followed by benzyl bromide (1.75 g, 10.2 mmol). The mixture is stirred at ambient temperature for 18 h, then poured into water and extracted into EtOAc. The organic phase is washed with water (3×), saturated NaCl (1×) and dried over sodium sulfate. The solvent is removed under reduced pressure and the residual oil filtered through a pad of silica gel using DCM to elute 2-benzyloxy-4-fluoro-1-nitrobenzene as a yellow oil, which slowly solidifies on standing: mp=52-54° C.; $^1$H NMR (CDCl$_3$) δ 8.03-7.98 (m, 2H), 7.53-7.36 (m, 5H), 6.66 (dd, J=10.17, 2.64 Hz, 1H), 6.81-6.73 (m, 1H), 5.26 (s, 2H).

B. 2-Benzyloxy-4-phenoxy-1-nitrobenzene

To a suspension of K$_2$CO$_3$ (0.654 g, 4.74 mmol) in DMF (6 mL) is added 2-benzyloxy-4-fluoro-1-nitrobenzene (0.90 g, 3.64 mmol), followed by phenol (0.343 g, 3.64 mmol). The mixture is stirred at 100° C. for 48 h. The mixture is allowed to cool to ambient temperature, then poured into water and extracted into EtOAc. The organic phase is washed with water (2×), saturated NaCl (1×), and dried over Na$_2$SO$_4$. The solvent is removed under reduced pressure to afford 2-benzyloxy-4-phenoxy-1-nitrobenzene as a pale-yellow solid: mp=96-98° C.; $^1$H NMR (CDCl$_3$) δ 7.87 (d, J=9.09 Hz, 1H), 7.36-7.23 (m, 7H), 7.20-7.15 (m, 1H), 6.95 (dd, J=8.59, 1.01 Hz, 1H), 6.58 (d, J=2.27 Hz, 1H), 6.46-6.43 (m, 1H), 5.08 (s, 2H).

C. 2-Benzyloxy-4-phenoxyphenylamine

To a mixture of 2-benzyloxy-4-phenoxy-1-nitrobenzene (1.0 g, 3.12 mmol) and indium powder (1.0 g, 8.7 mmol) in THF (8 mL) is added concentrated HCl (1.5 mL) dropwise. The mixture is stirred at ambient temperature for 2.5 h. The solution is decanted from unreacted indium and 2N NaOH is added, which results in the formation of a gummy precipitate. The residue is triturated with EtOAc and centrifuged. The solution is decanted and the solvent removed under reduced pressure to afford a dark oil. The residue is purified by flash chromatography using DCM to elute 2-benzyloxy-4-phenoxyphenylamine as an oil: $^1$H NMR (CDCl$_3$) δ 7.43-7.23 (m, 8H), 7.00 (t, 1H), 6.92-6.88 (m, 1H), 6.69 (d, J=8.33 Hz, 1H), 6.63 (d, J=2.52 Hz, 1H), 6.51 (dd, J=8.34, 2.52 Hz, 1H), 5.00 (s, 2H), 3.71 (br s, 2H); MS (M+H)$^+$=292.

D. (2-Benzyloxy-4-phenoxyphenylamino)acetic acid methyl ester

To a mixture of 2-benzyloxy-4-phenoxyphenylamine (400 mg, 1.37 mmol) and K$_2$CO$_3$ (284 mg, 2.05 mmol) in DMF (5 mL) is added methyl bromoacetate (231 mg, 1.51 mmol). The mixture is stirred at 60° C. for 90 min., then an additional methyl bromoacetate (50 mg) is added and the mixture is stirred at 60° C. for 1 h. The mixture is allowed to cool to ambient temperature, then poured into water and extracted into EtOAc. The organic phase is washed with water (3×), saturated NaCl (1×) and dried over Na$_2$SO$_4$. The solvent is removed under reduced pressure to afford (2-benzyloxy-4-phenoxyphenylamino)acetic acid methyl ester. This is used directly in the next step.

E. N-(t-Butoxycarbonylsulfamoyl)-N-(2-benzyloxy-4-phenoxyphenyl)glycine methyl ester To a solution of chlorosulfonyl isocyanate (0.274 g, 1.93 mmol) in DCM (2 mL) is added dropwise a solution of t-butanol (0.143 g, 1.93 mmol) in 1 mL DCM. The solution is stirred at ambient temperature for 45 min. A solution of (2-benzyloxy-4-phenoxyphenylamino)acetic acid methyl ester (0.50 g, 1.38 mmol) and triethylamine (0.278 g, 2.75 mmol) in DCM (1 mL) is added dropwise. The mixture is stirred at ambient temperature for 30 min., then washed with Water. The organic phase is dried over Na$_2$SO$_4$ and the solvent removed under reduced pressure. The residual oil is purified by flash chromatography using DCM to elute N-(t-butoxycarbonylsulfamoyl)-N-(2-benzyloxy-4-phenoxyphenyl)glycine methyl ester as an oil: $^1$H NMR (CDCl$_3$) δ 7.50 (d, J=8.84 Hz, 1H), 7.34-7.23 (m, 8H), 7.08 (t, 1H), 6.92-6.88 (m, 2H), 6.50 (d, J=2.53 Hz, 1H), 6.43 (dd, J=11.12, 2.53 Hz, 1H), 5.22 (s, 2H), 5.01 (s, 2H), 3.62 (s, 3H), 1.36 (s, 9H); MS (M−H)$^−$=541.

F. N-Sulfamoyl-N-(2-benzyloxy-4-phenoxyphenyl)glycine methyl ester

A solution of N-(t-butoxycarbonylsulfamoyl)-N-(2-benzyloxy-4-phenoxyphenyl)glycine methyl ester (0.375 g, 0.69 mmol) in 6 mL TFA/DCM (1:1) is stirred at ambient temperature for 20 min. The solvent is removed under reduced pressure. Methylene chloride is added to the residue and removed under reduced pressure. The resulting oil is purified by flash chromatography using 10% EtOAc/DCM to elute N-sulfamoyl-N-(2-benzyloxy-4-phenoxyphenyl)glycine methyl ester as an oil: $^1$H NMR (CDCl$_3$) δ 7.44 (d, J=8.59 Hz, 1H), 7.33-7.26 (m, 7H), 7.09 (t, 1H), 6.97-6.93 (m, 2H), 6.60 (d, J=2.52 Hz, 1H), 6.43 (dd, J=8.59, 2.53 Hz, 1H), 4.96 (s, 2H), 4.26 (s, 2H), 3.62 (s, 3H); MS (M−H)$^−$=441.

G. 5-(2-Benzyloxy-4-phenoxyphenyl)-1,1-dioxo-1,2,5-thiadiazolidin-3-one potassium salt To a solution of N-sulfamoyl-N-(2-benzyloxy-4-phenoxyphenyl)glycine methyl ester (0.28 g, 0.63 mmol) in THF (5 mL) is added dropwise a 1.0 M solution of potassium t-butoxide (0.63 mL) in TH The mixture is stirred at ambient temperature for 24 h. The solvent is removed under reduced pressure to afford 5-(2-benzyloxy-4-phenoxyphenyl)-1,1-dioxo-1,2,5-thiadiazolidin-3-one potassium salt as a gum. This is used directly in the next step: MS (M−H)$^−$=409.

H. 5-(2-Hydroxy-4-phenoxyphenyl)-1,1-dioxo-1,2,5-thiadiazolidin-3-one

A solution of 5-(2-benzyloxy-4-phenoxyphenyl)-1,1-dioxo-1,2,5-thiadiazolidin-3-one potassium salt (0.30 g, 0.67 mmol) in water (10 mL) is hydrogenated at 1 atm over 10% Pd/C (0.05 g) for 24 h. The catalyst is filtered and the water removed by lyophilization to afford the product, 5-(2-hydroxy-4-phenoxyphenyl)-1,1-dioxo-1,2,5-thiadiazolidin-3-one potassium salt, as an amorphous pale-grey solid: mp=205-210° C.; $^1$H NMR (DMSO-d$_6$) δ 9.52 (br s, 1H), 7.47-7.41 (m, 3H), 7.19 (t, 1H), 7.08 (d, J=7.57 Hz, 2H), 6.51 (d, J=2.78 Hz, 1H), 6.46 (dd, J=8.59, 2.78 Hz, 1H), 4.06 (s, 2H); MS (M−H)$^−$=319.

EXAMPLE 27

2-Hydroxy-6-[3-hydroxy-4-(1,1,4-trioxo-1,2,5-thiadiazolidin-2-yl)-benzyl]-benzonitrile

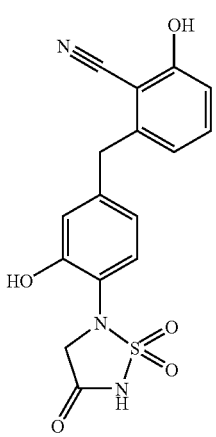

A. 2-Benzyloxy-4-fluoro-1-nitrobenzene

The title compound is prepared following the procedure as described in Example 26, Step A: MS (M+18)$^+$=265.

B. 2-(3-Benzyloxy-4-nitrophenyl)-malonic acid tert-butyl ester ethyl ester

To a suspension of NaH (60%, 9.38 g, 235 mmol) in DMF (200 mL) at 0° C. under N$_2$ is added tert-butyl ethyl malonate (45.7 mL, 243 mmol) over 30 min. The reaction is stirred for 1.5 h in an ice bath. 2-Benzyloxy-4-fluoro-1-nitrobenzene (20.0 g, 80.9 mmol) is added and the reaction heated to 50° C. for 7.5 h. The reaction is quenched with H$_2$O (600 mL) and extracted with EtOAc (2 L). The organic phase is concentrated to ~1 L, washed with H$_2$O (2×500 mL) and brine (300 mL), and dried over Na$_2$SO$_4$. Evaporation yields a yellow oil. The oil is azeotroped with DCM and the resulting solid is triturated with a hexanes/Et$_2$O solution, affording a yellow solid. Two additional crops of the solid are obtained from the filtrate upon standing. The solids are combined to afford 2-(3-benzyloxy-4-nitrophenyl)-malonic acid tert-butyl ester ethyl ester: MS (M−H)$^−$=414.

C. (3-Benzyloxy-4-nitrophenyl)-acetic acid ethyl ester 2-(3-Benzyloxy-4-nitrophenyl)-malonic acid tert-butyl ester ethyl ester (5.00 g, 12.0 mmol) is suspended in formic acid (60 mL) and stirred at RT for 18 h. The solvent is removed under reduced pressure and the residue taken up in EtOAc (100 mL). The organic solution is extracted with saturated NaHCO$_3$ (2×50 mL) and brine (30 mL), before being dried over Na$_2$SO$_4$ and concentrated to an oil. Purification by flash column (10-15% EtOAc/hexanes) affords (3-benzyloxy-4-nitrophenyl)-acetic acid ethyl ester as a yellow oil: MS (M+H)$^+$=316.

D. 2-Benzyloxy-6-fluorobenzonitrile 2-benzyloxy-6-fluorobenzonitrile is prepared according to the procedure outlined in Step A starting with 2-fluoro-6-hydroxybenzonitrile.

E. 2-Benzyloxy-6-(3-benzyloxy-4-nitrobenzyl)-benzonitrile (3-Benzyloxy-4-nitrophenyl)-acetic acid ethyl ester (Step C) (1.90 g, 6.03 mmol) and 2-benzyloxy-6-fluorobenzonitrile (Step D) (2.74 g, 12.1 mmol) are dissolved in DMF (18 mL) and added dropwise to a suspension of Cs$_2$CO$_3$ (5.89 g, 18.1 mmol) in DMF (18 mL). The mixture is heated to 80° C. for 1.5 h, then stirred at 60° C. for 16 h. The mixture is diluted with EtOAc (350 mL) and extracted with 1N HCl (2×75 mL), followed by brine (75 mL). The organic phase is dried over Na$_2$SO$_4$ and concentrated. The residue is taken up in THF (18 mL), MeOH (18 mL) and 1N NaOH (36 mL). Decarboxylation is complete after 2 h, the reaction mixture is poured into ice water (100 mL) and acidified to pH ~2 with 6N HCl. The mixture is extracted with EtOAc (2×200 mL) and the organic phase is washed with brine (75 mL), dried over Na$_2$SO$_4$ and concentrated to afford a brown oil. Purification by flash column (10-75% EtOAc/hexanes) affords 2-benzyloxy-6-(3-benzyloxy-4-nitrobenzyl)-benzonitrile as an off-white solid: MS (M+H)$^+$=451.

F. 2-(4-Amino-3-benzyloxybenzyl)-6-benzyloxybenzonitrile

To a solution of 2-benzyloxy-6-(3-benzyloxy-4-nitrobenzyl)-benzonitrile (0.564 g, 1.25 mmol) in EtOAc (50 mL), under $N_2$, is added platinum oxide (0.112 g, 0.493 mmol). The suspension is stirred under an $H_2$ atmosphere. Upon consumption of the starting material by LC/MS, the reaction mixture is passed through a plug of Celite and concentrated. Purification of the residue by flash chromatography (15-20% EtOAc/hexanes) affords 2-(4-amino-3-benzyloxybenzyl)-6-benzyloxybenzonitrile as a yellow oil: MS $(M+H)^+=421$.

G. [2-Benzyloxy-4-(3-benzyloxy-2-cyanobenzyl)-phenylamino]-acetic acid ethyl ester Ethyl glyoxlate is added to a solution of 2-(4-amino-3-benzyloxybenzyl)-6-benzyloxybenzonitrile (0.281 g, 0.668 mmol), ACN (3 mL) and AcOH (1.5 mL) under $N_2$. The mixture is stirred at ambient temperature for 2 h. The reaction is cooled in an ice bath and a slurry of sodium triacetoxyborohydride (0.284 g, 1.34 mmol) and ACN (1.5 mL) is added dropwise. Upon consumption of the starting material by LC/MS, the reaction is concentrated and the residue quenched with saturated $NaHCO_3$ (2×10 mL). The mixture is extracted with DCM (40 mL) and the organics dried over $Na_2CO_3$. Evaporation affords [2-benzyloxy-4-(3-benzyloxy-2-cyanobenzyl)-phenylamino]-acetic acid ethyl ester as a green oil: MS $(M+H)^+=507$.

H. 2-Benzyloxy-6-[3-benzyloxy-4-(1,1,4-trioxo-1,2,5thiadiazolidin-2-yl)-benzyl]-benzonitrile 2-Benzyloxy-6-[3-benzyloxy-4-(1,1,4-trioxo-1,2,5thiadiazolidin-2-yl)-benzyl]-benzonitrile is prepared analogously to Example 26, Steps D to F.

I. 2-Hydroxy-6-[3-hydroxy-4-(1,1,4-trioxo-1,2,5-thiadiazolidin-2-yl)-benzyl]-benzonitrile 2-Hydroxy-6-[3-hydroxy-4-(1,1,4-trioxo-1,2,5-thiadiazolidin-2-yl)-benzyl]-benzonitrile is prepared analogously to Example 24, Step C: MS $(M-H)^-=358.1$; $^1H$ NMR (MeOD) δ 7.33 (d, J=8 Hz, 1H), 7.23 (t, J=8 Hz, 1H), 6.73 (m, 2H), 6.67 (d, J=8 Hz, 1H), 6.55 (d, J=7.58 Hz, 1H), 4.30 (s, 2H), 3.97 (s, 2H).

EXAMPLE 28

2-[3-Hydroxy-4-(1,1,4-trioxo-1,2,5-thiadiazolidin-2-yl)-benzyl]-4-trifluoromethylbenzonitrile

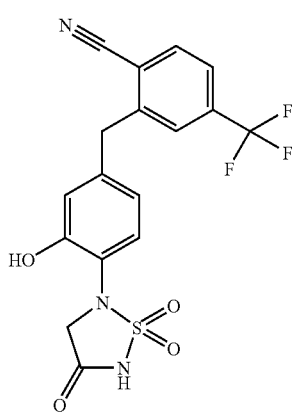

2-[3-Hydroxy-4-(1,1,4-trioxo-1,2,5-thiadiazolidin-2-yl)-benzyl]-4-trifluoromethylbenzonitrile is prepared according to the general procedures outlined in Example 27, using 2-fluoro-4-trifluoromethylbenzonitrile in Step E: $^1H$ NMR (MeOD) δ 7.92 (d, J=8.0 Hz, 1H), 7.75 (s, 1H), 7.70 (m, 1H), 7.39 (d, J=7.83 Hz, 1H), 6.75 (m, 2H), 4.30 (s, 2H), 4.22 (s, 2H). MS $(M-H)^-=410$

EXAMPLE 29

2-[3-Hydroxy-4-(1,1,4-trioxo-1,2,5-thiadiazolidin-2-yl)-benzyl]-4-methylbenzonitrile

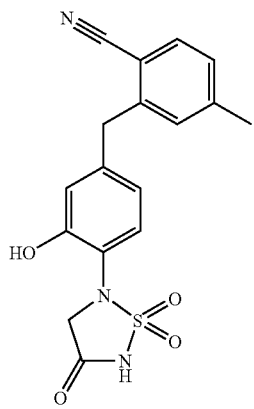

2-[3-Hydroxy-4-(1,1,4-trioxo-1,2,5-thiadiazolidin-2-yl)-benzyl]-4-methylbenzonitrile is prepared according to the general procedures outlined in Example 27, using 2-fluoro-4-methylbenzonitrile in Step E: $^1H$ NMR (MeOD) δ 7.56 (d, J=7.83 Hz, 1H), 7.33 (d, J=8.08 Hz, 1H), 7.23 (s, 1H), 7.19 (d, J=7.83 Hz, 1H), 6.73 (s, 1H), 6.65 (dd, J=8.0, 2.0 Hz, 1H), 4.31 (s, 2H), 4.05 (s, 2H), 2.36 (s, 3H). MS $(M-H)^-=356$.

EXAMPLE 30

2-[3-Hydroxy-4-(1,1,4-trioxo-1,2,5-thiadiazolidin-2-yl)-benzyl]-6-methyl-benzonitrile

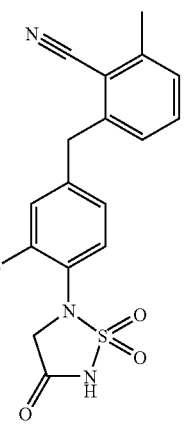

A. 3-Benzyloxy-4-nitrobenzaldehyde

To a stirred solution of benzyl bromide (6.9 g, 40.3 mmol) and 3-hydroxy-4-nitrobenzaldehyde (9.7 g, 58.0 mmol) is added $K_2CO_3$ (8.9 g, 64.4 mmol). The mixture is stirred at ambient temperature overnight, diluted with water and extracted with EtOAc. The organic phase is washed with aqueous $K_2CO_3$ and brine, dried over $MgSO_4$, filtered and concentrated to afford 3-benzyloxy-4-nitrobenzaldehyde as a yellow solid: MS $(M+H)^+=258$.

B. (3-Benzyloxy-4-nitrophenyl)-methanol

3-Benzyloxy-4-nitrobenzaldehyde (10.3 g, 0.040 mol) is dissolved in methanol (120 mL) with heating and then cooled to 0° C. To this stirred solution, sodium borohydride (1.5 g, 0.40 mol) is added in portions over a period of 5 min. The mixture is allowed to warm to ambient temperature and stirred overnight. The solvent is removed under reduced pressure and EtOAc is added. The organic layer is washed with 1N HCl and brine, dried over sodium sulfate/magnesium sulfate, and concentrated to afford (3-benzyloxy-4-nitrophenyl)-methanol as a yellow-brown solid: MS $(M+NH_4)^+=277$.

C. 2-Benzyloxy-4-bromomethyl-1-nitrobenzene

To a stirred solution of (3-benzyloxy-4-nitrophenyl)-methanol (11.0 g, 0.042 mol) in anhydrous THF is added triethylamine (8.7 g, 0.86 mol). The mixture is cooled to −20° C., followed by the addition of methanesulfonyl chloride (5.8 g, 0.051 mol) and then stirred at −20° C. for 45 min. To this mixture is added lithium bromide (37.3 g, 0.43 mol) in anhydrous THF (40 mL) over 40 min. followed by stirring at ambient temperature for 2 h. The suspension is concentrated under reduced pressure and diluted with EtOAc and water. The organic phase is washed with brine, dried over $MgSO_4$, filtered and concentrated to afford 2-benzyloxy-4-bromomethyl-1-nitrobenzene as a yellow solid.

D. 2-Methyl-6-(4,4,5,5-tetramethyl-[1,3,2]dioxaborolan-2-yl)-benzonitrile $Pd_2(dba)_3$ (764 mg, 0.834 mmol) and tricyclohexylphosphine (547 mg, 1.95 mmol) are dissolved in dioxane (50 mL) and the mixture is stirred under nitrogen for 30 min. To this is added bis(pinacolato)diboron (3.89 g, 15.3 mmol), KOAc (2.05 g, 20.9 mmol) and 2-chloro-6-methylbenzonitrile (2.10 g, 13.9 mmol). The suspension is heated in a microwave at 100° C. for 20 min. Additional KOAc (480 mg) is added. The reaction mixture is heated for an additional 20 min. at 100° C. in a microwave. The reaction mixture is diluted with toluene (100 mL) and water (50 mL). The organic phase is separated and filtered through Celite and concentrated. The brown residue is used in the next step.

E. 2-(3-Benzyloxy-4-nitrobenzyl)-6-methylbenzonitrile

A mixture of 2-benzyloxy-4-bromomethyl-1-nitrobenzene (2.99 g, 9.27 mmol) and $Pd(PPh_3)_4$ (536 mg, 0.464 mmol) in DME (10 mL) is heated to 60° C. for 2 min. in a microwave. 2-methyl-6-(4,4,5,5-tetramethyl-[1,3,2]dioxaborolan-2-yl)-benzonitrile (5.96 g of crude, ~13.9 mmol) in DME (10 mL) and EtOH (2 mL) is added along with $Na_2CO_3$ (2 M, 3.3 mL). The reaction mixture is heated to 110° C. for 30 min. by microwave. Then the reaction is heated to 120° C. for an additional 15 min. by microwave. The reaction mixture is diluted with DCM (150 mL) and extracted with water (50 mL). The aqueous layer is extracted with DCM (30 mL) and the combined organics is dried over $Na_2SO_4$. Evaporation yields a brown oil, and it is then purified by flash column to yield a tan solid as the title compound: MS $(M-H)^-=357.2$.

F. 2-[3-Hydroxy-4-(1,1,4-trioxo-1,2,5-thiadiazolidin-2-yl)-benzyl]-6-methylbenzonitrile The title compound is prepared analogously to Example 27, Steps F-H: MS $(M-H)^-=356.7$.

EXAMPLE 31

2-[3-Hydroxy-4-(1,1,4-trioxo-1,2,5-thiadiazolidin-2-yl)-benzyl]-4-trifluoromethylbenzonitrile

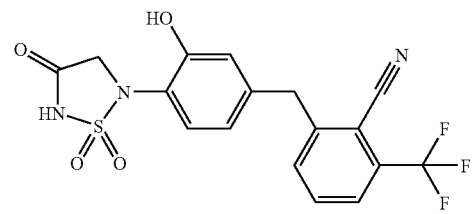

2-[3-Hydroxy-4-(1,1,4-trioxo-1,2,5-thiadiazolidin-2-yl)-benzyl]-4-trifluoromethylbenzonitrile is prepared according to the general procedures outlined in Example 27, using 2-fluoro-6-trifluoromethylbenzonitrile in Step E: MS $(M-H)^-=410$.

EXAMPLE 32

5-(2-Hydroxy-4-phenylsulfanylphenyl)-1,1-dioxo-1,2,5-thiadiazolidin-3-one

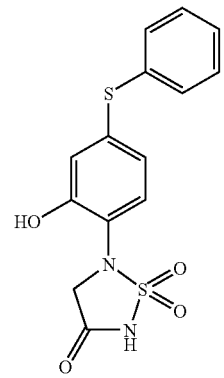

A. 2-Benzyloxy-1-nitro-4-phenylsulfanylbenzene

A 60% suspension of sodium hydride in mineral oil (490 mg, 12.2 mmol) is stirred in 15 mL of DMF. To this mixture is carefully added benzenethiol (1.25 mL, 1.34 g, 12.2 mmol) and the mixture stirred for 1 h. To this solution is added portionwise 2-benzyloxy-4-fluoronitrobenzene (3.00 g, 12.1 mmol), giving initially a dark solution that eventually changed to pale yellow. When LC shows disappearance of starting material, the mixture is poured into ethyl acetate and extracted with water, 1N sodium hydroxide, and four times with brine. This solution is dried, filtered, and solvent removed under reduced pressure to leave a heterogeneous mixture that is triturated with hexane, filtered, and the solids washed with hexane to afford 2-benzyloxy-1-nitro-4-phenylsulfanylbenzene, mp 77-79° C.: NMR (CDCl$_3$) δ 7.79 (d, 1H, J=8.6 Hz), 7.46 (m, 5H), 7.33 (m, 5H), 6.77 (d, 1H, J=1.8 Hz), 6.72 (dd, 1H, J=8.6, 1.8 Hz), 5.08 (s, 2H).

B. 5-(2-Benzyloxy-4-phenylsulfanylphenyl)-1,1-dioxo-1,2,5-thiadiazolidin-3-one The title compound is prepared analogously to Example 26, Steps C to F from 2-benzyloxy-1-nitro-4-phenylsulfanylbenzene.

C. 5-(2-Hydroxy-4-phenylsulfanylphenyl)-1,1-dioxo-1,2,5-thiadiazolidin-3-one The title compound is prepared analogously to Example 11, Step C: MS (M–H)$^-$=335.

EXAMPLE 33

2-[3-Hydroxy-4-(1,1,4-trioxo-1,2,5-thiadiazolidin-2-yl)-phenylsulfanyl]-4-trifluoromethylbenzonitrile

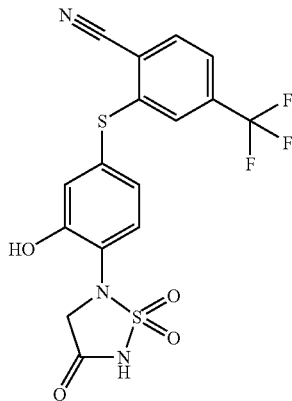

A. 3-Benzyloxy-4-nitrobenzenethiol

To a suspension of NaH (60%, 1.21 g, 30.3 mmol) in dry DMF (20 mL) under N$_2$ at 0° C. is added dropwise 3-mercaptopropionic acid ethyl ester (1.9 mL, 15.2 mmol) and 2-benzyloxy-4-fluoro-1-nitrobenzene (intermediate from Example 27) (2.5 g, 10.1 mmol) in dry DMF (10 mL). The reaction is allowed to warm to ambient temperature and stirred for 4 days. The mixture is then diluted with EtOAc (100 mL) and extracted with 1N HCl (50 mL). The organics are washed with brine and dried with Na$_2$SO$_4$. Evaporation yields a yellow oil which is purified by flash chromatography (30-50% EtOAc). The title compound is isolated as a yellow oil: MS (M–H)$^-$=260.2.

B. 2-[3-Benzyloxy-4-(1,1,4-trioxo-1,2,5-thiadiazolidin-2-yl)-phenylsulfanyl]-4-trifluoromethylbenzonitrile The title compound is prepared analogously to Example 27, Steps E to G, starting form 3-benzyloxy-4-nitrobenzenethiol and 2-fluoro-4-trifluoromethylbenzonitrile.

C. 2-[3-Hydroxy-4-(1,1,4-trioxo-1,2,5-thiadiazolidin-2-yl)-phenylsulfanyl]-4-trifluoromethylbenzonitrile The title compound is prepared analogously to Example 11, Step C: MS (M–H)$^-$=428.

EXAMPLE 34

2-[3-Hydroxy-4-(1,1,4-trioxo-1,2,5-thiadiazolidin-2-yl)-phenylsulfanyl]-6-trifluoromethylbenzonitrile

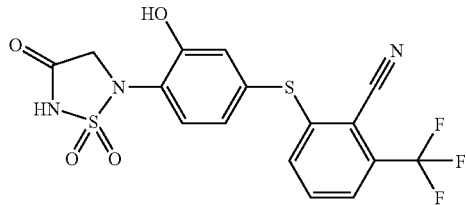

The title compound is prepared analogously to Example 33, from 2-fluoro-6-trifluoromethyl-benzonitrile: MS (M–H)$^-$=428.

EXAMPLE 35

Methanesulfonic acid 2-[3-diethylcarbamoyloxy-4-(1,1,4-trioxo-1,2,5-thiadiazolidin-2-yl)-benzyl]-phenyl ester

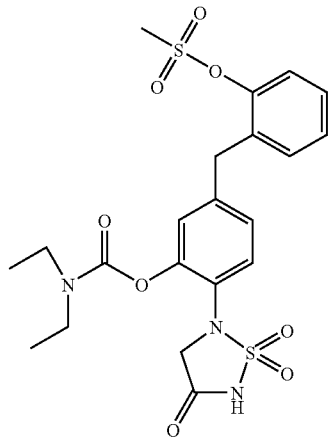

A. tert-Butyl N-(2-(benzyloxy)-4-{2-[(methylsulfonyl)oxy]benzyl}phenyl)-N-({(tert-butoxycarbonyl)[2-(trimethylsilyl)ethyl]amino}sulfonyl)glycinate The title compound is prepared analogously to Example 1, Step I, starting with (tert-butyl N-[2-(benzyloxy)-4-iodophenyl]-N-({(tert-butoxycarbonyl)[2-(trimethylsilyl)ethyl]amino}-sulfonyl)glycinate) (intermediate from Example 1) and methanesulfonic acid 2-iodomethylphenyl ester (intermediate from Example 18).

B. tert-Butyl N-(2-hydroxy-4-{2-[(methylsulfonyl)oxy]benzyl}phenyl)-N-({(tert-butoxycarbonyl)[2-(trimethylsilyl)ethyl]amino}sulfonyl)glycinate The title compound is prepared analogously to Example 1, Step K.

C. tert-Butyl N-(2-(diethylcarbamoyl)-4-{2-[(methylsulfonyl)oxy]benzyl}phenyl)-N-({(tert-butoxycarbonyl)[2-(trimethylsilyl)ethyl]amino}sulfonyl)glycinate A mixture of above compound (810 mg, 1.18 mmol), diethylcarbamoyl chloride (0.265 mL, 2.10 mmol) and $K_2CO_3$ (690 mg, 5 mmol) in DMF (10 mL) is heated at 65° C. for 4.5 h. The solvent is removed via vacuum and ice/water is added. EtOAc is used to extract (2×), and the organic layer is washed with $NaCO_3$ (1×), water (1×), and brine (1×). It is then dried with $NaSO_4$ and $MgSO_4$, concentrated to give the title compound.

D. Methanesulfonic acid 2-[3-diethylcarbamoyloxy-4-(1,1,4-trioxo-1,2,5-thiadiazolidin-2-yl)-benzyl]-phenyl ester The title compound is prepared analogously to Example 1, Steps F and G, followed by Example 10, Step F: MS $(M-H)^- = 510$.

EXAMPLE 36

Methanesulfonic acid 2-[3-isopropoxycarbonyloxy-4-(1,1,4-trioxo-1,2,5-thiadiazolidin-2-yl)-benzyl]-phenyl ester

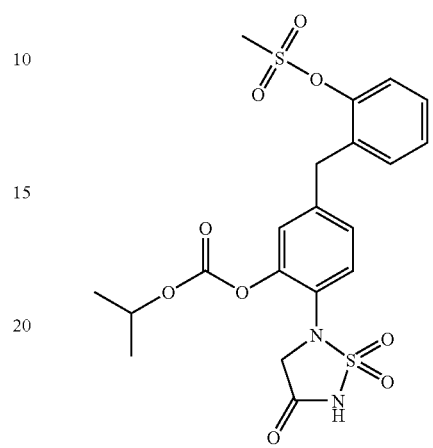

The title compound is prepared analogously to Example 35, with the exception of using isopropyl chloroformate in place of diethylcarbamoyl chloride; and in the last step, TFA is used in place of CsF for the removal of TMS-ethyl group (general procedure outlined in Example 10, Step F): MS $(M-H)^- = 497$.

EXAMPLE 37

The following compounds are prepared using the general procedures outlined in Example 7, with the exception that CsF is used in place of TBAF in Step B for the removal of TMS-ethyl group (general procedure outlined in Example 10, Step F). Step A is omitted for Examples 37-13, 37-15 and 37-16.

| Example | Chemical Name | MS (m/z) |
| --- | --- | --- |
| 37-1 | N-{4-Chloro-2-[3-hydroxy-4-(1,1,4-trioxo-1,2,5-thiadiazolidin-2-yl)-benzyl]-phenyl}-methanesulfonamide | $(M-H)^- = 444$ |
| 37-2 | N-{2-[3-Hydroxy-4-(1,1,4-trioxo-1,2,5-thiadiazolidin-2-yl)-benzyl]-4-methylphenyl}-methanesulfonamide | $(M-H)^- = 424$ |
| 37-3 | N-{4-Fluoro-2-[3-hydroxy-4-(1,1,4-trioxo-1,2,5-thiadiazolidin-2-yl)-benzyl]-phenyl}-methanesulfonamide | $(M-H)^- = 428$ |
| 37-4 | N-{4-Fluoro-2-[3-hydroxy-4-(1,1,4-trioxo-1,2,5-thiadiazolidin-2-yl)-benzyl]-phenyl}-benzenesulfonamide | $(M-H)^- = 490$ |
| 37-5 | Ethanesulfonic acid {4-fluoro-2-[3-hydroxy-4-(1,1,4-trioxo-1,2,5-thiadiazolidin-2-yl)-benzyl]-phenyl}-amide | $(M-H)^- = 442$ |
| 37-6 | Propane-2-sulfonic acid {4-fluoro-2-[3-hydroxy-4-(1,1,4-trioxo-1,2,5-thiadiazolidin-2-yl)-benzyl]-phenyl}-amide | $(M-H)^- = 456$ |
| 37-7 | Propane-1-sulfonic acid {2-[3-hydroxy-4-(1,1,4-trioxo-1,2,5-thiadiazolidin-2-yl)-benzyl]-4-methylphenyl}-amide | $(M-H)^- = 452$ |
| 37-8 | N-{4-Fluoro-2-[3-hydroxy-4-(1,1,4-trioxo-1,2,5-thiadiazolidin-2-yl)-benzyl]-phenyl}-C-phenyl-methanesulfonamide | $(M-H)^- = 504$ |
| 37-9 | Ethanesulfonic acid {4-chloro-2-[3-hydroxy-4-(1,1,4-trioxo-1,2,5-thiadiazolidin-2-yl)-benzyl]-phenyl}-amide | $(M-H)^- = 458$ |
| 37-10 | Propane-2-sulfonic acid {4-chloro-2-[3-hydroxy-4-(1,1,4-trioxo-1,2,5-thiadiazolidin-2-yl)-benzyl]-phenyl}-amide | $(M-H)^- = 472$ |
| 37-11 | Propane-1-sulfonic acid {4-chloro-2-[3-hydroxy-4-(1,1,4-trioxo-1,2,5-thiadiazolidin-2-yl)-benzyl]-phenyl}-amide | $(M-H)^- = 472$ |
| 37-12 | Ethanesulfonic acid {4-chloro-2-[3-hydroxy-4-(1,1,4-trioxo-1,2,5-thiadiazolidin-2-yl)-benzyl]-6-methylphenyl}-amide | $(M-H)^- = 472$ |
| 37-13 | N-{2-[3-Hydroxy-4-(1,1,4-trioxo-1,2,5-thiadiazolidin-2-yl)-benzyl]-6-methylphenyl}-methanesulfonamide | $(M-H)^- = 424$ |

-continued

| Example | Chemical Name | MS (m/z) |
|---|---|---|
| 37-14 | N-{2-[3-Hydroxy-4-(1,1,4-trioxo-1,2,5-thiadiazolidin-2-yl)-benzyl]-4,6-dimethylphenyl}-methanesulfonamide | $(M - H)^- = 438$ |
| 37-15 | Ethanesulfonic acid {2-[3-hydroxy-4-(1,1,4-trioxo-1,2,5-thiadiazolidin-2-yl)-benzyl]-6-methylphenyl}-amide | $(M - H)^- = 438$ |
| 37-16 | Propane-1-sulfonic acid {2-[3-hydroxy-4-(1,1,4-trioxo-1,2,5-thiadiazolidin-2-yl)-benzyl]-6-methylphenyl}-amide | $(M - H)^- = 452$ |
| 37-17 | Ethanesulfonic acid {2-[3-hydroxy-4-(1,1,4-trioxo-1,2,5-thiadiazolidin-2-yl)-benzyl]-4,6-dimethylphenyl}-amide | $(M - H)^- = 452$ |
| 37-18 | N-{4-Chloro-2-[3-hydroxy-4-(1,1,4-trioxo-1,2,5-thiadiazolidin-2-yl)-benzyl]-6-methylphenyl}-methanesulfonamide | $(M - H)^- = 459$ |
| 37-19 | N-{4-Chloro-2-[3-hydroxy-4-(1,1,4-trioxo-1,2,5-thiadiazolidin-2-yl)-benzyl]-6-methylphenyl}-methanesulfonamide | $(M - H)^- = 459$ |
| 37-20 | N-{2-[3-Hydroxy-4-(1,1,4-trioxo-1,2,5-thiadiazolidin-2-yl)-benzyl]-5-methylphenyl}-methanesulfonamide | $(M - H)^- = 424$ |
| 37-21 | N-{2-[3-Hydroxy-4-(1,1,4-trioxo-1,2,5-thiadiazolidin-2-yl)-benzyl]-6-methoxyphenyl}-methanesulfonamide | $(M - H)^- = 440$ |
| 37-22 | N-{5-Chloro-2-[3-hydroxy-4-(1,1,4-trioxo-1,2,5-thiadiazolidin-2-yl)-benzyl]-phenyl}-methanesulfonamide | $(M - H)^- = 445$ |
| 37-23 | Ethanesulfonic acid {2-[3-hydroxy-4-(1,1,4-trioxo-1,2,5-thiadiazolidin-2-yl)-benzyl]-4-methylphenyl}-amide | $(M - H)^- = 438$ |

EXAMPLE 38

Methanesulfonic acid 4-ethyl-2-[3-hydroxy-4-(1,1,4-trioxo-1,2,5-thiadiazolidin-2-yl)-benzyl]-phenyl ester

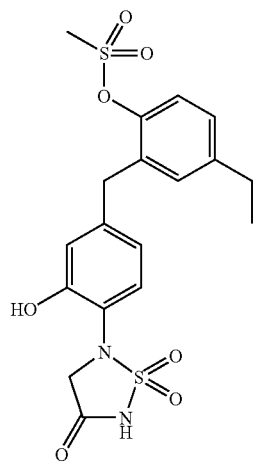

A. 5-Ethyl-2-hydroxybenzoic acid methyl ester

The title compound is prepared analogously to Example 1, Step K, from 5-acetyl-2-hydroxybenzoic acid methyl ester.

B. Methanesulfonic acid 4-ethyl-2-[3-hydroxy-4-(1,1,4-trioxo-1,2,5-thiadiazolidin-2-yl)-benzyl]-phenyl ester The title compound Id prepared analogously to Example 18, Steps A to C, from 5-ethyl-2-hydroxybenzoic acid methyl ester: MS (M–H)⁻=439.

EXAMPLE 39

Methanesulfonic acid 4-tert-butyl-2-[3-hydroxy-4-(1,1,4-trioxo-1,2,5-thiadiazolidin-2-yl)-benzyl]-phenyl ester

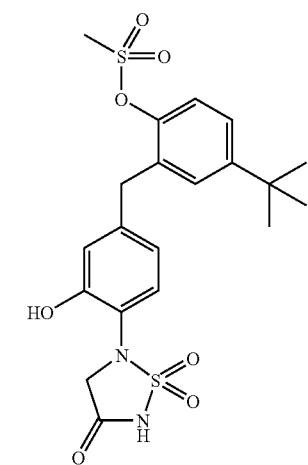

A. Methanesulfonic acid 4-tert-butyl-2-formylphenyl ester

The title compound is prepared analogously to Example 18, Step A, from 5-tert-butyl-2-hydroxybenzoic acid methyl ester.

B. Methanesulfonic acid 4-tert-butyl-2-hydroxymethylphenyl ester

The title compound is prepared analogously to Example 30, Step A, from methanesulfonic acid 4-tert-butyl-2-formylphenyl ester.

C. Methanesulfonic acid 4-tert-butyl-2-[3-hydroxy-4-(1,1,4-trioxo-1,2,5-thiadiazolidin-2-yl)-benzyl]-phenyl ester The title compound is prepared analogously to Example 18, Step C: MS (M−H)⁻=467.

EXAMPLE 40

Diethylcarbamic acid 2-[3-hydroxy-4-(1,1,4-trioxo-1,2,5-thiadiazolidin-2-yl)-benzyl]-4-methylphenyl ester

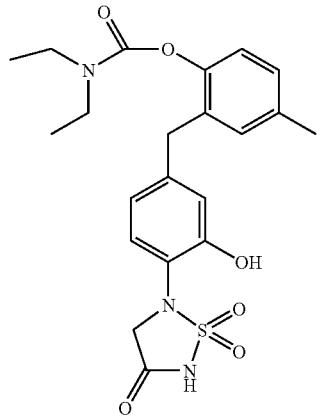

A. 2-(4-Methoxybenzyloxy)-5-methylbenzoic acid methyl ester

2-Hydroxy-5-methylbenzoic acid methyl ester (4.98 g, 30 mmol) and 1-chloromethyl-4-methoxybenzene (4.69 g, 30 mmol) and $K_2CO_3$ (4.55 g, 33 mmol) in DMF (50 mL) is heated to 60° C. for 72 h. The mixture is then diluted with EtOAc (100 mL), and then washed with 1N HCl solution and brine. It is then dried and concentrated. The residue is purified by flash chromatography to give the title compound as a colorless oil.

B. [2-(4-Methoxybenzyloxy)-5-methylphenyl]-methanol

To a solution of 2-(4-methoxybenzyloxy)-5-methylbenzoic acid methyl ester (7.32 g, 25.6 mmol) in THF at 0° C. is added $LiAlH_4$ (1 M in THF, 26 mL, 26 mmol) dropwise and the mixture is stirred for 1 h. $Na_2SO_4$ (saturated, 1 mL) is added dropwise at 0° C. and let it sit for 15 min. More THF (80 mL) is added and it is filtered. The filtrate is then concentrated and EtOAc (100 mL) is added. The organic layer is washed with brine and dried with $MgSO_4$. It is then concentrated to give the title compound.

C. 5-[2-Benzyloxy-4-(2-hydroxy-5-methylbenzyl)-phenyl]-1,1-dioxo-2-(2-trimethylsilanylethyl)-1,2,5-thiadiazolidin-3-one The title compound is prepared analogously to Example 3, Steps B and C, and Example 4, Step A.

D. Diethylcarbamic acid 2-{3-benzyloxy-4-[1,1,4-trioxo-5-(2-trimethylsilanylethyl)-1,2,5-thiadiazolidin-2-yl]-benzyl}-4-methylphenyl ester The title compound is prepared analogously to Example 35, Step C.

E. Diethylcarbamic acid 2-[3-hydroxy-4-(1,1,4-trioxo-1,2,5-thiadiazolidin-2-yl)-benzyl]-4-methylphenyl ester The title compound is prepared analogously to Example 10, Step F, and followed by Example 1, Step K: MS (M−H)⁻= 446.

EXAMPLE 41

Ethanesulfonic acid {4-ethyl-2-[3-hydroxy-4-(1,1,4-trioxo-1,2,5-thiadiazolidin-2-yl)-benzyl]-phenyl}-amide

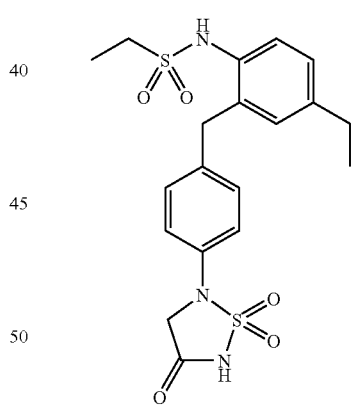

A. 2-Nitro-5-vinylbenzoic acid methyl ester

The title compound is prepared analogously to the method described in Example 30, Step E with the exception of using vinyl boronic acid in place of 2-methyl-6-(4,4,5,5-tetramethyl-[1,3,2]dioxaborolan-2-yl)-benzonitrile.

B. 2-Amino-5-ethylbenzoic acid methyl ester

The title compound is prepared analogously to Example 1, Step K.

C. 2-Amino-5-ethylbenzoic acid

The title compound is prepared analogously to Example 21, Step A with the exception that NaOH is used in place of LiOH.

D. Ethanesulfonic acid {4-ethyl-2-[3-hydroxy-4-(1,1,4-trioxo-1,2,5-thiadiazolidin-2-yl)-benzyl]-phenyl}-amide The title compound is prepared analogously to Example 7 except CsF is in place of TBAF for the removal of TMS-ethyl group (procedure outlined in Example 10, Step F): MS (M–H)⁻=452.

EXAMPLE 42

The following compounds are prepared analogously to Example 41. In the case of Example 42-4, phenylboronic acid is used. In the case of 42-3, beta-benzyl-9-BBN is used.

| Example | Chemical Name | MS (m/z) |
| --- | --- | --- |
| 42-1 | Propane-1-sulfonic acid {4-ethyl-2-[3-hydroxy-4-(1,1,4-trioxo-1,2,5-thiadiazolidin-2-yl)-benzyl]-phenyl}-amide | $(M - H)^- = 466$ |
| 42-2 | N-{4-Ethyl-2-[3-hydroxy-4-(1,1,4-trioxo-1,2,5-thiadiazolidin-2-yl)-benzyl]-phenyl}-methanesulfonamide | $(M - H)^- = 438$ |
| 42-3 | N-{4-Benzyl-2-[3-hydroxy-4-(1,1,4-trioxo-1,2,5-thiadiazolidin-2-yl)-benzylphenyl}methanesulfonamide | $(M - H)^- = 500$ |
| 42-4 | N-{3-[3-Hydroxy-4-(1,1,4-trioxo-1,2,5-thiadiazolidin-2-yl)-benzyl]-biphenyl-4-yl}-methanesulfonamide | $(M - H)^- = 486$ |

EXAMPLE 43

N-{2-[3-Hydroxy-4-(1,1,4-trioxo-1,2,5-thiadiazolidin-2-yl)-benzyl]-4-methoxyphenyl}-methanesulfonamide

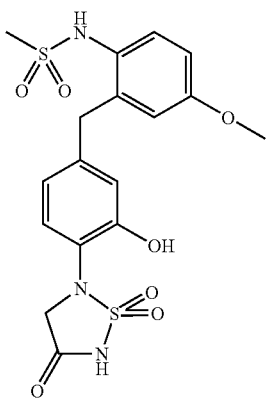

A. 5-Methoxy-2-nitrobenzoic acid

The title compound is prepared analogously to Example 7, Step A.

B. N-{2-[3-Hydroxy-4-(1,1,4-trioxo-1,2,5-thiadiazolidin-2-yl)-benzyl]-4-methoxyphenyl}-methanesulfonamide The title compound is prepared analogously to Example 41, Steps B and D: MS (M–H)⁻=440.

EXAMPLE 44

The following compounds are prepared analogously to Example 43.

| Example | Chemical Name | MS (m/z) |
| --- | --- | --- |
| 44-1 | Ethanesulfonic acid {2-[3-hydroxy-4-(1,1,4-trioxo-1,2,5-thiadiazolidin-2-yl)-benzyl]-4-methoxyphenyl}-amide | $(M - H)^- = 454$ |
| 44-2 | Propane-1-sulfonic acid {2-[3-hydroxy-4-(1,1,4-trioxo-1,2,5-thiadiazolidin-2-yl)-benzyl]-4-methoxyphenyl}-amide | $(M - H)^- = 468$ |

EXAMPLE 45

Methanesulfonic acid 5-[3-hydroxy-4-(1,1,4-trioxo-1,2,6-thiadiazolidin-2-yl)-benzyl]-7-methylindan-4-yl ester

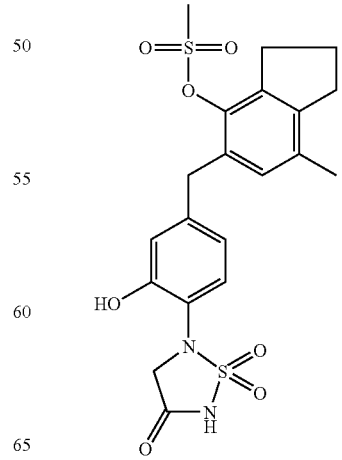

A 4-Benzyloxy-5-bromo-7-methylindan

The title compound is prepared analogously to Example 1, Step A, from 5-bromo-7-methylindan-4-ol.

B. 4-Benzyloxy-7-methylindan-5-carbaldehyde

To a solution of 4-benzyloxy-5-bromo-7-methylindan (5.87 g, 19.4 mmol) in THF (75 mL) at −78° C. is added dropwise n-BuLi (1.6 M in hexane, 13.3 mL, 21.3 mmol) and it is stirred at −78° C. for 1.5 h. DMF (freshly distilled from CaH$_2$, 29 mL, 0.38 mol) is added dropwise and it is stirred at −78° C. for 4 h before slowly warmed to ambient temperature and stirred for 18 h. EtOAc is added and it is washed with 1N HCl and brine, dried and concentrated. The residue is purified by flash chromatography to give the title compound as a light yellow solid.

C. 4-Hydroxy-7-methylindan-5-carbaldehyde

The title compound is prepared analogously to Example 1, Step K.

D. Methanesulfonic acid 5-[3-hydroxy-4-(1,1,4-tri-oxo-1,2,5-thiadiazolidin-2-yl)-benzyl]-7-methyl-indan-4-yl ester The title compound is prepared analogously to Example 39, Steps A to C, using triethylamine in place of pyridine: MS (M−H)$^-$=465. $^1$H NMR (CD$_3$OD) δ 2.05 (quintet, J=8 Hz, 2H), 2.15 (s, 3H), 2.81 (t, J=8 Hz, 2H), 3.00 (t, J=8 Hz, 2H), 3.21 (s, 3H), 3.94 (s, 2H), 4.24 (s, 2H), 6.63 (d, J=8 Hz, 1H), 6.65 (s, 1H), 6.78 (s, 1H), 7.27 (d, J=8 Hz, 1H).

EXAMPLE 46

Methanesulfonic acid 6-[3-hydroxy-4-(1,1,4-trioxo-1,2,5-thiadiazolidin-2-yl)-benzyl]-indan-5-yl ester

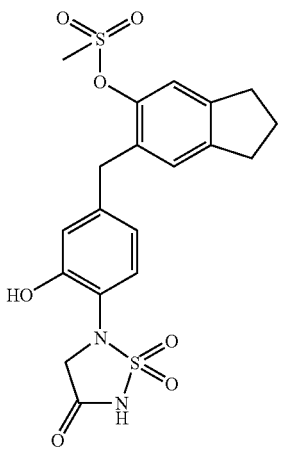

A. 6-Bromoindan-5-ol

To a solution of 5-indanol (6.32 g, 47 mmol) in DMF (20 mL) is added NBS (8.38 g, 47 mmol) and the mixture is stirred at ambient temperature for 1 h. Water is added and the mixture is then extracted with EtOAc. The organic layer is washed with 1N HCl solution and brine, dried with Na$_2$SO$_4$ and concentrated to give the title compound and it is used in the next step without purification.

B. 5-Bromo-6-(4-methoxybenzyloxy)-indan

The title compound is prepared analogously to Example 40, Step A.

C. 6-(4-Methoxybenzyloxy)-indan-5-carbaldehyde

The title compound is prepared analogously to Example 45, Step B.

D. 6-Hydroxyindan-5-carbaldehyde

The title compound is prepared analogously to Example 4, Step A.

E. Methanesulfonic acid 6-[3-hydroxy-4-(1,1,4-tri-oxo-1,2,5-thiadiazolidin-2-yl)-benzyl]-indan-5-yl ester The title compound is prepared analogously to Example 39, Steps A to C: $^1$H NMR (CD$_3$OD) δ 2.10 (quintet, J=8 Hz, 2H), 2.86 (t, J=8 Hz, 2H), 2.90 (t, J=8 Hz, 2H), 3.12 (s, 3H), 3.94 (s, 2H), 4.29 (s, 2H), 6.70 (d, J=8 Hz, 1H), 6.72 (s, 1H), 7.09 (s, 1H), 7.21 (s, 1H), 7.32 (d, J=8 Hz, 1H). MS (M−H)$^-$= 451.

EXAMPLE 47

N-{2-[4-(1,1-dioxido-4-oxo-1,2,5-thiadiazolidin-2-yl)-3-hydroxybenzyl]-1,4-dimethylphenyl}sulfamide

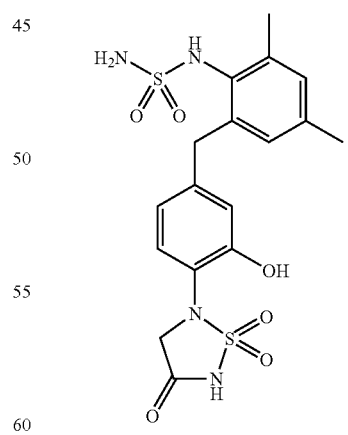

The title compound is prepared analogously to Example 6, starting from 5-[4-(2-amino-3,5-dimethylbenzyl)-2-benzyloxy-phenyl]-1,1-dioxo-2-(2-trimethylsilanyl -ethyl)-1,2,5-thiadiazolidin-3-one (intermediate from Example 37-14): MS (M−H)⁻=439.

EXAMPLE 48

N-{2-[4-(1,1-dioxido-4-oxo-1,2,5-thiadiazolidin-2-yl)-3-hydroxybenzyl]-1-methyl-4-chlorophenyl}sulfamide

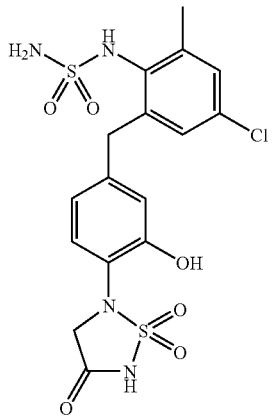

The title compound is prepared analogously to Example 6 from 5-[4-(2-amino-5-chloro-3-methylbenzyl)-2-benzyloxyphenyl]-1,1-dioxo-2-(2-trimethylsilanyl -ethyl)-1,2,5-thiadiazolidin-3-one (intermediate from Example 37-12): MS (M−H)⁻=459.

EXAMPLE 49

N-{2-[4-(1,1-dioxido-4-oxo-1,2,5-thiadiazolidin-2-yl)-3-hydroxybenzyl]-4-ethylphenyl}sulfamide

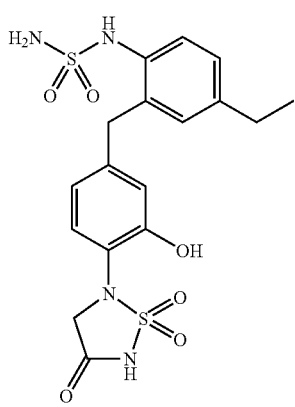

The title compound is prepared analogously to Example 6 from 5-[4-(2-amino-5-ethyl)-2-benzyloxyphenyl]-1,1-di-oxo-2-(2-trimethylsilanyl-ethyl)-1,2,5-thiadiazolidin-3-one (intermediate from Example 42-2): MS (M−H)⁻=439.

EXAMPLE 50

Methanesulfonic acid 2-[3-hydroxy-4-(1,1,4-trioxo-1,2,5-thiadiazolidin-2-yl)-benzyl]-6-isopropylphenyl ester

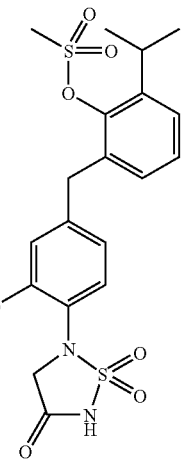

A. 2-Hydroxy-3-isopropylbenzoic acid methyl ester

To a solution of 2-hydroxy-3-isopropylbenzoic acid (4.5 g, 25 mmol) in MeOH (75 mL) is added 10 drops of sulfuric acid and the mixture is heated in an oil bath at 45° C. for 18 h. Extra sulfuric acid (10 drops) is added and the mixture is heated again at 60° C. for 18 h. Solvent is evaporated under reduced pressure and the residue is dissolved in EtOAc. The organic phase is then washed with saturated NaHCO₃ (4×), water (1×) and brine and is dried with Na₂SO₄ and MgSO₄, and concentrated. The residue is purified by flash column chromatography to give the title compound as an oil.

B. Methanesulfonic acid 2-[3-hydroxy-4-(1,1,4-trioxo-1,2,5-thiadiazolidin-2-yl)-benzyl]-6-isopropylphenyl ester The title compound is prepared analogously to Example 18, with the exception that CsF is used in place of TBAF for the removal of TMS-ethyl group (general procedure outlined in Example 10, Step F): MS (M−H)⁻=453.

EXAMPLE 51

Methanesulfonic acid 2-[3-hydroxy-4-(1,1,4-trioxo-1,2,5-thiadiazolidin-2-yl)-benzyl]-5-methylphenyl ester

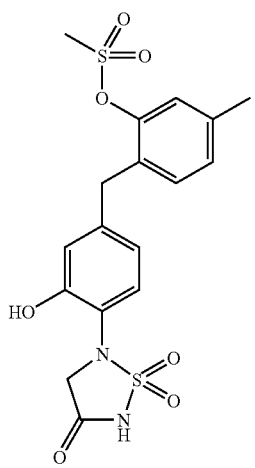

A. 2-Hydroxy-4-methylbenzoic acid methyl ester

To a solution of 2-hydroxy-4-methylbenzoic acid (1.52 g, 10 mmol) in toluene (6 mL) and methanol (2 mL) at 0° C. is added trimethylsilyldiazomethane (2 M in hexane, 6 mL, 12 mmol) dropwise. The mixture is then warmed up to ambient temperature and it is stirred for 2 h. The solvent is removed under reduced pressure and the residue is purified by flash chromatography to give the title compound as a colorless oil.

B. Methanesulfonic acid 2-chloro-6-[3-hydroxy-4-(1,1,4-trioxo-1,2,5-thiadiazolidin-2-yl)-benzyl]-phenyl ester The title compound is prepared analogously to Example 50, Step B: MS (M−H)⁻=445.

EXAMPLE 52

The following compounds are prepared analogously to Example 51 with appropriate staring material.

EXAMPLE 53

N-{2-Chloro-6-[3-hydroxy-4-(1,1,4-trioxo-1,2,5-thiadiazolidin-2-yl)-benzyl]-phenyl}-methanesulfonamide

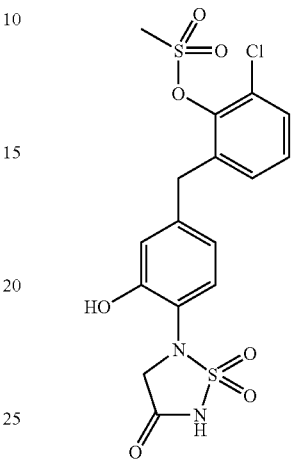

A. 2-tert-Butoxycarbonylamino-3-chlorobenzoic acid

The title compound is prepared analogously to Example 3, Step A, starting from 2-amino-3-chlorobenzoic acid methyl ester except that LiHMDS is added as a base.

B. (2-Chloro-6-hydroxymethylphenyl)-carbamic acid tert-butyl ester

The title compound is prepared analogously to Example 13, Step C.

C. N-{2-Chloro-6-[3-hydroxy-4-(1,1,4-trioxo-1,2,5-thiadiazolidin-2-yl)-benzyl]-phenyl}-methanesulfonamide The title compound is prepared analogously to Example 7, Steps B and C, with the exception that CsF is used in place of

| Example | Chemical Name | MS (m/z) |
|---|---|---|
| 52-1 | Methanesulfonic acid 2-chloro-6-[3-hydroxy-4-(1,1,4-trioxo-1,2,5-thiadiazolidin-2-yl)-benzyl]-phenyl ester | (M − H)⁻ = 445 |
| 52-2 | Methanesulfonic acid 5-chloro-2-[3-hydroxy-4-(1,1,4-trioxo-1,2,5-thiadiazolidin-2-yl)-benzyl]-phenyl ester | (M − H)⁻ = 445 |
| 52-3 | Methanesulfonic acid 2-[3-hydroxy-4-(1,1,4-trioxo-1,2,5-thiadiazolidin-2-yl)-benzyl]-5-methoxyphenyl ester | (M − H)⁻ = 441 |
| 52-4 | Methanesulfonic acid 2-[3-hydroxy-4-(1,1,4-trioxo-1,2,5-thiadiazolidin-2-yl)-benzyl]-6-methoxyphenyl ester | (M − H)⁻ = 441 |

TBAF for the removal of TMS-ethyl group (general procedure outlined in Example 10; Step F); MS (M−H)⁻=444.

EXAMPLE 54

Methanesulfonic acid 2-[3-hydroxy-4-(1,1,4-trioxo-1,2,5-thiadiazolidin-2-yl)-benzyl]-4,6-dimethylphenyl ester

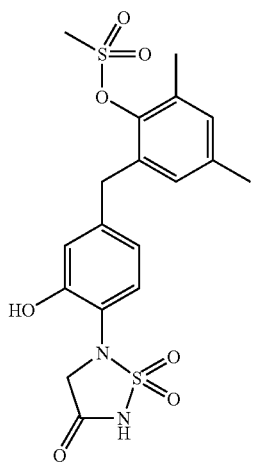

The title compound is prepared analogously to Example 50 from 2-hydroxy-3,5-dimethylbenzoic acid (*Synthesis*, 1984, 758-760): MS (M−H)⁻=439.

EXAMPLE 55

Benzoic acid 5-benzyl-2-(1,1,4-trioxo-1,2,5-thiadiazolidin-2-yl)-phenyl ester

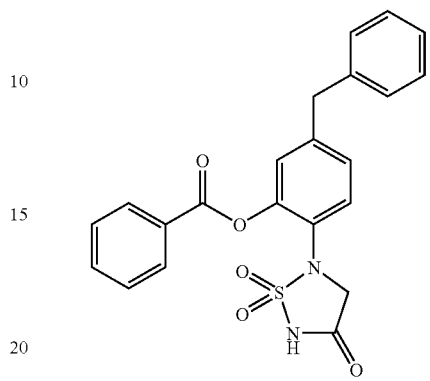

To a solution of 5-(4-benzyl-2-hydroxyphenyl)-1,1-dioxo-1,2,5-thiadiazolidin-3-one (45 mg, 0.141 mmol) in DMF (0.2 mL) is added KOtBu (1.0 M in THF, 0.17 mL, 0.17 mmol). After it is stirred at ambient temperature for 5 min., benzoyl chloride (35 mg, 0.254 mmol) is added. After it is stirred at ambient temperature for 10 min., the reaction is quenched with 1N HCl solution. The residue is then purified by prep. HPLC using $CH_3CN$ (0.1% TFA)/water (5-70%) to give the title compound: MS (M−H)⁻=421.

EXAMPLE 56

The following compounds are prepared analogously to Example 55 using appropriate starting materials with either benzoyl chloride or benzoic anhydride. Example 56-7 and 56-13 use Boc-D,L-valine hydroxysuccinimide ester in place of benzoyl chloride and Example 56-10 uses Boc-L-valine hydroxysuccinimide ester. For Example 56-24, isopropyl chloroformate is used. For Examples 56-12, 56-14 and 56-15, methyl chloroformate is used. Example 56-18 is a by-product of Example 56-16 and Example 56-21 is a by-product of Example 56-22.

| Example | Chemical Name | MS (m/z) |
|---|---|---|
| 56-1 | Benzoic acid 5-(2-methanesulfonyloxybenzyl)-2-(1,1,4-trioxo-1,2,5-thiadiazolidin-2-yl)-phenyl ester | (M − H)⁻ = 515 |
| 56-2 | Benzoic acid 5-(2-methanesulfonyloxy-5-methylbenzyl)-2-(1,1,4-trioxo-1,2,5-thiadiazolidin-2-yl)-phenyl ester | (M − H)⁻ = 529 |
| 56-3 | Benzoic acid 5-(2-methanesulfonylamino-5-methylbenzyl)-2-(1,1,4-trioxo-1,2,5-thiadiazolidin-2-yl)-phenyl ester | (M − H)⁻ = 528 |
| 56-4 | Benzoic acid 5-(2-methanesulfonylaminobenzyl)-2-(1,1,4-trioxo-1,2,5-thiadiazolidin-2-yl)-phenyl ester | (M − H)⁻ = 514 |
| 56-5 | Benzoic acid 5-[2-(benzoylmethanesulfonylamino)-5-methylbenzyl]-2-(1,1,4-trioxo-1,2,5-thiadiazolidin-2-yl)-phenyl ester | (M − H)⁻ = 632 |
| 56-6 | Benzoic acid 5-[2-(benzoylmethanesulfonylamino)-benzyl]-2-(1,1,4-trioxo-1,2,5-thiadiazolidin-2-yl)-phenyl ester | (M − H)⁻ = 618 |
| 56-7 | 2-Amino-3-methylbutyric acid 5-(2-methanesulfonyloxybenzyl)-2-(1,1,4-trioxo-1,2,5-thiadiazolidin-2-yl)-phenyl ester | (M − H)⁻ = 510 |
| 56-8 | Benzoic acid 5-(5-chloro-2-methanesulfonylamino-3-methylbenzyl)-2-(1,1,4-trioxo-1,2,5-thiadiazolidin-2-yl)-phenyl ester | (M − H)⁻ = 563 |
| 56-9 | Benzoic acid 5-(2-methanesulfonylamino-3,5-dimethylbenzyl)-2-(1,1,4-trioxo-1,2,5-thiadiazolidin-2-yl)-phenyl ester | (M − H)⁻ = 542 |

| Example | Chemical Name | MS (m/z) |
|---|---|---|
| 56-10 | 2-Amino-3-methylbutyric acid 5-(2-methanesulfonyloxy-5-methylbenzyl)-2-(1,1,4-trioxo-1,2,5-thiadiazolidin-2-yl)-phenyl ester | (M − H)⁻ = 524 |
| 56-11 | Benzoic acid 5-(2-methanesulfonyloxy-3,5-dimethylbenzyl)-2-(1,1,4-trioxo-1,2,5-thiadiazolidin-2-yl)-phenyl ester | (M − H)⁻ = 543 |
| 56-12 | Methanesulfonic acid 2-[3-methoxycarbonyloxy-4-(1,1,4-trioxo-1,2,5-thiadiazolidin-2-yl)-benzyl]-4-methylphenyl ester | (M − H)⁻ = 511 |
| 56-13 | 2-Amino-3-methylbutyric acid 5-(2-methanesulfonylamino-benzyl)-2-(1,1,4-trioxo-1,2,5-thiadiazolidin-2-yl)-phenyl ester | (M − H)⁻ = 509 |
| 56-14 | 2-(1,1-dioxido-4-oxo-1,2,5-thiadiazolidin-2-yl)-5-{2-[(methoxycarbonyl)(methylsulfonyl)amino]-3,5-dimethylbenzyl}phenyl methyl carbonate | (M − H)⁻ = 554 |
| 56-15 | Carbonic acid 5-(2-methanesulfonylamino-3,5-dimethylbenzyl)-2-(1,1,4-trioxo-1,2,5-thiadiazolidin-2-yl)-phenyl ester methyl ester | (M − H)⁻ = 496 |
| 56-16 | Benzoic acid 5-(2-methanesulfonylamino-4-methylbenzyl)-2-(1,1,4-trioxo-1,2,5-thiadiazolidin-2-yl)-phenyl ester | (M − H)⁻ = 528 |
| 56-17 | Benzoic acid 5-(2-methanesulfonyloxy-4-methylbenzyl)-2-(1,1,4-trioxo-1,2,5-thiadiazolidin-2-yl)-phenyl ester | (M − H)⁻ = 529 |
| 56-18 | Benzoic acid 5-[2-(benzoylmethanesulfonylamino)-4-methylbenzyl]-2-(1,1,4-trioxo-1,2,5-thiadiazolidin-2-yl)-phenyl ester | (M − H)⁻ = 632 |
| 56-19 | Benzoic acid 5-(2-methanesulfonyloxy-3-methylbenzyl)-2-(1,1,4-trioxo-1,2,5-thiadiazolidin-2-yl)-phenyl ester | (M − H)⁻ = 529 |
| 56-20 | Benzoic acid 5-(5-chloro-2-methanesulfonyloxy-3-methylbenzyl)-2-(1,1,4-trioxo-1,2,5-thiadiazolidin-2-yl)-phenyl ester | (M − H)⁻ = 564 |
| 56-21 | Benzoic acid 5-[2-(benzoylmethanesulfonylamino)-3-methylbenzyl]-2-(1,1,4-trioxo-1,2,5-thiadiazolidin-2-yl)-phenyl ester | (M − H)⁻ = 632 |
| 56-22 | Benzoic acid 5-(2-methanesulfonylamino-3-methylbenzyl)-2-(1,1,4-trioxo-1,2,5-thiadiazolidin-2-yl)-phenyl ester | (M − H)⁻ = 528 |
| 56-23 | 2-Methylbenzoic acid 5-(2-methanesulfonyloxy-5-methylbenzyl)-2-(1,1,4-trioxo-1,2,5-thiadiazolidin-2-yl)-phenyl ester | (M − H)⁻ = 543 |
| 56-24 | Methanesulfonic acid 2-[3-isopropoxycarbonyloxy-4-(1,1,4-trioxo-1,2,5-thiadiazolidin-2-yl)-benzyl]-4-methyl-phenyl ester | (M − H)⁻ = 511 |

EXAMPLE 57

5-(4-Benzyl-2-hydroxy-6-methylphenyl)-1,1-dioxo-1,2,5-thiadiazolidin-3-one

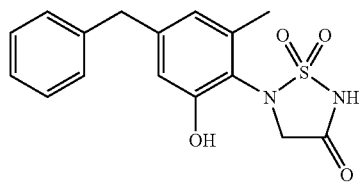

A. 1-Benzyloxy-3-methyl-2-nitrobenzene

The title compound is prepared analogously to Example 1, Step A, from 3-methyl-2-nitrophenol.

B. 2-Benzyloxy-6-methylphenylamine

To a solution of 1-benzyloxy-3-methyl-2-nitrobenzene (5.0 g, 20.6 mmol) in EtOAc (150 mL) is added $SnCl_2$ (23.2 g, 103 mmol) and the mixture is heated at 60° C. for 72 h. The mixture is then filtered and to the filtrate is added saturated $NaHCO_3$ and solid $Na_2CO_3$. It is then filtered again. EtOAc layer is separated and washed with brine, dried and concentrated. The residue is purified by flash chromatography to give the title compound as a yellow oil.

C. 2-Benzyloxy-4-bromo-6-methylphenylamine

To a mixture of 2-benzyloxy-6-methylphenylamine (3.4 g, 16 mmol) in MeOH (50 mL) and AcOH (20 mL) is added $Br_2$ (0.82 mL, 16 mmol) in AcOH (10 mL) at 0° C. The mixture is then stirred at ambient temperature for 18 h. The solvent is then removed under reduced pressure. Then $K_2CO_3$ solution is added followed by EtOAc. The organic layer is washed with water and brine, dried and concentrated. The residue is then purified by flash chromatography to give the title compound as a red liquid.

D. 5-(2-Benzyloxy-4-bromo-6-methylphenyl)-1,1-dioxo-1,2,5-thiadiazolidin-3-one The title compound is prepared analogously to Example 26, Steps D to G.

E. 5-(4-Benzyl-2-benzyloxy-6-methylphenyl)-1,1-dioxo-1,2,5-thiadiazolidin-3-one The title compound is prepared analogously to Example 30, Step E with the exception that beta-benzyl-9-BBN is used in place of (4,4,5,5-tetramethyl-[1,3,2]dioxaborolan-2-yl)-benzonitrile.

F. 5-(4-Benzyl-2-hydroxy-6-methylphenyl)-1,1-dioxo-1,2,5-thiadiazolidin-3-one

The title compound is prepared analogously to Example 1, Step K: MS (M−H)⁻=331.

The table below shows the inhibitory activity (IC50 values) of representative compounds of the invention to human PTP-1B.

| Compound | IC50 (nM) |
| --- | --- |
| Example No. 52-1 | 126 nM |
| Example No. 52-3 | 133 nM |

What is claimed is:

1. A compound of the formula

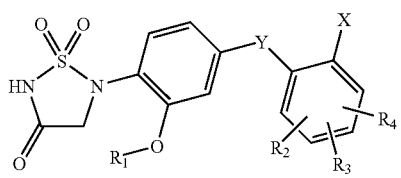

(I)

wherein

R$_1$ is hydrogen, —C(O)R$_5$, —C(O)NR$_6$R$_7$ or —C(O)OR$_8$ in which

R$_5$ and R$_6$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_7$ and R$_8$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_2$, R$_3$ and R$_4$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or R$_2$ and R$_3$ combined are alkylene which together with the ring atoms to which they are attached form a 5- to 7-membered fused ring provided R$_2$ and R$_3$ are attached to carbon atoms adjacent to each other; or R$_2$ and R$_3$ combined together with the carbon atom to which they are attached form a fused 5- to 6-membered aromatic or heteroaromatic ring provided R$_2$ and R$_3$ are attached to carbon atoms adjacent to each other;

X is hydrogen, fluoro, cyano, or free or esterified carboxy; or

X is —NR$_9$C(O)R$_{10}$, —NR$_9$C(O)OR$_{11}$, —NR$_9$S(O)$_2$R$_{12}$, —(CH$_2$)$_m$S(O)$_2$R$_{13}$, —OS(O)$_2$R$_{14}$ or —O$_n$C(O)NR$_{15}$R$_{16}$ in which R$_9$ is hydrogen, lower alkyl, acyl, alkoxycarbonyl or sulfonyl;

R$_{10}$, R$_{11}$, R$_{12}$, R$_{13}$ and R$_{14}$ are, independently from each other, cycloalkyl, aryl, heterocyclyl, aralkyl, heteroaralkyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or R$_{10}$, R$_{12}$ and R$_{13}$ are, independently from each other, —NR$_{17}$R$_{18}$ in which R$_{17}$ and R$_{18}$ are, independently from each other, hydrogen, alkyl, cycloalkyl, aralkyl, aryl or heterocyclyl; or R$_{17}$ and R$_{18}$ combined are alkylene which together with the nitrogen atom to which they are attached form a 4- to 7-membered ring;

R$_{15}$ and R$_{16}$ are, independently from each other, hydrogen, alkyl, cycloalkyl, aralkyl, aryl or heterocyclyl; or R$_{15}$ and R$_{16}$ combined are alkylene which together with the nitrogen atom to which they are attached form a 4- to 7-membered ring;

m and n are, independently from each other, zero or an integer of 1; or

C—X is replaced by nitrogen;

Y is CH$_2$, O or S;

or a pharmaceutically acceptable salt thereof.

2. The compound according to claim 1, wherein

Y is CH$_2$;

or a pharmaceutically acceptable salt thereof.

3. The compound according to claim 2 of the formula

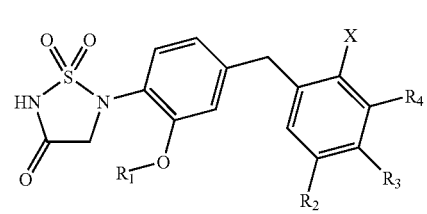

(IA)

wherein

R$_1$ is hydrogen, —C(O)R$_5$, —C(O)NR$_6$R$_7$ or —C(O)OR$_8$ in which

R$_5$ and R$_6$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_7$ and R$_8$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_2$, $R_3$ and $R_4$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or ($C_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or $R_2$ and $R_3$ combined are alkylene which together with the ring atoms to which they are attached form a 5- to 7-membered fused ring; or $R_2$ and $R_3$ combined together with the carbon atom to which they are attached form a fused 5- to 6-membered aromatic or heteroaromatic ring;

X is cyano; or

X is —$NR_9C(O)R_{10}$, —$NR_9C(O)OR_{11}$, —$NR_9S(O)_2R_{12}$, —$(CH_2)_mS(O)_2R_{13}$ or —$OS(O)_2R_{14}$ in which $R_9$ is hydrogen or lower alkyl;

$R_{10}$, $R_{11}$, $R_{12}$, $R_{13}$ and $R_{14}$ are, independently from each other, cycloalkyl, aryl, heterocyclyl, aralkyl, heteroaralkyl or ($C_{1-8}$alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or $R_{10}$, $R_{12}$ and $R_{13}$ are, independently from each other, —$NR_{17}R_{18}$ in which $R_{17}$ and $R_{18}$ are, independently from each other, hydrogen, alkyl, cycloalkyl, aralkyl, aryl or heterocyclyl; or $R_{17}$ and $R_{18}$ combined are alkylene which together with the nitrogen atom to which they are attached form a 4- to 7-membered ring;

m is zero; or

C—X is replaced by nitrogen;

or a pharmaceutically acceptable salt thereof.

4. The compound according to claim 3, wherein

X is cyano; or

X is —$NR_9S(O)_2R_{12}$ or —$OS(O)_2R_{14}$ in which $R_9$ is hydrogen or lower alkyl;

$R_{12}$ and $R_{14}$ are, independently from each other, cycloalkyl, aryl, heterocyclyl, aralkyl, heteroaralkyl or ($C_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy;

or a pharmaceutically acceptable salt thereof.

5. The compound according to claim 4, wherein $R_9$ is hydrogen;

or a pharmaceutically acceptable salt thereof.

6. The compound according to claim 5, wherein $R_{12}$ and $R_{14}$ are, independently from each other, monocyclic aryl or $C_{(1-4)}$alkyl;

or a pharmaceutically acceptable salt thereof.

7. The compound according to claim 6, wherein $R_1$ is hydrogen or —$C(O)R_5$ in which $R_5$ is monocyclic aryl;

or a pharmaceutically acceptable salt thereof.

8. The compound according to claim 4, wherein $R_2$, $R_3$ and $R_4$ are, independently from each other, hydrogen, halogen, hydroxy, monocyclic aryl, $C_{(1-4)}$alkoxy or $C_{(1-4)}$alkyl optionally substituted with at least one halogen;

or a pharmaceutically acceptable salt thereof.

9. The compound according to claim 8, wherein $R_9$ is hydrogen;

or a pharmaceutically acceptable salt thereof.

10. The compound according to claim 9, wherein $R_{12}$ and $R_{14}$ are, independently from each other, monocyclic aryl or $C_{(1-4)}$alkyl;

or a pharmaceutically acceptable salt thereof.

11. The compound according to claim 10, wherein $R_1$ is hydrogen or —$C(O)R_5$ in which $R_5$ is monocyclic aryl;

or a pharmaceutically acceptable salt thereof.

12. The compound according to claim 1 selected from the group consisting of:

5-(4-Benzyl-2-hydroxyphenyl)-1,1-dioxo-1,2,5-thiadiazolidin-3-one;

5-[2-Hydroxy-4-(3-hydroxybenzyl)-phenyl]-1,1-dioxo-1,2,5-thiadiazolidin-3-one;

5-[2-Hydroxy-4-(3-methoxybenzyl)-phenyl]-1,1-dioxo-1,2,5-thiadiazolidin-3-one;

5-[4-(2-Fluoro-3-trifluoromethylbenzyl)-2-hydroxyphenyl]-1,1-dioxo-1,2,5-thiadiazolidin-3-one;

2-[3-Hydroxy-4-(1,1,4-trioxo-1,2,5-thiadiazolidin-2-yl)-benzyl]-benzonitrile;

5-[4-(2-Fluorobenzyl)-2-hydroxyphenyl]-1,1-dioxo-1,2,5-thiadiazolidin-3-one;

5-(2-Hydroxy-4-naphthalen-2-ylmethylphenyl)-1,1-dioxo-1,2,5-thiadiazolidin-3-one;

5-[2-Hydroxy-4-(3-trifluoromethylbenzylphenyl]-1,1-dioxo-1,2,5-thiadiazolidin-3-one;

5-[2-Hydroxy-4-(2-methylbenzyl)phenyl]-1,1-dioxo-1,2,5-thiadiazolidin-3-one;

5-[4-(4-Fluorobenzyl)-2-hydroxyphenyl]-1,1-dioxo-1,2,5-thiadiazolidin-3-one;

3-[3-Hydroxy-4-(1,1,4-trioxo-1,2,5-thiadiazolidin-2-yl)-benzyl]-benzoic acid methyl ester;

5-(4-Biphenyl-3-ylmethyl-2-hydroxyphenyl)-1,1-dioxo-1,2,5-thiadiazolidin-3-one;

5-[4-(3-Fluoro-4-methylbenzyl)-2-hydroxyphenyl]-1,1-dioxo-1,2,5-thiadiazolidin-3-one;

5-[2-Hydroxy-4-(4-methylbenzyl)phenyl]-1,1-dioxo-1,2,5-thiadiazolidin-3-one;

5-[2-Hydroxy-4-(4-hydroxybenzyl)phenyl]-1,1-dioxo-1,2,5-thiadiazolidin-3-one;

5-[4-(3-Fluorobenzyl)-2-hydroxyphenyl]-1,1-dioxo-1,2,5-thiadiazolidin-3-one;

5-[4-(4-tert-Butylbenzyl)-2-hydroxyphenyl]-1,1-dioxo-1,2,5-thiadiazolidin-3-one;

5-[4-{2-Benzenesulfonylmethylbenzyl)-2-hydroxyphenyl]-1,1-dioxo-1,2,5-thiadiazolidin-3-one;

5-[2-Hydroxy-4-(3-methylbenzyl)phenyl]-1,1-dioxo-1,2,5-thiadiazolidin-3-one;
{2-[3-Hydroxy-4-(1,1,4-trioxo-1,2,5-thiadiazolidin-2-yl)-benzyl]-phenyl}-carbamic acid tert-butyl ester;
N-{2-[3-Hydroxy-4-(1,1,4-trioxo-1,2,5-thiadiazolidin-2-yl)-benzyl]-phenyl}-C-phenyl-methanesulfonamide;
N-{2-[3-Hydroxy-4-(1,1,4-trioxo-1,2,5-thiadiazolidin-2-yl)-benzyl]-phenyl}-benzenesulfonamide;
Ethanesulfonic acid {2-[3-hydroxy-4-(1,1,4-trioxo-1,2,5-thiadiazolidin-2-yl)-benzyl]-phenyl}-amide;
Propane-1-sulfonic acid {2-[3-hydroxy-4-(1,1,4-trioxo-1,2,5-thiadiazolidin-2-yl)-benzyl]-phenyl}-amide;
Butane-1-sulfonic acid {2-[3-hydroxy-4-(1,1,4-trioxo-1,2,5-thiadiazolidin-2-yl)-benzyl]-phenyl}-amide;
C-Cyclohexyl-N-{2-[3-hydroxy-4-(1,1,4-trioxo-1,2,5-thiadiazolidin-2-yl)-benzyl]phenyl}-methanesulfonamide;
N-{2-[3-Hydroxy-4-(1,1,4-trioxo-1,2,5-thiadiazolidin-2-yl)-benzyl]-phenyl}-methanesulfonamide;
N-{2-[3-Hydroxy-4-(1,1,4-trioxo-1,2,5-thiadiazolidin-2-yl)-benzyl]-phenyl}-4-isopropylbenzenesulfonamide;
N-{2-[3-Hydroxy-4-(1,1,4-trioxo-1,2,5-thiadiazolidin-2-yl)-benzyl]phenyl}-aminosulfonamide;
N-{3-[3-Hydroxy-4-(1,1,4-trioxo-1,2,5-thiadiazolidin-2-yl)-benzyl]-naphthalen-2-yl}-methanesulfonamide;
N-{2-[3-Hydroxy-4-(1,1,4-trioxo-1,2,5-thiadazolidin-2-yl)-benzyl]phenyl}-acetamide;
4-tert-Butyl-N-{2-[3-hydroxy-4-(1,1,4-trioxo-1,2,5-thiadiazolidin-2-yl)-benzyl]-phenyl}-benzamide;
N-{2-[3-Hydroxy-4-(1,1,4-trioxo-1,2,5-thiadiazolidin-2-yl)-benzyl]phenyl}-benzamide;
5-[4-(4-Ethylpyridin-2-ylmethyl)-2-hydroxyphenyl]-1,1-dioxo-1,2,5-thiadiazolidin-3-one;
5-[4-(6-Methoxypyridin-2-ylmethyl)-2-hydroxyphenyl]-1,1-dioxo-1,2,5-thiadiazolidin-3-one;
5-(2-Hydroxy-4-pyridin-2-ylmethylphenyl)-1,1-dioxo-1,2,5-thiadiazolidin-3-one;
5-[2-Hydroxy-4-(2-methanesulfonylbenzyl)-phenyl]-1,1-dioxo 1,2,5-thiadiazolidin-3-one;
N-{2-[3-Hydroxy-4-(1,1,4-trioxo-1,2,5-thiadiazolidin-2-yl)-benzyl]phenyl}-N-methylmethanesulfonamide;
5-[2-Hydroxy-4-(2-methanesulfonylmethylbenzyl)-phenyl]-1,1-dioxo-1,2,5-thiadiazolidin-3-one;
5-{4-(3-Methansulfonylphenyl)methyl-2-hydroxyphenyl}-1,1-dioxo-1,2,5-thiadiazolidin-3-one;
C-{2-[3-Hydroxy-4-(1,1,4-trioxo-1,2,5-thiadiazolidin-2-yl)-benzyl]-phenyl}-N,N-dimethylmethanesulfonamide;
Methanesulfonic acid 2-[3-hydroxy-4-(1,1,4-trioxo-1,2,5-thiadiazolidin-2-yl)-benzyl]-phenyl ester;
Methanesulfonic acid 3-[3-hydroxy-4-(1,1,4-trioxo-1,2,5-thiadiazolidin-2-yl)-benzyl]-naphthalen-2-yl ester;
Methanesulfonic acid 2-[3-hydroxy-4-(1,1,4-trioxo-1,2,5-thiadiazolidin-2-yl)-benzyl]-naphthalen-1-yl ester;
Methanesulfonic acid 2-[3-hydroxy-4-(1,1,4-trioxo-1,2,5-thiadiazolidin-2-yl)-benzyl]-4-methylphenyl ester;
Methanesulfonic acid 1-[3-hydroxy-4-(1,1,4-trioxo-1,2,5-thiadiazolidin-2-yl)-benzyl]-naphthalen-2-yl ester;
Methanesulfonic acid 2-[3-hydroxy-4-(1,1,4-trioxo-1,2,5-thiadiazolidin-2-yl)-benzyl]-4-methoxyphenyl ester;
Methanesulfonic acid 2-[3-hydroxy-4-(1,1,4-trioxo-1,2,5-thiadiazolidin-2-yl)-benzyl]-6-methylphenyl ester;
Ethanesulfonic acid 2-[3-hydroxy-4-(1,1,4-trioxo-1,2,5-thiadiazolidin-2-yl)-benzyl]-4-methylphenyl ester;
Propane-1-sulfonic acid 2-[3-hydroxy-4-(1,1,4-trioxo-1,2,5-thiadiazolidin-2-yl)-benzyl]-4-methylphenyl ester;
Methanesulfonic acid 4-chloro-2-[3-hydroxy-4-(1,1,4-trioxo-1,2,5-thiadiazolidin-2-yl)-benzyl]-phenyl ester;
Methanesulfonic acid 2-[3-hydroxy-4-(1,1,4-trioxo-1,2,5-thiadiazolidin-2-yl)-benzyl]-5-methylphenyl ester;
Methanesulfonic acid 4-chloro-2-[3-hydroxy-4-(1,1,4-trioxo-1,2,5-thiadiazolidin-2-yl)-benzyl]-6-methylphenyl ester;
Ethanesulfonic acid 2-[3-hydroxy-4-(1,1,4-trioxo-1,2,5-thiadiazolidin-2-yl)-benzyl]-phenyl ester;
Propane-1-sulfonic acid 2-[3-hydroxy-4-(1,1,4-trioxo-1,2,5-thiadiazolidin-2-yl)-benzyl]-phenyl ester;
5-[4-(2-Fluoro-4-methylbenzyl)-2-hydroxyphenyl]-1,1-dioxo-1,2,5-thiadiazolidin-3-one;
3-[3-Hydroxy-4-(1,1,4-trioxo-1,2,5-thiadiazolidin-2-yl)-benzyl]-N-methylbenzamide potassium salt;
3-[3-Hydroxy-4-(1,1,4-trioxo-1,2,5-thiadiazolidin-2-yl)-benzyl]-benzoic acid dipotassium salt;
2-[3-Hydroxy-4-(1,1,4-trioxo-1,2,5-thiadiazolidin-2-yl)-benzyl]-benzoic acid;
5-[4-(2,5-Difluorobenzyl)-2-hydroxyphenyl]-1,1-dioxo-1,2,5-thiadiazolidin-3-one;
5-[4-(3-Ethylbenzyl)-2-hydroxyphenyl]-1,1-dioxo-1,2,5-thiadiazolidin-3-one;
5-(2-Hydroxy-4-phenoxyphenyl)-1,1-dioxo-1,2,5-thiadiazolidin-3-one potassium salt;
2-Hydroxy-6-[3-hydroxy-4-(1,1,4-trioxo-1,2,5-thiadiazolidin-2-yl)-benzyl]-benzonitrile;
2-[3-Hydroxy-4-(1,1,4-trioxo-1,2,5-thiadiazolidin-2-yl)-benzyl]-4-trifluoromethylbenzonitrile;
2-[3-Hydroxy-4-(1,1,4-trioxo-1,2,5-thiadiazolidin-2-yl)-benzyl]-4-methylbenzonitrile;
2-[3-Hydroxy-4-(1,1,4-trioxo-1,2,5-thiadiazolidin-2-yl)-benzyl]-6-methyl-benzonitrile;
2-[3-Hydroxy-4-(1,1,4-trioxo-1,2,5-thiadiazolidin-2-yl)-benzyl]-4-trifluoromethylbenzonitrile;
5-(2-Hydroxy-4-phenylsulfanylphenyl)-1,1-dioxo-1,2,5-thiadiazolidin-3-one;
2-[3-Hydroxy-4-(1,1,4-trioxo-1,2,5-thiadiazolidin-2-yl)-phenylsulfanyl]-4-trifluoromethylbenzonitrile;
2-[3-Hydroxy-4-(1,1,4-trioxo-1,2,5-thiadiazolidin-2-yl)-phenylsulfanyl]-6-trifluoromethylbenzonitrile;
Methanesulfonic acid 2-[3-diethylcarbamoyloxy-4-(1,1,4-trioxo-1,2,5-thiadiazolidin-2-yl)-benzyl]-phenyl ester;
Methanesulfonic acid 2-[3-isopropoxycarbonyloxy-4-(1,1,4-trioxo-1,2,5-thiadiazolidin-2-yl)-benzyl]-phenyl ester;
N-{4-Chloro-2-[3-hydroxy-4-(1,1,4-trioxo-1,2,5-thiadiazolidin-2-yl)-benzyl]phenyl}-methanesulfonamide;
N-{2-[3-Hydroxy-4-(1,1,4-trioxo-1,2,5-thiadiazolidin-2-yl)-benzyl]-4-methylphenyl}-methanesulfonamide;
N-{4-Fluoro-2-[3-hydroxy-4-(1,1,4-trioxo-1,2,5-thiadiazolidin-2-yl)-benzyl]- phenyl}-methanesulfonamide;
N-{4-Fluoro-2-[3-hydroxy-4-(1,1,4-trioxo-1,2,5-thiadiazolidin-2-yl)-benzyl]-phenyl}-benzenesulfonamide;
Ethanesulfonic acid {4-fluoro-2-[3-hydroxy-4-(1,1,4-trioxo-1,2,5-thiadiazolidin-2-yl)-benzyl]-phenyl}-amide;
Propane-2-sulfonic acid {4-fluoro-2-[3-hydroxy-4-(1,1,4-trioxo-1,2,5-thiadiazolidin-2-yl)-benzyl]-phenyl}-amide;
Propane-1-sulfonic acid {2-[3-hydroxy-4-(1,1,4-trioxo-1,2,5-thiadiazolidin-2-yl)-benzyl]-4-methylphenyl}-amide;
N-{4-Fluoro-2-[3-hydroxy-4-(1,1,4-trioxo-1,2,5-thiadiazolidin-2-yl)-benzyl]phenyl}-C-phenyl-methanesulfonamide;
Ethanesulfonic acid {4-chloro-2-[3-hydroxy-4-(1,1,4-trioxo-1,2,5-thiadiazolidin-2-yl)-benzyl]-phenyl}-amide;

Propane-2-sulfonic acid {4-chloro-2-[3-hydroxy-4-(1,1,4-trioxo-1,2,5-thiadiazolidin-2-yl)-benzyl]-phenyl}-amide;
Propane-1-sulfonic acid {4-chloro-2-[3-hydroxy-4-(1,1,4-trioxo-1,2,5-thiadiazolidin-2-yl)-benzyl]-phenyl}-amide;
Ethanesulfonic acid {4-chloro-2-[3-hydroxy-4-(1,1,4-trioxo-1,2,5-thiadiazolidin-2-yl)-benzyl]-6-methylphenyl}-amide;
N-{2-[3-Hydroxy-4-(1,1,4-trioxo-1,2,5-thiadiazolidin-2-yl)-benzyl]-6-methylphenyl}-methanesulfonamide;
N-{2-[3-Hydroxy-4-(1,1,4-trioxo-1,2,5-thiadiazolidin-2-yl)-benzyl]-4,6-dimethylphenyl}-methanesulfonamide;
Ethanesulfonic acid {2-[3-hydroxy-4-(1,1,4-trioxo-1,2,5-thiadiazolidin-2-yl)-benzyl]-6-methylphenyl}-amide;
Propane-1-sulfonic acid {2-[3-hydroxy-4-(1,1,4-trioxo-1,2,5-thiadiazolidin-2-yl)-benzyl]-6-methylphenyl}-amide;
Ethanesulfonic acid {2-[3-hydroxy-4-(1,1,4-trioxo-1,2,5-thiadiazolidin-2-yl)-benzyl]-4,6-dimethylphenyl}-amide;
N-{4-Chloro-2-[3-hydroxy-4-(1,1,4-trioxo-1,2,5-thiadiazolidin-2-yl)-benzyl]-6-methylphenyl}-methanesulfonamide;
N-{4-Chloro-2-[3-hydroxy-4-(1,1,4-trioxo-1,2,5-thiadiazolidin-2-yl)-benzyl]-6-methylphenyl}-methanesulfonamide;
N-{2-[3-Hydroxy-4-(1,1,4-trioxo-1,2,5-thiadiazolidin-2-yl)-benzyl]-5-methylphenyl}-methanesulfonamide;
N-{2-[3-Hydroxy-4-(1,1,4-trioxo-1,2,5-thiadiazolidin-2-yl)-benzyl]-6-methoxyphenyl}-methanesulfonamide;
N-{5-Chloro-2-[3-hydroxy-4-(1,1,4-trioxo-1,2,5-thiadiazolidin-2-yl)-benzyl]-phenyl}-methanesulfonamide;
Ethanesulfonic acid {2-[3-hydroxy-4-(1,1,4-trioxo-1,2,5-thiadiazolidin-2-yl)-benzyl]-4-methylphenyl}-amide;
Methanesulfonic acid 4-ethyl-2-[3-hydroxy-4-(1,1,4-trioxo-1,2,5-thiadiazolidin-2-yl)-benzyl]-phenyl ester;
Methanesulfonic acid 4-tert-butyl-2-[3-hydroxy-4-(1,1,4-trioxo-1,2,5-thiadiazolidin-2-yl)-benzyl]-phenyl ester;
Diethylcarbamic acid 2-[3-hydroxy-4-(1,1,4-trioxo-1,2,5-thiadiazolidin-2-yl)-benzyl]-4-methylphenyl ester;
Ethanesulfonic acid {4-ethyl-2-[3-hydroxy-4-(1,1,4-trioxo-1,2,5-thiadiazolidin-2-yl)-benzyl]-phenyl}-amide;
Propane-1-sulfonic acid {4-ethyl-2-[3-hydroxy-4-(1,1,4-trioxo-1,2,5-thiadiazolidin-2-yl)-benzyl]-phenyl}-amide;
N-{4-Ethyl-2-[3-hydroxy-4-(1,1,4-trioxo-1,2,5-thiadiazolidin-2-yl)-benzyl]-phenyl}-methanesulfonamide;
N-{4-Benzyl-2-[3-hydroxy-4-(1,1,4-trioxo-1,2,5-thiadiazolidin-2-yl)-benzylphenyl}methanesulfonamide;
N-{3-[3-Hydroxy-4-(1,1,4-trioxo-1,2,5-thiadiazolidin-2-yl)-benzyl]-biphenyl-4-yl}-methanesulfonamide;
N-{2-[3-Hydroxy-4-(1,1,4-trioxo-1,2,5-thiadiazolidin-2-yl)-benzyl]-4-methoxyphenyl}-methanesulfonamide;
Ethanesulfonic acid {2-[3-hydroxy-4-(1,1,4-trioxo-1,2,5-thiadiazolidin-2-yl)-benzyl]-4-methoxyphenyl}-amide;
Propane-1-sulfonic acid {2-[3-hydroxy-4-(1,1,4-trioxo-1,2,5-thiadiazolidin-2-yl)-benzyl]-4-methoxyphenyl}-amide;
Methanesulfonic acid 5-[3-hydroxy-4-(1,1,4-trioxo-1,2,5-thiadiazolidin-2-yl)-benzyl]-7-methylindan-4-yl ester;
Methanesulfonic acid 6-[3-hydroxy-4-(1,1,4-trioxo-1,2,5-thiadiazolidin-2-yl)-benzyl]-indan-5-yl ester;
N-{2-[4-(1,1-dioxido-4-oxo-1,2,5-thiadiazolidin-2-yl)-3-hydroxybenzyl]- 1,4-dimethylphenyl}sulfamide;
N-{2-[4-(1,1-dioxido-4-oxo-1,2,5-thiadiazolidin-2-yl)-3-hydroxybenzyl]-1-methyl-4-chlorophenyl}sulfamide;
N-{2-[4-(1,1-dioxido-4-oxo-1,2,5-thiadiazolidin-2-yl)-3-hydroxybenzyl]-4-ethylphenyl}sulfamide;
Methanesulfonic acid 2-[3-hydroxy-4-(1,1,4-trioxo-1,2,5-thiadiazolidin-2-yl)-benzyl]-6-isopropylphenyl ester;
Methanesulfonic acid 2-[3-hydroxy-4-(1,1,4-trioxo-1,2,5-thiadiazolidin-2-yl)-benzyl]-5-methylphenyl ester;
Methanesulfonic acid 2-chloro-6-[3-hydroxy-4-(1,1,4-trioxo-1,2,5-thiadiazolidin-2-yl)-benzyl]-phenyl ester;
Methanesulfonic acid 5-chloro-2-[3-hydroxy-4-(1,1,4-trioxo-1,2,5-thiadiazolidin-2-yl)-benzyl]-phenyl ester;
Methanesulfonic acid 2-[3-hydroxy-4-(1,1,4-trioxo-1,2,5-thiadiazolidin-2-yl)-benzyl]-5-methoxyphenyl ester;
Methanesulfonic acid 2-[3-hydroxy-4-(1,1,4-trioxo-1,2,5-thiadiazolidin-2-yl)-benzyl]-6-methoxyphenyl ester;
N-{2-Chloro-6-[3-hydroxy-4-(1,1,4-trioxo-1,2,5-thiadiazolidin-2-yl)-benzyl]phenyl}-methanesulfonamide;
Methanesulfonic acid 2-[3-hydroxy-4-(1,1,4-trioxo-1,2,5-thiadiazolidin-2-yl)-benzyl]-4,6-dimethylphenyl ester;
Benzoic acid 5-benzyl-2-(1,1,4-trioxo-1,2,5-thiadiazolidin-2-yl)-phenyl ester;
Benzoic acid 5-(2-methanesulfonyloxybenzyl)-2-(1,1,4-trioxo-1,2,5-thiadiazolidin-2-yl)-phenyl ester;
Benzoic acid 5-(2-methanesulfonyloxy-5-methylbenzyl)-2-(1,1,4-trioxo-1,2,5-thiadiazolidin-2-yl) -phenyl ester;
Benzoic acid 5-(2-methanesulfonylamino-5-methylbenzyl)-2-(1,1,4-trioxo-1,2,5-thiadiazolidin-2-yl)-phenyl ester;
Benzoic acid 5-(2-methanesulfonylaminobenzyl)-2-(1,1,4-trioxo-1,2,5-thiadiazolidin-2-yl)-phenyl ester;
Benzoic acid 5-[2-(benzoylmethanesulfonylamino)-5-methylbenzyl]-2-(1,1,4-trioxo-1,2,5-thiadiazolidin-2-yl)-phenyl ester;
Benzoic acid 5-[2-(benzoylmethanesulfonylamino)-benzyl]-2-(1,1,4-trioxo-1,2,5-thiadiazolidin-2-yl)-phenyl ester;
2-Amino-3-methylbutyric acid 5-(2-methanesulfonyloxybenzyl)-2-(1,1,4-trioxo-1,2,5-thiadiazolidin-2-yl)-phenyl ester;
Benzoic acid 5-(5-chloro-2-methanesulfonylamino-3-methylbenzyl)-2-(1,1,4-trioxo-1,2,5-thiadiazolidin-2-yl)-phenyl ester;
Benzoic acid 5-(2-methanesulfonylamino-3,5-dimethylbenzyl)-2-(1,1,4-trioxo-1,2,5-thiadiazolidin-2-yl)-phenyl ester;
2-Amino-3-methylbutyric acid 5-(2-methanesulfonyloxy-5-methylbenzyl-2-(1,1,4-trioxo-1,2,5-thiadiazolidin-2-yl)-phenyl ester;
Benzoic acid 5-(2-methanesulfonyloxy-3,5-dimethylbenzyl)-2-(1,1,4-trioxo-1,2,5-thiadiazolidin-2-yl)-phenyl ester;
Methanesulfonic acid 2-[3-methoxycarbonyloxy-4-(1,1,4-trioxo-1,2,5-thiadiazolidin-2-yl)-benzyl]-4-methylphenyl ester;
2-Amino-3-methylbutyric acid 5-(2-methanesulfonylamino-benzyl)-2-(1,1,4-trioxo-1,2,5-thiadiazolidin-2-yl)-phenyl ester;
2-(1,1-dioxido-4-oxo-1,2,5-thiadiazolidin-2-yl)-5-{2-[(methoxycarbonyl)(methylsulfonyl)-amino]-3,5-dimethylbenzyl}phenyl methyl carbonate;
Carbonic acid 5-(2-methanesulfonylamino-3,5-dimethylbenzyl)-2-(1,1,4-trioxo-1,2,5-thiadiazolidin-2-yl)-phenyl ester methyl ester;

Benzoic acid 5-(2-methanesulfonylamino-4-methylbenzyl)-2-(1,1,4-trioxo-1,2,5-thiadiazolidin-2-yl)-phenyl ester;

Benzoic acid 5-(2-methanesulfonyloxy-4-methylbenzyl)-2-(1,1,4-trioxo-1,2,5-thiadiazolidin-2-yl)-phenyl ester;

Benzoic acid 5-[2-(benzoylmethanesulfonylamino)-4-methylbenzyl]-2-(1,1,4-trioxo-1,2,5-thiadiazolidin-2-yl)-phenyl ester;

Benzoic acid 5-(2-methanesulfonyloxy-3-methylbenzyl)-2-(1,1,4-trioxo-1,2,5-thiadiazolidin-2-yl)-phenyl ester;

Benzoic acid 5-(5-chloro-2-methanesulfonyloxy-3-methylbenzyl)-2-(1,1,4-trioxo-1,2,5-thiadiazolidin-2-yl)-phenyl ester;

Benzoic acid 5-[2-(benzoylmethanesulfonylamino)-3-methylbenzyl]-2-(1,1,4-trioxo-1,2,5-thiadiazolidin-2-yl)-phenyl ester;

Benzoic acid 5-(2-methanesulfonylamino-3-methylbenzyl)-2-(1,1,4-trioxo-1,2,5-thiadiazolidin-2-yl)-phenyl ester;

2-Methylbenzoic acid 5-(2-methanesulfonyloxy-5-methylbenzyl)-2-(1,1,4-trioxo-1,2,5-thiadiazolidin-2-yl)-phenyl ester; and 5-(4-Benzyl-2-hydroxy-6-methylphenyl)-1,1-dioxo-1,2,5-thiadiazolidin-3-one;

or a pharmaceutically acceptable salt thereof.

13. A pharmaceutical composition, comprising:
a therapeutically effective amount of the compound of claim 1, or a pharmaceutically acceptable salt thereof, in combination with one or more pharmaceutically acceptable carriers.

14. A method for the inhibition of PTPase activity, comprising:
administering to a mammal in need thereof a therapeutically effective amount of the compound of claim 1, or a pharmaceutically acceptable salt thereof.

15. The method according to claim 14, further comprising administering a therapeutically effective amount of a combination of an anti-diabetic agent, a hypolipidemic agent, an anti-obesity agent or an anti-hypertensive agent.

16. A method for lowering glucose levels in mammals, comprising:
administering to a mammal in need thereof a therapeutically effective amount of the compound of claim 1, or a pharmaceutically acceptable salt thereof.

17. A method for the treatment of insulin resistance, glucose intolerance, type 2 diabetes, obesity, or hypertension, comprising:
administering to a mammal in need thereof a therapeutically effective amount of the compound of claim 1, or a pharmaceutically acceptable salt thereof, wherein said treatment is palliative.

* * * * *